United States Patent
Lewy et al.

(10) Patent No.: US 6,638,963 B1
(45) Date of Patent: *Oct. 28, 2003

(54) METHODS FOR TREATING CIRCADIAN RHYTHM DISORDERS

(75) Inventors: Alfred J. Lewy, Portland, OR (US); Robert L. Sack, Portland, OR (US)

(73) Assignee: Oregon Health and Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/840,382

(22) Filed: Apr. 29, 1997

Related U.S. Application Data

(63) Continuation-in-part of application No. 08/778,842, filed on Jan. 6, 1997, now Pat. No. 6,069,164, which is a division of application No. 08/110,878, filed on Aug. 24, 1993, now Pat. No. 5,591,768, which is a continuation-in-part of application No. 08/077,426, filed on Jun. 15, 1993, now Pat. No. 5,420,152, which is a division of application No. 07/842,723, filed on Feb. 25, 1992, now Pat. No. 5,242,941, which is a continuation of application No. 07/621,866, filed on Dec. 4, 1990, now abandoned, which is a continuation-in-part of application No. 08/779,797, filed on Jan. 7, 1997, now abandoned, which is a continuation of application No. 08/454,545, filed on May 30, 1995, now Pat. No. 5,716,978, which is a division of application No. 08/077,426, filed on Jun. 15, 1993, now Pat. No. 5,420,152, which is a division of application No. 07/842,723, filed on Feb. 25, 1992, now Pat. No. 5,242,941, which is a continuation of application No. 07/621,866, filed on Dec. 4, 1990, now abandoned.

(51) Int. Cl.[7] .................. A61K 31/40; A61K 31/405
(52) U.S. Cl. .................. 514/415; 514/416; 514/418; 514/419; 548/491; 548/494; 548/495; 548/496
(58) Field of Search .................. 514/415, 416, 514/418, 419; 548/495, 496, 491, 494

(56) References Cited

U.S. PATENT DOCUMENTS

| | | | |
|---|---|---|---|
| 2,853,420 A | 9/1958 | Lowey | 167/82 |
| 3,538,214 A | 11/1970 | Polli et al. | 424/19 |
| 3,835,221 A | 9/1974 | Fulberth et al. | 424/19 |
| 4,083,949 A | 4/1978 | Benedikt | 424/19 |
| 4,341,759 A | 7/1982 | Bogentoft et al. | 424/21 |
| 4,505,890 A | 3/1985 | Jain et al. | 424/21 |
| 4,572,833 A | 2/1986 | Pedersen et al. | 424/20 |
| 4,600,723 A | 7/1986 | Short et al. | 514/416 |
| 4,665,086 A | 5/1987 | Short et al. | 514/416 |
| 4,687,763 A | 8/1987 | Wurtman | 514/53 |
| 4,882,137 A | 11/1989 | Staples et al. | 424/423 |
| 4,945,103 A | 7/1990 | Cohen | 514/419 |
| 5,163,426 A | 11/1992 | Czeisler et al. | 128/395 |
| 5,167,228 A | 12/1992 | Czeisler et al. | 128/395 |
| 5,169,642 A | 12/1992 | Brinker et al. | 424/488 |
| 5,176,133 A | 1/1993 | Czeisler et al. | 128/395 |
| 5,242,941 A | 9/1993 | Lewy et al. | 514/416 |
| 5,304,212 A | 4/1994 | Czeisler et al. | 607/88 |
| 5,420,152 A | 5/1995 | Lewy et al. | 514/419 |
| 5,449,683 A | 9/1995 | Wurtman | 514/415 |
| 5,498,423 A | 3/1996 | Zisapel | 424/464 |
| 5,503,637 A | 4/1996 | Kyricos et al. | 607/88 |
| 5,545,192 A | 8/1996 | Czeisler et al. | 607/88 |
| 5,591,768 A | 1/1997 | Lewy et al. | 514/416 |

FOREIGN PATENT DOCUMENTS

| | | |
|---|---|---|
| EP | 126630 | 11/1984 |
| EP | 246910 | 11/1987 |
| EP | 518468 | 12/1992 |
| EP | 578620 | 1/1994 |
| WO | WO 8503227 | 8/1985 |
| WO | WO 9307870 | 4/1993 |
| WO | WO 9503043 | 2/1995 |

OTHER PUBLICATIONS

Aldhous et al., "Plasma concentrations of melatonin in man following oral absorption of different preparations," *Br. J. Clin. Pharmac.* 19:517–521 (1985).

(List continued on next page.)

Primary Examiner—Peter O'Sullivan
(74) Attorney, Agent, or Firm—McDonnell Boehnen Hulbert & Berghoff

(57) ABSTRACT

A method for treating circadian rhythm disorders is described. The method involves the administration of melatonin, melatonin agonists or compounds that stimulate endogenous melatonin production so that the durations of the effective plasma concentrations of melatonin, melatonin agonists or compounds that stimulate endogenous melatonin production overlap with onset or offset of pre-treatment endogenous melatonin production, to provide a circadian-rhythm phase advance or phase delay, respectively. The methods of the invention also provide for concentration and/or duration of the effective plasma concentrations of melatonin, melatonin agonists or compounds that stimulate endogenous melatonin production to be greater in the time interval between about 8 hours before the dim light endogenous melatonin onset (DLMO) to about 4 hours after DLMO than in the time interval from about 4 hours after DLMO to about 8 hours before DLMO to achieve a circadian-rhythm phase advance. The methods of the invention also provide for concentration and/or duration of the effective plasma concentrations of melatonin, melatonin agonists or compounds that stimulate endogenous melatonin production to be greater in the time interval between about 4 hours after DLMO to about 8 hours before DLMO than in the time interval from about 8 hours before DLMO time to about 4 hours after DLMO to achieve a circadian-rhythm phase delay. In addition, the invention provides methods for regulating a human's exposure to light and dark to prevent or enhance, respectively, the human's endogenous production of melatonin. The use of melatonin antagonists, inverse agonists and melatonin inhibitory compounds such as beta-blockers for achieving a circadian-rhythm phase-shifting effect (opposite to that of melatonin administration) are also provided by the invention. The methods of the invention are illustrated by teachings for use of these methods for alleviating a variety of circadian rhythm-related disorders, including jet lag, winter depression, shift work-related desynchronies and sleep phase disorders.

10 Claims, 8 Drawing Sheets

OTHER PUBLICATIONS

Arendt et al., 1984, "The effects of chronic, small doses of melatonin given in the late afternoon on fatigue in man: A preliminary study," *Neurosci. Lett.* 45:317–325.

Arendt et al., 1985, "Some effects of melatonin and the control of its secretion in humans," *CIBA Found. Symp.* 117:266–283.

Arendt et al., 1987, "Some effects of jet–lag and their alleviation by melatonin," *Ergonomics* 30:1379–1393.

Armstrong, 1989, "Melatonin and circadian control in mammals," *Experientia* 45:932–938.

Armstrong, 1991, "Treatment of sleep disorders by melatonin administration," *Adv. In Pineal Res.* 6:263–274.

Blood et al., 1993, "Serengeti® vermilion sunglasses inhibit the suppressant effect of bright light on melatonin secretion," *Sleep Res.* 22:394 (Abst.).

Cagnacci et al., 1992, "Melatonin: A Major Regulator of the Circadian Rhythm of Core Temperatures," *J. Clin. Endocrinol. Metab.* 75(2):447–452.

Claustrat et al., 1992, "Melatonin and jet–lag: confirmatory result using a simplified protocol," *Biol. Psychiatry* 32:705–711.

Czeisler et al., "Bright Light Resets the Human Circadian Pacemaker Independent of the Timing of the Sleep–Wake Cycle," *Science* 233:667–671 (1986).

Czeisler et al., "Bright Light Induction of Strong (Type O) Resetting of the Human Circadian Pacemaker," *Science* 244:1328–1333 (1989).

Dahlitz et al., "Delayed sleep phase syndrome response to melatonin," *The Lancet* 337:1121–1127 (1991).

Deacon & Arendt, "Melatonin–induced temperature suppression and its acute phase–shifting effects correlate in a dose–dependent manner in humans," *Brain Res.* 688:77–85 (1995).

Gwinner, 1978, "The effects of pinealectony on circadian locomotor activity rhythms in European starlings, *Sturnus vulgaris,*" *J. Comp. Physiol.* 126:123–129.

Hamilton, "Development of a Rating Scale for Primary Depressive Illness," *Brit. J. Soc. Clin. Psychol.* 6:278–296 (1967).

Hoban et al., "Entrainment of a Free–Running Human with Bright Light?" *Chronobiol. Intl.* 6:347–353 (1989).

Iguchi et al., "Melatonin serum levels and metabolic clearance rate in patients with liver cirrhosis," *Clin. Endocrinol. Metab.* 54:1025–1027 (1982).

Lewy and Markey, 1978, "Analysis of Melatonin in Human Plasma by Gas Chromatography Negative Chemical Ionization Mass Spectrometry," *Science* 201:741–743.

Lewy et al., 1992, "Melatonin shifts human circadian rhythms according to a phase–response curve," *Chronobiol. Int'l.* 9:380–392.

Lewy et al., "Melatonin light and chronobiological disorders," in *Photoperiodism, Melatonin and the Pineal Gland* (Evered et al., eds.) pp. 231–252 (1985).

Lewy et al., "Antidepressant and Circadian Phase–Shifting Effects of Light," *Science* 235:352–354 (1987).

Mallo et al., "Pharmacokinetics of melatonin in man after intravenous infusion and bolus injection," *J. Clin. Pharmacol.* 38:297–301 (1990).

Minors et al., "A human phase–response curve to light," *Neurosci. Lett.* 133:36–40 (1991).

Nickelsen et al., 1991, "The effects of 6–, 9–and 11–hour time shifts on circadian rhythms: adaptation of sleep parameters and hormonal patterns following the intake of melatonin or placebo," *Adv. Pineal Res.* 5:303–306.

Parry et al., 1987, "Treatment of a Patient With Seasonal Premenstrual Syndrome," *Am. J. Psychiatry* 144(6):762–766.

Petrie et al., 1989, "Effect of melatonin on jet lag after long hauls," *Br. Med. J.* 298:705–707.

Rosenthal et al, 1988, "Atenolol in seasonal affective disorder: A test of the melatonin hypothesis," *Amer. J. Psychiatry* 145:52–56.

Samel et al., 1991, "Influence of melatonin treatment on human circadian rhythmicity before and after simulated 9–hr time shift," *J. Biol. Rhythms* 6:235–248.

Schlager et al., "Early–Morning Administration of Short–Acting β Blockers for Treatment of Winter Depression," *Amer. J. Psych.* 151:1383–1385 (1994).

Terman et al., "Light Therapy for Seasonal Affective Disorder," *Neuropsychopharmacol.* 2:1–22 (1990).

Underwood, 1986, "Circadian Rhythms in Lizards: Phase Response Curve for Melatonin," *J. Pineal Res.* 3:187–196.

Waldhauser et al., "Melatonin in human body fluids: Clinical significance," in *The Pineal Gland*, (R. Reiter, ed.), Raven Press: New York, p. 359.

Wever et al., "Bright Light Affects Human Circadian Rhythms," *Eur. J. Physiol.* 396:85–87 (1983).

Wever, "Light Effects of Human Circadian Rhythms: A Review of Recent Andechs Experiments," *J. Biol. Rythms* 4:161–186 (1989).

Wirz–Justice et al., 1990, "Morning or night–time melatonin in ineffective in seasonal affective disorder," *J. Psychiatr. Res.* 24:129–137.

Zaidan et al., "Melatonin Is Able to Influence Its Secretion in Humans: Description of a Phase–Response Curve," *Neuroendocrinol.* 60:105–112 (1994).

Petrie et al., "A Double–Blind trial of Melatonin as a Treatment for Jet Lag in International Cabin Crew", Biol. Psychiatry, 1993;33:526–530.

Arendt, et al, "Jet Lag and Sleep Disruption, Principles and Practice of Sleep Medicine" Third Edition, 2000, 591–599.

Arendt, et al., "Treatment of Circadian Rhythm Disorders–Melatonin", Chronobiology International, 14(2), 185–204 (1997).

Aleem FA Weitzman ED, Weinberg U. Suppression of basal luteinizing hormone concentrations by melatonin in postmenopausal women. *Fertility and Sterility* 42:923–925, 1984.

Anderson RA, Lincoln GA, Wu FCW, Melatonin potentiates testosterone–induced suppression of luteinizing hormone secretion in man. *Human Reproduction* 8:1819–1822, 1993.

Antón–Tay F, Chou C, S.A, Wurtman RJ. Brain serotonin concentration: elevation following intraperitoneal administration of melatonin. *Science* 162:277–278, 1968.

Antón–Tay F, Diaz JL, Fernández–Guardiola A. On the effect of melatonin upon the human brain: it's possible therapeutic implications. *Life Sci* 10:841–850, 1971.

Antón–Tay F. Melatonin. Effects of brain function. In: Costa E, Gessa GL, Sandler M. *Serotonin—New Vistas: Biochemistry and Behavioral and Clinical Studies. Advance in Biochemical Psychopharmacology.* New York: Raven Press, 315–324, 1974.

Arendt, J, Marks V. Can melatonin alleviate jet lag? *Br Med J* 287: 426, 1983.

Arendt, J, Aldhous M, Marks V. Alleviationof "jet lag" by melatonin: preliminary results of controlled double blind trial. *Br Med J* 292:1170, 1986.

Arendt J, Marks V. Jet lag and melatonin [letter]. *Lancet* ii:698–699, 1986.

Arendt J, Broadway J. Light and melatonin as zeitgebers in man. *Chronobiol Int* 4:273–282, 1987.

Arendt J, Aldhous M, Wright J. Synchronisation of a disturbed sleep–wake cycle in a blind man by melatonin treatment [letter]. *Lancet* i:772–773, 1988.

Armstrong, SM, Cassone VM, Chesworth MJ, Redman JR, Short RV. Synchronization of mammalian circadian rhythms by melatonin. *J Neutral Trans Suppl* 21:375–394, 1986.

Armstrong SM, Redman JR. Melatonin: a chronobiottic with anti–aging properties? *Med Hyp* 34:300–309, 1991.

Attenburrow SM, Redman JR. Melatonin: a chronobiotic with anti–aging properties? *Med Hyp* 34:300–309, 1991.

Attenburrow ME, Dowling BA, Sargent PA, Sharpley AI, Cowen PJ. Melatonin phase advances circadian rhythms. *Psychopharmacology* 121:503–505, 1995.

Badia P, Hughes RJ, Wright KP, Murphy PJ, Myers BL. High dose melatonin facilitates sleep without negative carryover on performance. *Sleep Re* 25, In Press:1995.

Birau N, Petersen U, Meyer C. Gottschelk J. Hypotensive effect of melatonin in essential hypertension. *ICRS Med Biochem* 9:906–917, 1981.

Bispink G. Zimmerman R, Weise HC, Leidenberger F. Influence of melatonin on the sleep–independent component of prolactin secretion. *J Pineal Res* 8:97–106, 1990.

Blood ML, Sack RL, Lewy AJ. Duration of daytime sleep in night workers depends on resetting the circadian pacemaker. *Sleep Res* 23: 478, 1994.

Burns JK. Administration of melatonin to non–human primates and to women with breast carcinoma. *Journal of Physiology* 229:38P–39P, 1972.

Cagnacci A. Elliott JA, Yen SSC. Amplifications of pulsatile LH secretion by exogenous melatonin in women. *J Clin Endocr Metab* 73:210–212, 1991.

Cagnacci A. Soldani R, Yen SS. The effect of light on core body temperature is mediated by melatonin in women. *J Clin Endocr Metab* 76:1036–1038, 1993.

Cagnacci A, Paoletti AM, Soldani R, Orru M, Mashio E, Melis GB. Melatonin enhances the luteinizing hormone and follicle–stimulating hormone responses to gonadortrophin–releasing hormone in the follicular, but not in the luteel, menstrual phase. *J Clin Endocr Metab* 80:1095–1099, 1995.

Cagnacci A, Soldani R, Yen SSC. Exogenous melatonin enhances lutenizing hormone levels of women in the follicular but not in the letter menstrual phase. *Fertility and Sterility* 63:996–999, 1995.

Cagnacci A. Soldani R, Yen SSC. Melatonin enhances cortisol levels in aged but not young women. *Eur J. Endocrinol* 133:691–695, 1995.

Cagnacci A, Soldani R, Yen SSC. Contemporaneous melatonin administration modifies the circadian response to nocturnal bright light stimuli. *Am J Physiol* 272:R242–R486, 1997.

Cagnacci A, Arangino S, Angiolucci M, Mashio E, Longu G, Melis GB. Potentially beneficial cardiovascular effects of melatonin administration in women. *J Pineal Res* 22:16–19, 1997.

Cagnoni ML, Lombardi A, Cerinic MC, Dedola GL, Pignone A. Melatonin for treatment of chronic refractory sarcoidosis [letter]. *Lancet* 346:1229–1230, 1995.

Cajochen C, Kräuchi, K, Graw P, Möri D, von Arx M, Wirz–Justice A. Acute melatonin augment subjective sleepiness and waking EEG power density in the theta range. *Sleep Res* 24A:112, 1995.

Cajochen C. Kräuchi K, Möri D, von Arx M, Wirz–Justice A. Melatonin increases sleepiness and theta activity in the wake EEG, but does not affect the sleep EEG except to lenghten the first REM sleep episode. *Soc Light Biol Rhythms Abst* 7:91, 1995.

Cajochen C, Kräuchi, K, Möri D, Hetch C, Wirz–Justice A. A single administration of melatonin or the melatonin agonist s–20098 lengthens the first REM sleep episode. *Sleep Res* 24:40, 1995.

Cajochen C, Kräuchi, K, Danilenko KV, Renz C, Wirz–Justice A. Melatonin and bright light interactions on the waking EEG. *Sleep Res* 26:70, 1997.

Cajochen C, Kräuchi K, Hofstetter M, Renz C, Wirz–Justice A. The acute soporific action of melatonin on the waking EEG is attenuated by an orthostatic challenge. *Sleep Res* 26:71, 1997.

Carman JS, Post RM, Buswell R, Goodwin FK. Negative effects of melatonin on depression. *am J Psychiatry*133:1181–1186, 1976.

Cavallo A, Ritschel WA. Pharmacokinetics of melatonin in human maturation. *J Clin Endocr Metab* 81:1882–1886, 1996.

Claustrat B, Bars D, Brun J, Thivolle P, Mallo C, Arendt J, Chazot G. Plasma and brain pharmacokinetic studies after intravenous administration of cold or $^{11}$C labeled melatonin. In: Reiter R, Pang S. *Advances in Pineal Research*. London: John Libbey, 305–310, 1989.

Claustrat B, Brun J, Zaidan R, Chazot G. Neopharmacology and pharmacokinetics of melatonin in humans. *J Sleep Res* 1:44, 1992.

Comperatore CA,Lieberman HR, Kirby AW, Adams B, Crowley JS. Melatonin efficacy in aviation missions requiring rapid deployment and night operations. *Av Sp Envir Med* 67: 520–524, 1996.

Cotzias GC, Papavasiliou PS, Ginos J, al. e. Metabolic modifications of Parkinson's disease and of chronic manganese poisoning. *Annual Rev Med* 22:305–326, 1971.

Cramer H, Kendel K, Beck U. Influence of melatonin on sleep in humans. In: Koella WP, Levin P. Sleep. *Phsiology, biochemistry, psychology, pharmacology, clinical implications*. Basel: Krager, S., 488–491, 1973.

Cramer H, Rudolph J, Consbruch U, Kendel K. On the effects of melatonin on sleep and behavior in man. In: Costa E, Gessa GL, Sandler M. Serotonin—New Vistas: Biochemistry and Behavioral and Clinical Studies. *Advances in Biochemical Psychopharmacology*. New York: Raven Press, 187–191, 1974.

Dagen Y, Yovel I, Hallis D. Melatonin treatment of DSPS: a follow–up study. *Sleep Res* 26:349, 1997.

Dagen Y, Zisapel N, Nof D, Laudon M, Atsmon J. Rapid reversal of tolerance to benzodiazepine hypnotics by treatment with oral melatonin: a case administration. *Sleep* 18:11–21, 1995.

Dawson, D, Gibbon S, Singh P. The hypothermic effect of melatonin on core body temperature: is more better: *J Pineal Res* 20:192–197, 1996.

Deacon S, English J, Arendt J. Acute phase–shifting of melatonin associated with suppression of core body temperature in humans. *Neurosci Lett* 178:32–34, 1994.

Deacon S. Arendt J. Adapting to phase shifts, II. Effects of melatonin and conflicting light treatment. *Physiol Behav* 59:675–682, 1996.

deVries MW, Peeters FPML. Melatonin as a therapeutic agent in the treatment of sleep disturbance in depression. *Journal of Nervous and Mental Disease* 185:201–202, 1997.

Di WL, Kadva A, Johnston A, Silman R. Variable bioavailability of oral melatonin. *N Eng J Med* 336:1028–1029, 1997.

Dijk DJ, Roth C, Landolt HP, Werth E, Aeppli M, Achermann P, Borbély AA. Melatonin reduces low-frequency EEG activity during daytime sleep. *Sleep Res* 24A:117, 1995.

Dollins AB, Lynch HJ, Wurtman RJ, Deng MH, Kischka KU, Gleason RE, Lieberman HR, Effect of pharmacologica daytime doses of melatonin on human mood and performance. *Psycholpharmacology*112:490–496, 1993.

Dollins AB, Zhdanova IV, Wurtman RJ, Lynch HJ, Deng MH. Effect of inducing nocturnal serum melatonin concentrations in daytime on sleep, mood, body temperature, and performance. *Proc Natl Acad Sci USA* 91:1824–1828, 1994.

Ellis CM, Lemmens G, Parkes JD. Melatonin and insomnia. *J Sleep Res* 5:61–65, 1996.

English J, Aldhous M, Arendt J, Ravault JP, Wirz–Justice A. Direct radioimmunoassay in human saliva [Abstract 139]. In: *The Tth Colloquium of the European Pineal Study Group*. England: Guildford, 1990.

Etzioni A, Luboshitzky R, Tiosano D, Ben–Harush M, Goldsher D, Lavie P. Melatonin replacement corrects sleep disturbances in a child with pineal tumor. *Neurology*. 46(1):261–3 46:261–263, 1996.

Ferini–Strambi L, Zucconi M, Biella G, Oldani A, Stankov B, Fraschini F, Oldani A, Smime S. Macro–and micro–structure of sleep after melatonin in healthy subjects. Presented at the $6^{th}$ Annual Meeting of the Association of Professional Sleep Societies, Annual Meeting Abstracts, 1992. Ferini–Strambi L, Zucconi M, Biella G, Stankov B, Fraschini F, Oldani A, Smime S. Effect of melatonin on sleep microstructure: preliminary results in healthy subjects. *Sleep* 16:744–747, 1993.

Ferini–Strambi L, Oldani A, Zucconi M, Stankov B, Castronovo C, Frashcini F, Smime S. Triazolam and melatonin effects on cardiac automatic function during sleep. *Clinical Neuropharmacology* 18:405–409, 1995.

Fernández–Guradiola A, Antón–Tay F. Modulation of subcortical inhibitory mechanisms by melatonin. In: Myers RD, Drucker–Colin RR. *Neurohumoral Coding of Brain Function*. New York: Plenum Press, 273–287, 1974.

Fideleff H, Aparicio NJ, Giutelman A, Debeljuk L, Mancini A, Cramer C. Effect of Melatonin on the basal and stimulated gonadotrophin levels in normal men and postmenopausal women. *J Clin Endocr Metab* 42:1014–1017, 1976.

Folkland S, Arendt J, Clark M. Can melatonin improve shift workers' tolerance of the night shift? Some preliminary findings. *Chronobiol Int* 10:315–320, 1993.

Forsling ML, Sawyer A, Sharma S, Williams AJ. The effect of melatonin on the vasopressin response to increased plasma sodium in man. *Sleep Res* 26:139, 1997.

rsling ML, Sawyer A, Sharma S, Williams AJ. The effect of melatonin on basal vasopressin and oxytocin release in man. *Sleep Res* 26:140, 1997.

Garfinkle D, Laudon M, Dudai S, Karasic A, Nof D, Zisapel N. Drug–induced sleep disturbances in the elderly: effects of melatonin therapy. *Sleep Res* 24:521, 1995.

Garfinkle D, Laudon M, Nof D Zisapel N. Treatment of elderly benzodiazepine–users with controlled–release melatonin: improvement of sleep quality. *Sleep Res*24A: 303, 1995.

Garfinkle D, Laudon M, Nof D, Zisapel N. Improvement of sleep quality in elderly people by controlled–realease melatonin [comment]. *Lancet* 346:541–544, 1995.

Gilbert SS, van den Heuvel C, Dawson D. Peripheral heat loss: a predictor of the hypothermic response to melatonin in elderly women. *Sleep Res* 26:100, 1997.

Goldberg MJ, Bergstrom RF, Smith BP, Simcox EA, Thomasson HR, Shipley LA. Melatonin: pharmacokinetics and effect on body temperature in men. *Sleep Res* 26:101, 1997.

Gonzalez R, Sanchez A, Ferguson JA, Balmer C, Daniel C, Cohn A. Robinson WA. Melatonin therapy of advanced human malignant melanoma. *Melanoma Research* 1:237–243, 1991.

Gordon K, Camfield P, Dooley J, Crist B. Dramatically successful treatment of severe sleep disturbance in developmentally handicapped children with melatonin [abstract]. *Ann Neurol* 34:504, 1993.

Haimov I, Zisapel N. Tzischinsky O, Lauden M, Lavie P. Melatonin treatment of sleep onset insommnia in the elderly. *Sleep Res* 22:205, 1993.

Haimov I, Lavie P, Laudon M, Herer P, Vigder C, Zisapel N. Melatonin replacement therapy of elderly insomniacs. *Sleep* 18:598–603, 1995.

Haimov I, Lavie P. Potential of melatonin replacement therapy in older patients with sleep disorders. *Drugs and Aging* 7:75–78, 1995.

Hätönen T, Alila A, Laakso ML. Exogenous melatonin fails to counteract the light–induced phase delay of human melatonin rhythm. *Brain Res* 710:125–130, 1996.

Hughes RJ, Badia P, French J, Santiago L, Plenzler S. Melatonin induced changes in body temperature and daytime sleep. *Sleep Res* 23:496, 1994.

Hughes RJ, Sack RL, Singer CM, Lewy AJ. A comparison of the hypnotic efficacy of melatonin and temazepam on noctural sleep in healthy adults. *Sleep Res* 24A:124, 1995.

James SP, Mendelson WB, Sack DA, Rosenthal NE, Wehr TA. The effect of melatonin on normal sleep. *Neuropsychopharmacol* 1:41–44, 1987.

James SP, Sack DA, Rosenthal NE. Melatonin administration in insomnia. *Neuropsychopharmacol* 3:19–23, 1990.

Jan JE, Espezel H, Appleton RE. The treatment of sleep disorders with melatonin. *Develop Med Child Neurol* 36:97–107, 1994.

Jan JE, Espezel H. Melatonin treatment of chronic sleep disorders [letter]. *Developmental Medicine & Child Neurology* 37:279–80, 1995.

Jean–Louis G, Zizi F, von Gizycki H, Spielman AJ, Stampi C, Friedman K, Nunes J, Taub H. The efficacy of melatonin on the sleep of normals as assessed by actigraphy. *Sleep Res* 25:59, 1996.

Jean–Louis G, Spielman A, Zizi F, von Gizycki H, Stampi C, Fookson J, Taub H. Resynchronization of rest–activity rhythm with exogenous melatonin in a patient with Alzheimer's disease. *Sleep Res.* 26:103, 1997.

Jean–Louis G, Spielman A, Zizi F, von Gizycki H, Stampi C, Fookson J, Nunes J, Taub H. The re–entrainment of circadian rhythm in midly demented elderly individuals with melatonin therapy. *Sleep Res* 26:104, 1997.

Jean–Louis G, Spielman A, Zizi F, von Gizycki H, Shentov D, Stampi C, Fookson J, Nunes J, Taub H. Cognitive and behavioral effects of melatonin therapy in mildly demented elderly individuals. *Sleep Res* 26:105, 1997.

Jean–Louis G, Zizi F, Spielman A, Stampi C, Taub H. Behavioral and cognitive predictors of sleepiness induced by melatonin therapy. *Sleep Res* 26:107, 1997.

Jean–Louis G, Zizi F, von Gizycki H, DiPalma J, Nunes J, Spielman A, Stampi C, Taub H. Acute effects of melatonin therapy on behavior, mood, and cognition. *Sleep Res* 26:108, 1997.

Kelly M, Reid K, Dawson D. Melatonin administration decreases core temperature and alertness. *Sleep Res* 24A:165, 1995.

Koulu M, Lammintausta R. Effect of melatonin of L–tryptophan and apomorphine stimulated growth hormone secretion in man. *J Clin Endocr Metab* 49:70–72, 1979.

Kräuchi K, Cajochen C, Möri D, Hetsch C, Wirz–Justice A. Acute melatonin can phase advance rhythms of temperature and fatigue. Presented at the $2^{nd}$ Swiss Poster Meeting on Basic and Clinical Neuroscience, Geneva, Switzerland, 1995. Kräuchi K, Cajochen C, Möri D, Hetsch C, Wirz–Justice A. Evidence for a phase advance in circadian temperature regulation after acute melatonin and a melatonin agonist (S–20089). *Sleep Res* 24:526, 1995.

Kräuchi K, Cajochen C, Danilenko KV, Wirz–Justice A. Melatonin and bright light interactions on circadian phase of core body temperature and subjective sleepiness. *Sleep Res* 26:78, 1997.

Kräuchi K, Cajochen C, Hofmann M, Wirz–Justice A. Melatonin and orthostasis: interactions of posture with subjective sleepiness, heart rate, and skin and core temperature. *Sleep Res* 26:79, 1997.

Kräuchi K, Cajochen C, Danilenko KV, Wirz–Justice A. The hypothermic effect of late evening melatonin does not block the phase delay induced by concurrent bright light. *Soc Light Treatment Biol Rhythms Abst* 9:12, 1997.

Lapierre O, Dumont M, Lespérance P, Montplaisir J. Entrainment of a free–running sleep–wake cycle with melatonin in a blind retarded child. *Sleep Res* 22:627, 1993.

Lapierre O, Dumont M, Melatonin treatment of a non–24–hour sleep–wake cycle in a blind retarded child. *biol Psychiat* 38:119–122, 1995.

Le Bars D, Thivolle P, Vitte PA, Bojkowski C, Chazot G, Arendt, Frankowiak RSJ, Claustrat B. Pet and plasma pharmacokinetic studies after bolus intravenous administration of $[11^C]$ melatonin in humans. *Nucl Med Biol* 18:357–362, 1991.

Leach C, Thorburn G. A comparison of the inhibitory effects of melatonin and indomethacin on platelet aggregation and thromboxane release. *Prostaglandins* 20:51–56, 1980.

Lee BJ, Parrott KA, Ayres JW, Sack RL. Preliminary evaluation of transdermal delivery of melatonin in human subjects. *Research Communications in Molecular Pathology and Pharmacology* 85:337–346, 1994.

Lerner AB, Case JC, Melatonin. *Federal Proceedings* 19:590–592, 1960.

Lerner AB, Nordlund JJ. Melatonin: clinical pharmacology. *J Neural Trans Suppl* 13:339–347, 1978.

Lespérance P. Lapierre O, Gosselin A, Montplaisir J. Effects of exogenous melatonin on excessive daytime somnolence associated with fragmented sleep: and open clinical trial. *Sleep Res* 26:111, 1997.

Lewy AJ, Sack RL, Latham JM. Exogenous melatonin administration shifts circadian rhythms according to a phase response curve [Abstract 021]. In: *The Vth Colloquium of the European Pineal Study Group*. England: Guildford, 1990.

Lewy AJ, Sack RL, Latham JM. Circadian phase shifting of blind and sighted people with exogenous melatonin administration: evidence for a phase response curve. *Soc. Light Treatment Biol Rhythms Abst* 2:22, 1990.

Lewy AJ, Sack RL, Latham J. A phase response curve for melatonin administration in humans. *Sleep Res* 20:461, 1991.

Lewy AJ, Sack RL, Latham JM. Melatonin and the acute suppressant effect of light may help regulate circadian rhythms in humans. In: Arendt J, Pevét P. *Advances in Pineal Research*. London: John Libbey, 285–293, 1991.

Lewy AJ, Sack RL. Use of melatonin to assess and treat circadian phase disorders. In: Touitou Y, Arendt J, Pévet P. *Melatonin and the Pineal Gland–from Basic Science to Clinical Application*. New York: Elsevier, 205–210, 1993.

Lewy AJ, Sack RL. The use of melatonin as a marker for circadian phase and as a chronobiotic in blind and sighted humans. In: Wetterberg L. *Light and Biological Rhythms in Man*. New York: Pergamon Press, 173–185, 1993.

Lieberman HR, Waldhauser F, Garfield G, Lynch HJ, Wurtman RJ. Effects of melatonin on human mood and performance. *Brain Res* 323:201–207, 1984.

Lieberman HR. Behavior, sleep and melatonin. *J Neural Trans Suppl* 21:233–241, 1986.

Lieberman HR, Wurtman RJ, Emde CC, Roberts C, Coviella ILG. The effects of low doses of caffeine on human performance and mood. *Psychopharmacology* 92:308–312, 1987.

Lissoni P, Resentini M, Mauri R, De Medici C, Morabito F, Esposti D, Di Bella L, Esposti G, Rossi D, Parravicini L, Legname G, Frachini F. Effect of an acute injection of melatonin on the basal secretion of hypophysical hormones in prepubertal and pubertal healthy subjects. *Acute Endocrinologica (Copenhagen)* 111:305–311, 1986.

Lisstoni P, Barni S, Tancini G, al. e. Clinical study of melatonin in untreatable advanced cancer patients. *Tumori* 73:475–480, 1987.

Lisstoni P, Barni S, Crispino S, Tancini G, Fraschini F. Endoctrine and immune effects of melatonin therapy in metastic cancer patients. *Eur J Cancer Clin Oncol* 25:789–795, 1989.

Lissoni P, Barni S, Cazzaniga M, Ardizzoia A, Rovelli F, Brivio F, Tancini G. Efficacy of concomitant administration of the pineal hormone melatonin in cancer immunotherapy with low–dose IL–2 in patients with advanced solid tumors who had progressed on IL–2 alone. *Oncology* 51:344–347, 1994.

Lushington K, Pollard K, Lack L, Kennaway D, Dawson D. The effects of exogenous daytime melatonin on sleep latency and core body temperature in older good and poor sleepers. *Sleep Res* 26:112, 1997.

MacFarlene JG, Cleghorn JM, Brown GM, Streiner DL. The effects of exogenous melatonin on the total sleep time and daytime alertness of chronic insomniacs: a preliminary study. *Biol Psychiat* 30:371–376, 1991.

Maksoud A, Moore CA, Hirshkowitz M. The effect of melatonin administration on patients with sleep apnea. *Sleep Res* 26:114, 1997.

Matsumoto M, Sack RL, Blood ML, Lewy AJ. Exogenous melatonin administration does not affect the amplitude of endogenous melatonin production in humans. *Sleep Res* 25:561, 1996.

Matsumoto M, Sack RL, Blood ML, Lewy AJ. The amplitude of endogenous melatonin production is not affected by melatonin treatment in humans. *J Pineal Res* 22:42–44, 1997.

Matthews C, Kennaway D, Fellenberg, AJG, Phillipou D, Cox LW, Seamark RF. Melatonin in man. *Adv biosci* 29:371–381, 1981.

Mauri R, Lissoni P, Resentini M, De Medici C, Morabito F, Djemal S, Di Bella L, Fraschini F. Effects of melatonin on PRL secretion during different photoperiods of the day in prepubertal and pubertal healthy subjects. *J Endocrinol Invest* 8:337–341, 1985.

Maurizi CP. The mystery of Alzheimer's disease and its prevention by melatonin. *Med Hyp* 45:339–340, 1995.

McArthur AJ, Sack RL, Hughes RJ, Lewy AJ. Melatonin, a stronger zeitgerber than light in some sighted individuals? *Sleep Res* 24a:527, 1995.

McElhinney DB, Hoffman SJ, Robinson WA, Ferguson J. Effect of melatonin on human skin color. *Journal of Investigative Dermatology* 102:258–259, 1994.

Mendelson WB, Rosenthal NE, James SP. Melatonin administration and nocturnal sleep in insomniacs. Middleton B, Arendt J, Stone BM, Effect of exogenous melatonin on human activity/rest and rectal temperature rhythms and sleep onset times in constant dim light. *Sleep Res* 24A:528, 1995.

Middleton BA, Stone BM, Arendt J. Melatonin and fragmented sleep patterns. *Lancet* 348:551–552, 1996.

Nagtegaal JE, Smits MG, van der Meer YG. Melatonin: a therapeutic tool for specific sleep disorders. In: Coenen AML. *Sleep–wake Research in The Netherlands*. Leiden, The Netherlands: Dutch Society for Sleep–Wake Research, 119–120, 1994.

Nave R, Shlitner A, Peled R. Lavie P. Melatonin improves evening napping. *Sleep Res* 24:47, 1995.

Nave R. Shlitner A, Peled R, Lavie P. Melatonin improves evening napping. *Eur J Pharmacol* 275:213–216, 1995.

Nordlund J, Lerner A. The effect or oral melatonin on skin color and on the release of pituitary hormones. *J Clin Endocr Metab* 45:768–774, 1997.

Okatani Y, Sagara Y. Role of melatonin in nocturnal prolactin secretion in women with normoprolactinemia and mild hyperprolactinemia. *American Journal of Obstetrics and Gynecology* 168:854–861, 1993.

Oldani A, Ferini–Strambi L, Zucconi M, Stankov B, Frashini F, Smirne S. Melatonin and delayed sleep phase syndrome: ambulatory polygraphic evaluation. *NeuroReport* 6:132–134, 1994.

Paccotti P, Terzolo M, Torta M, Vignani A, Schena M, Piovesan A, Angeli A. Acute administration of melatonin at two opposite circadian stages does not change responses to gonodotrophin releasing hormone, thyrotropin releasing hormone and ACTH in healthy adult males. *J Endocrinol Invest* 10:471–477, 1987.

Paccotti P, Terzolo M, Piovesan A, Torta M, Vignani A, Angeli A. Effects of exogenous melatonin on human pituitary and adrenal secretions. Hormonal responses to specific stimuli after acute administration of different doses at two opposite circadian stages in men. *Chronobiologia* 15:279–288, 1988.

Palm L, Blennow G, Wetterberg L. Correction of non–24–hour sleep/wake cycle by melatonin in a blind retarded boy. *Ann Neurol* 29:336–339, 1991.

Papavasiliou PS, Cotzias GC, Düby SE, Steck AJ, Bell M, Lawrence WH. Melatonin and parkisonism [letter]. *JAMA* 221:88–89, 1972.

Pavel S, Goldstein R, Petrescu M, Popa M. Melatonin, vasotocin, and REM sleep in prepuberal boys. In: Birau N, Schloot W. Melatonin: Current Status and Perspectives. *Advances in the Biosciences*, vol. 29. London: Pergamon Press, 343–347, 1981., Petrie K, Dawson AG, Thompson L, Brook R. A double–blind trial of melatonin as a treatment for jet lag in international cabin crew. *Biol Psychiat* 33:526–30, 1993.

Petterborg LJ, Thalén BE, Kjellman BF, Wetterberg L. Effect of melatonin replacement on serum hormone rhythms in a patient lacking endogenous melatonin. *Brain Res Bull* 27:181–185, 1991.

Reid K, Dawson D. Day–time melatonin administrations: effect on core temperature and sleep onset latency. *Sleep Res* 24a:173, 1995.

Reinhard U, Kendel K, Burmeister P, Böhme W, Cramer H. Melatonin. Influence on afternoon sleep pattern and plasma levels of human growth hormone and cyclic AMP in healthy volunteers. In: Levin P, Koells WP. *Sleep 1974*. Basel: Karger, S., 518–522, 1975.

Rogers NL, Phan O, Kennaway D, Dawson D. Effect of daytime oral melatonin administration on cognitive psychomotor performance in humans. *Sleep Res* 26:212, 1997.

Rogers NL, van den Heuval C, Lushington K, Kennaway D, Dawson D. Effect of transbuccal melatonin administration on sleep in elderly insomniacs. *Sleep Res* 26:482, 1997.

Rosenthal NE, Sack DA, Jacobsen FM, James SP, Parry BL, Arendt J, Tamarkin L, Wehr TA. Melatonin in seasonal affective disorder and phototherapy. *J Neural Trans Suppl* 21:257–267, 1986.

Sack RL, Lewy AJ, Hoban TM. Free–running melatonin rhythms in blind people: phase shifts with melatonin and triazolam administration. In: Rensing L, an der Heiden U, Mackey MC. *Temporal Disorder in Human Oscillatory Systems*. Heidelberg : Springer–Verlag , 219–224, 1987.

Sack RL, Lewy AJ. Melatonin administration phase advances endogeous rhythms in humans. *Sleep Res* 17:396, 1988.

Sack RL, Stevenson J, Lewy AJ. Entrainment of a previously free–running blind human with melaton administration. *Sleep Res* 19:404, 1990.

Sack, RL, Blood ML, Ormerod GM, Rich GB, Lewy AJ. Oral melatonin reverses the alterting effects of nocturnal bright light exposure in humans. *Sleep Res* 21:49, 1992.

Sack RL, Lewy AJ. Human circadian rhythm: lessons from the blind. *Ann Med* 25:303–305. 1993.

Sack RL, Blood ML, Lewy AJ. Phase shifts in melatonin rhythms are highly variable among night–shift worker on the same schedule. *Sleep Res* 23:510, 1994.

Sack RL, Lewy AJ, Hughes RJ, McArthur AJ, Blood ML. Melatonin as a chronobiotic drug. *Drug News and Perspectives* 9:325–332, 1996.

Samuel A, Wegmann HM, Vejvoda M. Circadian adaptation after simulated time shifts–the effect of melatonin. *J Sleep Res* 1:205, 1992.

Samples JR, Krause G, Lewy AJ. Effect of melatonin on intraocular pressure. *Current Eye Research* 7:629–653, 1988.

Sandyk R, Anastasiadis PG, Anninos PA, Tsagas N. Is postmenopausal osteoporosis related to pineal gland function? *Int J Neurosci* 62:215–225, 1992.

Sarrafzadeh A, Wirz–Justice A, Arendt J, English J. Melatonin improves sleep in a blind man. Presented at the 10$^{th}$ Congress of the European Sleep Research Society, Strasbourg, 1990.

Sarrafzadeh A, Wirz–Justice A, Arendt J, English J. Melatonin stabilises sleep onset in a blind man. In: Home JA. *Sleep '90*. Bochum: Patenagel Press, 51–54, 1990.

Shamir E, Rotenberg VS, Elizur A, Zisapel N. Melatonin-mediated increase in eye movement density during REM sleep. *Sleep Res* 26:258, 1997.

Shaw KM, Stern GM, Sandler M. Melatonin and parkinsonism. *Lancet* i:271, 1973.

Shaw KM, Hypothalamo–pituitary–adrenal function in Parkisonian patients treated with melatonin. *Curr Med Res Opin* 4:743–746, 1976.

Shaw K. The pineal gland: a review of the biochemistry, physiology and pharmacological potential of melatonin and other pineal substances. *Adv Drug Res* 11:75–96, 1997.

Sheldon SH, Riter S. Effects of oral melatonin on stablization of sleep/wake cycles in neurologically handicapped children. *Sleep Res* 26:592, 1997.

Sherer MA, Weingartner H, James SP, Rosenthal NE. Effects of melatonin on performance testing in patients with seasonal affective disorders. *Neurosci Lett* 58:277–282, 1985.

Singer C, Jackson J, Moffitt M, Blood M, McArthur A, Sack R, Parrott K, Lewy A. Physiologic melatonin administration and sleep–wake cycle in Alzheimer's disease: a pilot study. *Sleep Res* 23:84, 1994.

Singer C, Parrott K, Sack R, Lewy A. Low dose, sustained–release melatonin treatment in the elderly. *Sleep Res* 23:85, 1994.

Singer C, Wild K, Sack R, Lewy A. High dose melatonin is well tolerated by the elderly. *Sleep Res* 23:86, 1994.

Singer C, McArthur A, Hughes R, Sack R, Kaye J, Lewy A. High dose melatonin administration and sleep in the elderly. *Sleep Res* 24A:151, 1995.

Singer C, McArthur A, Hughes R, Sack R, Kaye J, Lewy A. Physiologic melatonin administration and sleep in the elderly. *Sleep Res* 24A:152, 1995.

Smythe GA, Lazarus L. Suppression of human growth hormone secretion by melatonin and cyroheptadine. *J Clin Invest* 54:116–121, 1974.

Smythe GA, Lazarus L. Growth hormone responses to melatonin in man. *Science* 184:1373–1374, 1975.

Starr KW. Growth and new growth: environmental carcinogens in the process of human ontogeny. In: Ariel IL. *Process in Clinical Cancer*. New York: Grune and Stratton, 1–29, 1970.

Strassman RJ, Pearle GT, Qualls CR, Lisansky EJ, A model for the study of the acute effects of melatonin in man. *J Clin Endocr Metab* 65:847–852, 1987.

Strassman R, Peake G, Qualls C, Lisansky E. Lack of an acute modulatory effect of melatonin on human nocturnal thyrotropin and cortisol secretion. *Neuroendocrinol* 48:387–393, 1988.

Strassman R, Qualls C, Lisansky E, Peake G, Elevated rectal temperature produced by all night bright light is reversed by melatonin infusion in men. *Journal of Applied Physiology* 71:2178–2182, 1991.

Terlo, L, Laudon M, Tarasch R, Caine YG, Zisapel N. Effects of short and long acting melatonin formulations on daytime sleep and mood. *Sleep Res* 24A:547, 1995.

Terzolo M, Piovesan A, Puligheddu B, Torta M, Osella G, Paccotti P, Angeli A. Effects of long–term, low–dose, time–specified melatonin administration on endocrine and cardiovascular variables in adult men. *J Pineal Res* 9:113–124, 1990.

Terzolo M, Piovesan A, Osella G, Torta M, Buniva T, Paccotti P, Wierdas T, Angeli A. Exogenous melatonin enhances the TRH–induced prolactin release in normally cycling women, a sex–specific effect. *Gynecological Endocrinology* 5:83–94, 1991.

Terzolo M, Revelli A, Guidetti D, Piovesan A, Cassoni P, Paccotti P, Angeli A, Massobrio M, Evening administration of melatonin enhances the pulsatile secretion of prolactin but not of LH and TSH in normally cycling women. *Clin Endocrinol (Oxf)* 39:185–191, 1993.

Tomada A, Miike T, Uezono K, Kawasaki T. A school refusal case with biological rhythm disturbance and melatonin therapy. *Brain and Development* 16:71–76, 1994.

Turow V. Melatonin for insomnia and jet lag [letter]. *Pediatrics* 97:439, 1996.

Tzischinsky O, Pal I, Epstein R, Dagen Y, Laview P. The importance of timing in melatonin administration in a blind man. *J Pineal Res* 12:105–108, 1992.

Tzischinsky O, Dagen Y, Lavie P. The effects of melatonin on the timing of sleep in patients with delayed sleep phase syndrome: In: Touitou Y, Arendt J, Pévet P. *Melatonin and the Pineal Gland–from Basic Science in Clinical Application*. New York: Elsevier, 351–354, 1993.

Tzinchinsky O, Lavie P. Melatonin possesses time–dependent hypnotic effects. *Sleep* 17:638–645, 1994.

Vakkuri O, Lappäluoto J, Kauppila A. Oral administration and distribution of melatonin in human serum, saliva and urine. *Life Sci* 37:489–495, 1985.

Valcavi R, Dieguez C, Azzarito C, Edwards CA, Dotti C, Page MD, Portioli I, Scanlon MF. Effect of oral administration of melatonin on GH responses to GRF 1–44 in normal subjects. *Clin Endocrinol (Oxf)* 26:453–8, 1987.

Valcavi R, Zini M, Maestroni GJ, Conti A, Portioli I. Melatonin stimulates growth hormone secretion throught pathways other than the growth hormone–releasing hormone. *Clin Endocrinol (Oxf)* 39:193–199, 1993.

van den Heuvel C, Dawson D. Melatonin: a neuroendocrine mediator of the circadian rhythms of temperature and sleep. *Sleep Res* 24A:550, 1995.

van den Heuval C, Kennaway D, Dawson D. Acute thermoregulatory effects of daytime melatonin infused at physiological levels: preliminary data in yound adults. *Sleep Res* 26:87, 1997.

Vollrath L, Semn P, Gammel G. Sleep induction by intranasal application of melatonin. In: Birau N, Schloot W. *Melatonin: Current Status and Perspectives. Advances in the Biosciences*. London: Pergamon Press, 327–329, 1981.

von Gizycki H, Jean–Louis G, Zizi F, Troia S, Franconeri S, Green H, Snyder M, Spielman A, Taub H. The effect of melatonin on performance in a visual vigilance task. *Sleep Res* 26:132, 1997.

Voordouw BCG, Euser R, Verdonk RER, Alberta BTH, De Jong FH, Drogendijk AC, Fauser BCJM, Cohen M. Melatonin and melatonin–progestin combinations alter pituitary–ovarian function in women and can inhibit ovulation. *J Clin Endocr Metab* 74:108–117, 1992.

Waldhauser F, Wurtman RJ. The secretion and actions of melatonin: In: Litwack G. *Biochemical Actions of Hormones*. San Diego: Academic Press, 187–225, 1983.

Waldhauser F, Waldhauser M, Liberman HR, Dent MH, Lynch HJ. Bioavailability of oral melatonin in humans. *Neuroendocrinol* 39:307–313, 1984.

Waldhauser F, Weiszenbacher G, Frisch H, Zeithuber U, Waldhauser M, Wurtman RJ. Fall in nocturnal serum melatonin during prepuberty and pubescence. *Lancet* i:362–365, 1984.

Waldhauser F, Lieberman HR, Lynch HJ, Waldhauser M, Herkner K, Frisch H, Vierhapper H, Waldhäusl W, Schemper M, Wurtman RJ. Crowley WF. A pharmacological dose of melatonin increases PRL levels in males without altering those GH, LH, FSH, TSH, testosterone or cortisol. *Neuroendocrinol* 46:125–130, 1987.

Waldhauser F, Steyer H, Vorkapic P. Melatonin secretion in man and the influence of exogenous melatonin on some physiological and behavioral variables. In: Reiter RJ, Fraschini F. *Advances in Pineal Research*. London: John Libbey, 207–221, 1987.

Waldhauser F, Saletu B, Trinchard–Lugan I. Sleep laboratory investigations on hypnotic properties of melatonin. *Psychopharmacology* 100:222–226, 1990.

Webley GE, Lenton EA. The temporal relationship between melatonin and prolactin in women. *Fertility and Sterility* 48:218–222, 1987.

Webley GE, Böhle A, Leidenberger FA. Positive relationship between the nocturnal concentrations of melatonin and prolactin, and a simulation of prolactin after melatonin administrations in young men. *J Pineal Res* 5:19–33, 1988.

Weinberg U, Weitzman E, Fukushima D, Cáncel G, Rosenfield R. Melatonin does not suppress the pituitary lutenizing hormone response to lutenizing releasing hormone in man. *J Clin Endocr Metab* 51:161–162, 1980.

Weinberg U, Weitzman ED, Horowitz ZD, Burg AC. Lack of an effect of melatonin on the basal and L–dopa stimulated growth hormone secretion in men. *J Nerual Trans* 52:117–121, 1981.

Wirz–Justice A, Kräuchi K, Cajochen C, Hetsch C, Möri D. The phase advance induced by evening melatonin administration is mediated by rapid modulation of thermoregulatory mechanisms. *Soc light Treatment Biol Rhythms Abst* 7:18, 1995.

Wright J, Aldous M, Franey C, English J, Arendt J. The effects of exogenous melatonin on endocrine function in man. *Clin Endocrinol (Oxf)* 24:375–382, 1986.

Wurtman RJ, Zhdanova I. Improvment of sleep quantity by melatonin [letter; comment]. *Lancet* 346:1491, 1995.

Wynn VT, Arendt J. Effect of melatonin on the human electrocardiogram and simple reaction time responses. *J Pineal Res* 5:427–435, 1988.

Young SN, Gauthier S, Kiely ME, Lal S, Brown GM. Effect of oral melatonin administration on melatonin, 5–hydroxyindoleacetic acid, indoleacetic acid, and cyclic nucleotides in human cerebrospinal fluid. *Neuroendocrinol* 39:87–92, 1984.

Young IM, Leone RM, Francis P, Stovell P, Silman RE. Melatonin is metabolized to N–acetyl serotonin and 6–hydroxymelatonin in man. *J Clin Endocr Metab* 60:114–119, 1985.

Zaidan R, Geoffriau M, Brun J, Taillard J, Bureau C, Chazot G. Alteration of the endogenous melatonin secretion by a single 4 a.m. or noon melatonin infusion in humans. Presented at the Programme & Abstracts from the 6$^{th}$ Colloquium of the European Pineal Society, The Panum Institute, UniveZizi F, Jean–Louis G, von Gizycki H, Spielma A, Stampi C, Nunes J, Frisina P, Taub H. Time–dependent soporific effects of exogenous melatonin as assessed by actigraphy. *Sleep Res* 26:137, 1997.rsity of Copenhagen, 1993.

Zhdanova IV, Wurtman RJ, Lynch HJ, Ives J, Matheson J, Morabito C, Dollins AB, Schomer DL, Watkins CJ. Evening admistration of melatonin promotes sleep in humans. *Soc Neurosci. Abs*. 20:1440, 1994.

Zhdanova IV, Wurtman RJ, Lynch HJ, Morabito C, Matheson J. Sleep–inducing effects of low melatonin doses. *Sleep Res* 24:66, 1995.

Zhdanova IV, Wurtman RJ, Lynch HJ, Ives JR, Dollins AB, Morabito C, Matheson JK, Schomer DL. Pharmacodynamics and drug actions. *Clin Pharmacol Ther* 57:552–558, 1995.

Zhdanova IV, Wurtman RJ, Morabito C, Piotrovska VR, Lynch HJ. Effects of low oral doses of melatonin, given 2–4 hours before habitual bedtime, on sleep in normal young humans. *Sleep* 19:423–431, 1996.

Zhdanova IV, Wurtman RJ, Balcioglu A, Lynch HJ. Endogenous and exogenous melatonin levels: age effects. *Sleep Res* 26:147, 1997.

Zizi F, Jean–Louis G, von Gizycki H, DiPalma J, Shemtov D, Spielman A, Taub H. Possible interaction of melatonin treatment with other sleep–inducing medications. *Sleep Res* 26:136, 1997.

Zizi F, Jean–Louis G, von Gizycki H, Spielman A, Stampi C, Nunes J, Francis P, Taub H. Time–dependent soporific effects of exogenous melatonin as assessed by actigraphy. *Sleep Res* 26:137, 1997.

Jan JE, Espezel H. Melatonin treatment of chronic sleep disorders [letter]. *Developmental Medicine & Child Neurology* 37:279–80, 1995.

Jean–Louis G, Zizi F, von Gizycki H, Spielman AJ, Stampi C, Friedman K, Nunes J, Taub H. The efficacy of melatonin on the sleep of normals as assessed by actigraphy. *Sleep Res* 25:59, 1996.

Kräuchi K, Cajochen C, Danilenko KV, Wirz–Justice A. The hypothermic effect of late evening melatonin does not block the phase delay induced by concurrent bright light. *Soc Light Treatment Biol Rhythms Abst* 9:12, 1997.

Leach C, Thorburn G. A comparison of the inhibitory effects of melatonin and indomethacin on platelet aggregation and thromboxane release. *Prostaglandins* 20:51–56, 1980.

Lerner AB, Case JC. Melatonin. *Federal Proceedings* 19:590–592, 1960.

Lewy AJ, Scak RL, Latham JM. Exogenous melatonin administration shifts circadian rhythms according to a phase response curve [Abstract 021]. In: The Vth Colloquium of the European Pineal Study Group. England: Guildford, 1990.

Lewy AJ, Sack RL, Latham JM. Circadian phase shifting of blind and sighted people with exogenous melatonin adminstration: evidence for a phase response curve. *Soc Light Treatment Biol Rhythms Abst* 2:22, 1990.

Lieberman HR, Wurtman RJ, Emde CC, Roberts C, Coviella ILG. The effects of low doses of caffeine on human performance and mood. *Psychopharmacology* 92:308–312, 1987.

Lisstoni P, Barni S, Tancini G, al. e. Clinical Study of melatonin in untreatable advanced cancer patients. *Tumori* 73:475–480, 1987.

Lisstoni P, Barni S, Crispino S, Tancini G, Fraschini F. Endoctrine and immune effects of melatonin therapy in metastic cancer patients. *Eur J Cancer Clin Oncol* 25:789–795, 1989.

Lissoni P, Barni S. Cazzaniga M, Ardizzoia A, Rovelli F, Brivio F, Tancini G. Efficacy of the concomitant administration of the pineal hormone melatonin in cancer immunotherapy with low–dose IL–2 in patients with advanced solid tumors who had progressed on IL–2 alone. *Oncology* 51:344–347, 1994

Matthews C, Kennaway D, Fellenberg AJG, Phillipou D, Cox LW, Seamark RF. Melatonin in man. *Adv biosci* 29:371–381, 1981.

Nordlund J, Lerner A. The effect or oral melatonin on skin color and on the release of pituitary hormones. *J Clin Endocr Metab* 45:768–774, 1997.

Okatani Y, Sagara Y. Role of melatonin in nocturnal prolactin secretion in women with normoprolactinemia and mild hyperprolactinemia. *American Journal of Obstetrics and Gynecology* 168:854–861, 1993.

Pavel S, Goldstein R, Petrescu M, Popa M. Melatonin, vasotocin, and REM sleep in prepuberal boys. In: Birau N, Schloot W. *Melatonin: Current Status and Perspectives. Advances in the Biosciences*, vol. 29. London: Pergamon Press, 343–347, 1981.

Reinhard U, Kendel K, Burmeister P, Böhme W, Cramer H. Melatonin. Influence on afternoon sleep pattern and plasma levels of human growth hormone and cyclic AMP in healthy volunteers. In: Levin P, Koells WP. *Sleep 1974*. Basel: Karger, S., 518–522, 1975.

Samuel A, Wegmann HM, Vejvoda M. Circadian adaptation after simulated time shifts–the effect of melatonin. *J Sleep Res* 1:205, 1992.

Sandyk R, Anastasiadis PG, Anninos PA, Tsagas N. Is postmenopausal osteoporosis related to pineal gland function? *Int J Neurosci* 62:215–225, 1992.

Sarrafzadeh A, Wirz–Justice A, Arendt J, English J. Melatonin improves sleep in a blind man. Presented at the $10^{th}$ Congress of the European Sleep Research Society, Strasbourg, 1990.

Smythe GA, Lazarus L. Suppression of human growth hormone secretion by melatonin and cyroheptadine. *J Clin Invest* 54: 116–121, 1974.

Smythe GA, Lazarus L. Growth hormone responses to melatonin in man. *Science* 184:1373–1374, 1975.

Starr KW. Growth and new growth: environmental carcinogens in the process of human ontogeny. In: Ariel IL. *Process in Clinical Cancer*. New York: Grune and Stratton, 1–29, 1970.

Strassman R, Peake G, Qualls C, Lisansky E. Lack of an acute modulatory effect of melatonin on human nocturnal thyrotropin and cortisol secretion. *Neuroendocrinol* 48:387–393, 1988.

Terzolo M, Piovesan A, Osella G, Torta M, Buniva T, Paccotti P, Wierdas T, Angeli A. Exogenous melatonin enhances the TRH–induced prolactin release in normally cycling women, a sex–specific effect. *Gynecological Endocrinology* 5:83–94, 1991.

Turow V. Melatonin for insomnia and jet lag [letter]. *Pediatrics* 97:439, 1996.

Tzischinsky O, Dagen Y, Lavie P. The effects of melatonin on the timing of sleep in patients with delayed sleep phase syndrome. In:Touitou Y, Arendt J, Pévet P. *Melatonin and the Pineal Gland–grom Basic Science to Clinical Application*. New York: Elsevier, 351–354, 1993.

Waldhauser F, Wurtman RJ. The secretion and actions of melatonin. In: Litwack G. *Biochemical Actions of Hormones*. San Diego: Academic Press, 187–225, 1983.

Waldhauser R, Weiszenbacher G, Frisch H, Zeithuber U, Waldhauser M, Wurtman RJ. Fall in nocturnal serum melatonin during prepuberty and pubescence. *Lancet* i:362–365, 1984.

Webley GE, Lenton EA. The temporal relationship between melatonin and prolactin in women. *Fertility and Sterility* 48:218–222, 1987.

Weble GE, Bühle A, Leidenberger FA. Positive relationship between the nocturnal concentrations of melatonin and prolactin, and a simulation of prolactin after melatonin administrations in young men. *J Pineal Res* 5:19–33, 1988.

Wynn VT, Arendt J. Effect of melatonin on the human electrocardiogram and simple reaction time responses. *J Pineal Res* 5:427–435, 1988.

Zaidan R, Geoffriau M, Brun J, Taillard J, Bureau C, Chazot G. Alteration of the endogenous melatonin secretion by a single 4 a.m. or noon melatonin infusion in humans: Presented at the Programme & Abstracts from the $6^{th}$ Colloquim of the European Pineal Society, The Panum Institute, UniveZizi F, Jean–Louis G, von Gizycki H, Spielman A, Stampi C, Nunes J, Frisina P, Taub H. Time–dependent soporific effects of exogenous melatonin as assessed by actigraphy. *Sleep Res* 26:137, 1997.rsity of Copenhagen, 1993.

Zhdanova IV, Wurtman RJ, Lynch HJ, Ives JR, Dollins AB, Morabito C, Matheson JK, Schomer DL. Pharmacodynamics and drug actions. *Clin Pharmacol Ther* 57:552–558, 1995.

Antón–Tay F, Chou C, S.A. Wurtman RJ. Brain serotonin concentration: elevation following intraperitoneal administrations of melatonin. *Science* 162:277–278, 1968.

Antón–Tay F. Melatonin. Effects on brain function: In: Costa E, Gessa GL, Sandler M. *Serotonin—New Vistas: Biochemistry and Behavioral and Clinical Studies. Advance in Biochemical Psychopharmacology*. New York: Raven Press, 315–324, 1974.

Bispink G. Zimmerman R, Weise HC, Leidenberger F. Influence of melatonin on the sleep–independent component of prolactin secretion. *J Pineal Res* 8:97–106, 1990.

Cajochen C, Kräuchi, K, Möri D, von Arx M, Wirz–Justice A. Melatonin increases sleepiness and theta activity in the wake EEG, but does not affect the sleep EEG except to lenghthen the first REM sleep episode. *Soc Light Treatment Biol Rhythms Abst* 7:19, 1995.

Cajochen C, Kräuchi K, Möri D, Hetch C, Wirz–Justice A. A single administration of melatonin or the melatonin agonist s–20098 lengthens the first REM sleep episode. *Sleep Res* 24:40, 1995.

Cajochen C, Kräuchi K, Danilenko KV, Renz C, Wirz–Justice A. Melatonin and bright light interactions on the waking EEG. *Sleep Res* 26:70, 1997.

Cajochen C, Kräuchi K, Hofstetter M, Renz C, Wirz–Justice A. The acute soporific action of melatonin on the waking EEG is attenuated by an orthostatic challenge. *Sleep Res* 26:71, 1997.

Carman JS, Post RM, Buswell R, Goodwin FK. Negative effects of melatonin on depression. *am J Psychiatry*133:1181–1186, 1976.

Claustrat B, Bars D, Brun J, Thivolle P, Mallo C, Arendt J, Chazot G. Plasma and brain pharmacokinetic studies after intravenous administration of cold or $^{11}$C labelled melatonin. In: Reiter R, Pang S. *Advances in Pineal Research*. London: John Libbey, 305–310, 1989.

Cotzias GC, Papavasiliou PS, Ginos J, al. e. Metabolic modification of Parkinson's disease and of chronic manganese poisoning. *Annual Rev Med* 22:305–326, 1971.

Dagen Y, Yovel I, Hallis D. Melatonin treatment of DSPS: a follow–up study. *Sleep Res* 26:349, 1997.

Dawson D, Gibbon S, Singh P. The hypothermic effect of melatonin on core body temperature: is more better: *J Pineal Res* 20:192–197, 1996.

English J, Aldhous M, Arendt J, Ravault JP, Wirz–Justice A. Direct radioimmunoassay of melatonin in human saliva [Abstract 139]. In: *The Vth Colloquim of the European Pineal Study Group*. England: Guildford, 1990.

Ferini–Strambi L, Zucconi M, Biella G, Oldani A, Stankov B, Fraschini F, Oldani A, Smirne S. Macro–and micro–structure of sleep after melatonin in healthy subjects. Presented at the 6th Annual Meeting of the Association of Professional Sleep Societies, Annual Meeting Abstracts, 1992.

Ferini–Strambi L, Zucconi M, Biella G, Stankov B, Fraschini F, Oldani A, Smirne S. Effect of melatonin on sleep microstructure: preliminary results in healthy subjects. *Sleep* 16:744–747, 1993.

Fernández–Guradiola A, Antón–Tay F. Modulation of subcortical inhibitory mechanisms by melatonin. In: Myers RD, Drucker–Colin RR. *Neurohumoral Coding of Brain Function*. New York: Plenum Press, 273–287, 1974.

METHODS FOR TREATING CIRCADIAN RHYTHM DISORDERS

This application is a continuation-in-part of U.S. Ser. No. 08/778,842, filed Jan. 6, 1997, now U.S. Pat. No. 6,069,164 which is a divisional of U.S. Ser. No. 08/110,878, filed Aug. 24, 1993, now U.S. Pat. No. 5,591,768, issued Jan. 7, 1997, which is a continuation-in-part of U.S. Ser. No. 08/077,426, filed Jun. 15, 1993, now U.S. Pat. No. 5,420,152, issued on May 30, 1995, which is a divisional of U.S. Ser. No. 07/842,723, filed Feb. 25, 1992, now U.S. Pat. No. 5,242,941, issued Sep. 7, 1993, which is a continuation of U.S. Ser. No. 07/621,866, filed on Dec. 4, 1990 and now abandoned.

This application is also a continuation-in-part of U.S. Ser. No. 08/779,797, filed Jan. 7, 1997, now abandoned, which is a continuation of U.S. Ser. No. 08/454,545, filed May 30, 1995, now U.S. Pat. No. 5,716,978 which is a divisional of U.S. Ser. No. 08/077,426, filed Jun. 15, 1993, now U.S. Pat. No. 5,420,152, issued on May 30, 1995, which is a divisional of U.S. Ser. No. 07/842,723, filed Feb. 25, 1992, now U.S. Pat. No. 5,242,941, issued Sep. 7, 1993, which is a continuation application of U.S. Ser. No. 07/621,866, filed on Dec. 4, 1990 and now abandoned.

This invention was made with government support under MH 40161 and MH 00703 awarded by the National Institutes of Health. The government has certain rights in the invention.

BACKGROUND OF THE INVENTION

1. Field of the Invention

This application relates to circadian rhythms in humans, and particularly to the synchronization of such human circadian rhythms with the external environment. Specifically, this invention describes methods for achieving a chronobiologic (circadian phase-shifting) effect in humans. The invention provides methods to specifically advance or delay the phase of certain circadian rhythms in humans. Specific embodiments of the invention comprise methods for alleviating the effects of transmeridional travel (i.e., jet lag); methods for alleviating certain circadian phase disturbance-based psychopathological disorders such as winter depression (or seasonal affective disorder); methods for achieving synchrony between a human's wake/sleep cycle or other circadian rhythms and the human's occupational and other human activity schedules; and methods for achieving synchrony between a human's wake/sleep cycle and other circadian rhythms.

2. Background of the Related Art

The phenomenon of circadian rhythms in biology is well known, and circadian rhythms are exhibited by all eukaryotic plants and animals, including man. Biological rhythms are periodic fluctuations in biological properties over time; these include circadian as well as seasonal variations. Circadian, or approximately 24-hour, rhythms include the production of biological molecules such as hormones, the regulation of body temperature, and behaviors such as wakefulness, sleep and periods of activity.

In nature, circadian rhythms are closely tied to environmental cues that impose a 24-hour pattern on many of these fluctuations. When these cues are absent, most circadian rhythms have a periodicity different (in humans, usually slightly greater) than 24 hours. Circadian rhythms that are no longer regulated by environmental cues are said to be free running. The regulation of circadian rhythms by signals from the environment is said to involve entrainment of circadian rhythms. The environmental signals that affect entrainment have been termed zeitgebers, an example of which is the light/dark cycle.

It is thought in this art that the control of circadian rhythms in mammals is mediated by a portion of the brain called the superchiasmatic nuclei (SCN). Circadian rhythms are primarily entrained by the light and dark cycle; light signals are conveyed by the retina to the SCN, and the pineal gland, which is regulated by the SCN, produces melatonin (N-acetyl-5-methoxytryptamine).

Disruption of circadian rhythms can result in a number of pathophysiological states in humans; one of the most common of these is jet lag. The use of melatonin to ameliorate the effects of jet lag has been described in the prior art.

U.S. Pat. Nos. 4,665,086 and 4,600,723 teach the use of melatonin to alleviate the symptoms of jet lag. These patents teach the use of >1 to 10 mg of melatonin, taken at destination bedtime, and again upon premature awakening in the middle of the night.

Gwinner and Benzinger, 1978, *J. Comp. Physiol.* 126: 123–129 teach that daily injections of melatonin can entrain the activity/rest cycle in birds.

Arendt et al., 1984, *Neurosci. Lett.* 45: 317–325 and Arendt et al., 1985, *CIBA Found. Symp.* 117: 266–283 disclose that melatoriin in high doses increases tiredness and the tendency to sleep in humans.

Underwood, 1986, *J. Pineal Res.* 3: 187–196 discloses a phase response curve for melatonin in the lizard *Sceloporus occidentalis*.

Arendt et al., 1987, *Ergonomics* 30: 1379–1393 disclose the administration of melatonin to alleviate jet lag by oral administration of exogenous melatonin 4 to 6 hours prior to the human's normal bedtime.

Mallo et al. 1988, *Acta Endocrinol.* 119: 474–480 teach that the administration of 8 mg of melatonin to humans, one hour before bedtime over a course of four days, results in a slight phase advance in the melatonin rhythm three days after cessation of the melatonin treatment but not in other circadian rhythms.

Armstrong et al., 1989, *Experientia* 45: 932–938 disclose the effects of exogenous melatonin administration on the circadian rhythm of the sleep/wake cycle in rats, and that the effect was greatest when exogenous melatonin was administered a few hours before the effective start of the nocturnal activity cycle.

Petrie et al., 1989, *Brit. Med. J.* 298: 705–707 teach the administration of 5 mg of melatonin to humans on a schedule of three days before flight, during flight, and once a day for three days after arrival to alleviate jet lag caused by flights from Auckland, New Zealand to London and back.

Skene et al., 1989, *Sleep '88* (J. Horne, ed.), pp. 39–41 teach the use of melatonin to treat jet lag.

Sack & Lewy, 1989, *Amer. Coll. Neuropsychopharm.* Abstract suggest the possibility of achieving a phase advance in a human using melatonin administered in the evening.

Samel et al., 1991, *J. Biol. Rhythms* 6: 235–248 teach the use of melatonin for the treatment of jet lag using an administration schedule of melatonin administration at 1800 local time for 3 days before the time shift, and at 1400 local time for 4 days afterwards.

Nichelsen et al., 1991, *Adv. Pineal Res.* 5: 303–306 teach the administration of 5 mg melatonin at destination bedtime for the treatment of jet lag resulting from 6, 9 and 11 hour time-shifts.

Dahlitz et al., 1991, *The Lancet* 337: 1121–1124 disclosethe use of melatonin to treat delayed sleep phase disorder.

Claustrat et al., 1992, *Biol. Psychiatry* 32: 705–711 teach the use of melatonin to affect circadian rhythms.

Sack et al., 1994, *Sleep Research* 23: 509 disclose melatonin administration to promote adaptation to shift work.

Zaidan et al., 1994, *Neuroendocrinol.* 60: 105–112 describe a melatonin phase response curve.

Deacon & Arendt, 1995, *Brain Res.* 688: 77–85 disclose dose-dependent phase-shifting effects with melatonin administration.

U.S. Pat. No. 5,449,683 issued Sep. 12, 1995 to Wurtman teaches the use of low dose melatonin formulations to induce sleep.

U.S. Pat. No. 5,498,423, issued Mar. 12, 1996 to Zisapel, teaches melatonin administration in formulations provided to mimic a human's endogenous nighttime melatonin profile.

Similarly, inhibition of endogenous melatonin production (using, for example, beta-blockers) for affecting human circadian rhythms have been reported in the prior art.

Schlager et al., 1993, *Soc. Light Treat. Biol. Rhythms Abstracts* 5: 23 teach early morning administration of short-acting beta-blockers for treatment of winter depression.

Schlager, 1994, *Amer. J. Psych.* 151: 1383–1385 teach early morning administration of short-acting beta-blockers for treatment of winter depression.

Schlager et al., 1996, *Soc. Light Treat. Biol. Rhythms Abstracts* #15 teach early morning administration of short-acting beta-blockers for treatment of winter depression.

The use of light to entrain circadian rhythms is known in the prior art.

Lewy et al, 1983, *Psychopharmacol. Bull.* 19: 523–525 disclose a phase response curve to light in humans and bright light treatment of delayed sleep phase syndrome.

Waver et al., 1983, *Eur. J. Physiol.* 396: 85–87 disclose light for resetting human temperature and activity rhythms.

Daan & Lewy, 1984, *Psychopharmacol. Bull.* 20: 566–568 disclose a phase response curve to light in humans and treatment of jet lag by scheduled exposure to light.

Lewy et al, 1985, in *Photoperiodism, Melatonin and the Pineal Gland* (Evered et al., eds.), pp. 231–252 disclose bright light treatment of advanced sleep phase syndrome.

Czeisler et al., 1986, *Science* 233: 667–671 disclose light for resetting the circadian rhythm pacemaker.

Lewy et al, 1987, *Science* 235:352–354 disclose circadian phase-shifting and antidepressant effects of light treatment Eastman, 1987, *Temporal Disorder in Human Oscillatory Systems*, (Rensing et al., eds.) discloses light to promote adaptation to shift work.

Honma & Honma, 1988, *Jap. J. Psychiatry Neurol.* 42: 167–168 disclose a light phase response curve in humans.

Wever, 1989, *J. Biol. Rhythms* 4: 161–186 disclose a light phase response curve in humans.

Czeisler et al., 1989, *Science* 244:–1328–1333 disclose a light phase response curve in humans.

Hoban et al, 1989, *Chronobiol. Intl.* 6: 347–353 disclose the use of bright light treatment upon awakening to entrain a single sighted subject's circadian rhythm.

Minors et al., 1991, *Neurosci. Lett.* 133: 36–40 disclose a light phase response curve in humans.

U.S. Pat. No. 5,163,426, issued Nov. 17, 1992 to Czeisler et al., discloses the use of bright light to affect circadian rhythms.

U.S. Pat. No. 5,167,228, issued Dec. 1, 1992 to Czeisler et al., discloses the use of bright light to affect circadian rhythms.

U.S. Pat. No. 5,176,133, issued Jan. 5, 1993 to Czeisler et al., discloses the use of bright light to affect circadian rhythms.

U.S. Pat. No. 5,304,212, issued Apr. 19, 1994 to Czeisler et al., discloses the use of bright light to affect circadian rhythms.

Eastman et al., 1994, *Sleep* 17: 535–543 disclose light exposure regulatory regimens for promoting adaptation to shift work.

McArthur et al, 1996, *Sleep* 19: 544–553 disclose the use of melatonin to entrain human circadian rhythms.

U.S. Pat. No. 5,503,637, issued Apr. 2, 1996 to Kyricos et al., disclose an apparatus for delivering bright light to a human to affect circadian rhythms.

U.S. Pat. No. 5,545,192, issued Aug. 13, 1996 to Czeisler et al., disclose the use of bright light to affect circadian rhythms.

Entrainment and regulation of circadian rhythms have been demonstrated in a number of animal species. The ability to effect an actual change in the phase of circadian rhythms would be useful for the alleviation of a number of circadian-rhythm related disorders.

U.S. Pat. No. 5,242,941, issued Sep. 7, 1993 and U.S. Pat. No. 5,420,152, issued May 30, 1995, both issued to the present inventors, were the first to disclose a phase response curve for melatonin in humans. These references taught that an appropriate time to administer melatonin to induce a change in phase of human circadian rhythms is related to the time of dim light melatonin onset (DLMO), a robust marker of a human's circadian rhythms. Contrary to the teachings of the prior art (that melatonin was simply associated with darkness, which came to be thought of as being equivalent to sleep in diurnal animals), the teachings of these patents established that the circadian rhythm of endogenous melatonin production was tightly coupled to the endogenous circadian pacemaker that regulates the timing of a variety of other human circadian rhythms (such as core body temperature, cortisol and sleep propensity), and that affecting the phase of the human melatonin circadian rhythm by administration of exogenous melatonin could effect both phase advances and phase delays in other human circadian rhythms. These patents disclosed that the magnitude and direction (i.e., phase advance or phase delay) of the desired circadian rhythm phase shift was dependent on the time of melatonin administration. Contrary to the established teachings of the prior art, these patents prescribed administration of relatively non-soporific (<1 mg) dosages of melatonin at times that usually were not equivalent to destination bedtime, based on the human melatonin phase response curve (PRC). The teachings of these patents are hereby expressly incorporated by reference.

U.S. Pat. No. 5,591,768, issued Jan. 7, 1997 to the present inventors, disclosed methods of administering exogenous melatonin at different clock times over a course of melatonin treatment, wherein melatonin administration was kept at a constant time relative to the dim light melatonin onset (DLMO) time. In this patent, the present inventors disclosed the use of administration regimes holding the time of melatonin administration constant relative to DLMO time for achieving both phase advances and phase delays of the melatonin phase response curve, for alleviating circadian rhythm disorders including jet lag, winter depression, shift work desynchronies, and sleep disorders. The teachings of this patent are hereby expressly incorporated by reference.

The human melatonin PRC described in U.S. Pat. Nos. 5,242,941 and 5,420,152 suggested that exogenous melatonin would be most effective when administered during the light period, to compete with light as a "substitute" for darkness. The human melatonin PRC clearly shows that melatonin acts like darkness on the endogenous circadian pacemaker(s) in humans. The circadian rhythm of melatonin production has an active phase of about 12 hours (levels reaching from a few picograms per mL of plasma to as great as several hundred picograms per mL, depending on the individual) and a quiescent phase of about 12 hours (levels falling to about 10 pg/mL or lower, depending on the individual and sensitivity of the melatonin assay). In entrained, sighted individuals, melatonin is produced only during nighttime darkness and not during daytime darkness, suggesting that melatonin may act by helping the endogenous circadian pacemaker to discriminate between the nighttime dark period and sporadic episodes of daytime darkness (including daytime sleep). Melatonin in combination with dim light or darkness thus might be a more effective darkness zeitgeber than darkness alone in the absence of melatonin. Aside from its effect on causing the human to perceive darkness, sleep alone has been found to have little, if any, chronobiologic effect in humans; however, it is possible that sleep may have a slight effect in potentiating the phase-shifting effects of melatonin and darkness.

SUMMARY OF THE INVENTION

This invention relates to a method for achieving a chronobiologic (phase-shifting) effect in a human by regulation of a human's circadian rhythms. Specifically, the circadian phase-shifting effect is achieved by the administration of exogenous melatonin. The methods of the invention produce phase shifting of circadian rhythms by administration of exogenous melatonin, wherein the term "melatonin" is intended to encompass melatonin itself and other circadian rhythm phase-shifting compounds that increase-endogenous melatonin levels or act on melatonin receptors, the term "melatonin levels" is intended to encompass levels, particularly plasma melatonin concentration levels, of melatonin itself and melatonin agonists, and the term "quiescent melatonin levels" is intended to encompass melatonin itself and equivalent agonists, as all of these terms are described herein (see the Detailed Description of Preferred Embodiments). Further, the methods of the invention relate to the timing of melatonin administration to the human. The methods described herein are used to advance or delay the phase of circadian rhythms in a human. This effect is advantageously achieved by administering exogenous melatonin to the human at an appropriate time relative to the human's endogenous melatonin onset and offset times. In this way, the present invention is able to alleviate jet lag and other circadian rhythm disorders of both the phase-delay and the phase-advance types.

In one aspect of the invention is provided a method for achieving a circadian rhythm phase-shifting effect in a human, the method comprising administering to the human an amount of melatonin, said administration producing in the human a plasma melatonin concentration of greater than quiescent melatonin levels. The timing of plasma melatonin concentrations greater than quiescent melatonin levels overlaps with either the onset of endogenous melatonin production in the human (to cause a phase advance) or the offset of endogenous melatonin production in the human (to cause a phase delay). Thus, in one embodiment of the invention is provided a method for causing a circadian rhythm phase-shifting effect that is a phase advance, wherein the time of plasma melatonin concentration of greater than quiescent melatonin levels overlaps with the onset of endogenous melatonin production in the human. In this embodiment, melatonin is administered to the human in an immediate-release formulation before about circadian time (CT) 14, preferably after about CT 6, and levels continue past the time of endogenous melatonin onset (CT 14 is the time of an individual's dim light endogenous melatonin onset, termed DLMO, which is defined and described in detail herein). Alternatively, exogenous melatonin is administered to a human in a delayed-release formulation at a time wherein plasma melatonin concentration in the human is increased to greater than quiescent levels before about CT 14, preferably after about CT 6. Alternatively, exogenous melatonin is administered to a human in a sustained-release formulation before about CT 14, preferably in a formulation having a duration of less than about 12 hours, and preferably after about CT 6 to continue past the time of endogenous melatonin onset. According to the methods of the invention, the duration of the exogenous melatonin pulse, as defined herein, is sufficient to overlap the endogenous melatonin onset time for any of these different types of administered formulations, and preferably does not overlap the endogenous melatonin offset time.

In another embodiment, the invention provides a method for causing a circadian rhythm phase-shifting effect that is a phase delay, wherein the time of plasma melatonin concentration of greater than quiescent melatonin levels overlaps with the offset of endogenous melatonin production in the human. In a preferred embodiment, exogenous melatonin is administered to a human in an immediate-release formulation before about CT 1, preferably after about CT 18. Alternatively, exogenous melatonin is administered to a human in a delayed-release melatonin formulation at a time wherein plasma melatonin concentration in the human is increased to greater than quiescent levels before about CT 1 preferably after about CT 18. Alternatively, exogenous melatonin is administered in a sustained-release formulation before about CT 1, preferably in a formulation having a duration of less than about 19 hours, and preferably at about CT 18, wherein the plasma melatonin concentration returns to quiescent levels before the next night's endogenous melatonin onset. According to the methods of the invention, the duration of the exogenous melatonin pulse, as defined herein, is sufficient to overlap the endogenous melatonin offset time (typically, from CT 0 to CT 1) for any of these different types of administered formulations and preferably does not overlap the endogenous melatonin onset time.

In another aspect, the invention provides a method for achieving a circadian rhythm phase-shifting effect in a human, the method comprising administering to the human an amount of melatonin wherein said administration produces in the human a plasma melatonin concentration of greater than quiescent melatonin levels for a duration that coincides at least in part with either the phase advance zone (about CT 6 to about CT 18) or phase delay zone (about CT 18 to about CT 6) of the human melatonin phase response curve. In a first embodiment of this aspect of the invention, the circadian rhythm phase-shifting effect is a phase advance and exogenous melatonin is administered in a formulation having a duration to provide a period of plasma melatonin concentration greater than quiescent melatonin levels within the interval from about CT 6 to about CT 18. In a second embodiment of this aspect of the invention, the circadian rhythm phase-shifting effect is a phase delay and exogenous melatonin is administered in a formulation having a duration to provide a period of plasma melatonin concentration greater than quiescent levels within the interval from about CT 18 to about CT 6. Melatonin administration for achieving a phase advance advantageously is performed using a melatonin formulation having a duration of elevated plasma melatonin concentration that provides maximum stimulation of the phase-advance portion of the phase response curve (about CT 6 to about CT 18) while avoiding stimulation of the phase-delay portion of the phase response curve (about CT 18 to about CT 6), that is, having a maximum duration of about 12 hours. Melatonin administration for achieving a phase delay advantageously is performed using, a melatonin formulation having a duration of elevated plasma-melatonin concentration that provides maximum stimulation of the phase-delay portion of the phase response curve (about CT 18 to about CT 6) while avoiding stimulation of the phase-advance portion of the phase response curve (about CT 6 to about CT 18). However, it is also advantageous both to stimulate the maximum amount of the phase-delay portion of the phase response curve, and to provide for the longest duration of elevated plasma melatonin concentration after the endogenous melatonin offset (at about CT 1) without overlapping the time of endogenous melatonin onset. Thus, for achieving a phase delay, melatonin is advantageously administered having a maximum duration of about 19 hours (i.e., from about CT 18 to about CT 13). For phase advances, exogenous melatonin administration produces in the human a plasma melatonin concentration of greater than quiescent melatonin levels for a time or in a concentration during a time interval from about CT 6 to about CT 18 that is greater than that produced during the time interval from about CT 18 to about CT 6. For phase delays, exogenous melatonin administration produces in the human a plasma melatonin concentration of greater than quiescent melatonin levels for a time or in a concentration during a time interval from about CT 18 to about CT 6 that is greater than that produced during the time interval from about CT 6 to about CT 18.

The invention also provides a method for achieving a circadian rhythm phase-shifting effect in a human, the method comprising regulating exposure of the human to light, preferably sufficiently bright light to suppress endogenous melatonin production. In one embodiment of this aspect of the invention, the phase-shifting effect is a phase delay, the method comprising exposing the human to light for a time from about CT 6 to about CT 18. In a preferred embodiment, the human is subjected to light exposure at a time from about CT 14 to about CT 18. In another embodiment, the phase-shifting effect is a phase advance, and the method comprises subjecting the human to light exposure at a time from about CT 18 to about CT 6. In a preferred embodiment, the human is subjected to light exposure at a time from about CT 18 to about CT 1.

The invention also provides a method for achieving a circadian rhythm phase-shifting effect in a human, the method comprising regulating exposure of the human to light, wherein the human is subjected to darkness or dim light, or by limiting light exposure, for example, by prescribing the use of dark or red-colored goggles or other means to prevent a human from exposure to a light stimulus. In one embodiment of this aspect of the invention, the phase-shifting effect is a phase advance, the method comprising subjecting the human to darkness or dim light from about CT 6 to about CT 18. In a preferred embodiment, the human is subjected to darkness or dim light from about CT 14 to about CT 18. In another embodiment of this aspect, the invention provides a method for achieving a circadian rhythm phase delay, the method comprising regulating exposure of the human to darkness or dim light from about CT 18 to about CT 6. In a preferred embodiment, the human is subjected to darkness or dim light from about CT 18 to about CT 1.

Also contemplated as components of the methods of the instant invention are embodiments wherein melatonin administration is accompanied, either at times coincident with melatonin administration times by reducing exposure to artificial or natural light (i.e., providing darkness), or at appropriate times other than melatonin administration times, by exposure of a human to light, either artificial or naturally-occurring. Appropriate combinations of exogenous melatonin administration, dim light or bright light treatments are provided by this invention, as described more fully in the Examples below.

In another aspect of the invention is provided a method for achieving a circadian rhythm phase-shifting effect in a human, the method comprising administering to the human an amount of a melatonin antagonist or inverse agonist. In these embodiments of the methods of the invention, melatonin antagonist or inverse agonist is administered at a time to produce preferred stimulation of either the advance or delay zone of the melatonin PRC, or to provide an overlap between the time of plasma concentration levels of the melatonin antagonist or inverse agonist either the onset of endogenous melatonin production in the human (to cause a phase delay) or the offset of endogenous melatonin production in the human (to cause a phase advance).

Thus, in one embodiment of this aspect of the invention is provided a method for causing a circadian rhythm phase-shifting effect that is a phase delay, wherein the time of plasma concentration of the melatonin antagonist or inverse agonist overlaps with the onset of endogenous melatonin production in the human. In this embodiment, melatonin is administered to the human in an immediate-release formulation before about circadian time (CT) 14, preferably after about CT 6, and that levels continue past the time of endogenous melatonin onset. Alternatively, a melatonin antagonist or inverse agonists is administered to a human in a delayed-release formulation before about CT 1, preferably after about CT 6. Alternatively, melatonin antagonists or inverse agonists are administered to a human in a sustained-release formulation before about CT 14, preferably in a formulation having a duration of less than about 12 hours, and preferably after about CT 6 to continue past the time of endogenous melatonin offset. According to the methods of the invention, the duration of the pulse of melatonin antagonist or inverse agonist, as defined herein, is sufficient to overlap the endogenous melatonin onset time for any of these different types of administered formulations.

In another embodiment, the invention provides a method for causing a circadian rhythm phase-shifting effect that is a phase advance, wherein the time of plasma concentration of the melatonin antagonist or inverse agonist overlaps with the offset of endogenous melatonin production in the human. In a preferred embodiment, a melatonin antagonist or inverse agonist is administered to a human in an immediate-release formulation before about CT 1, preferably after about CT 18. Alternatively, melatonin antagonists or inverse agonists are administered to a human in a delayed-release melatonin formulation at a time before about CT 1, preferably after about CT 18. Alternatively, melatonin antagonists or inverse agonists are administered in a sustained-release formulation before about CT 1, preferably in a formulation having a duration of less than about 19 hours, and preferably after about CT 18, wherein the plasma concentration levels of melatonin antagonist or inverse agonist decrease to pretreatment levels before the next night's endogenous melatonin onset. According to the methods of the invention, the duration of the exogenous pulse of melatonin antagonist or inverse agonist, as defined herein, is sufficient to overlap the endogenous melatonin offset time (typically, from CT 0 to CT 1) for any of these different types of administered formulations and preferably does not overlap the endogenous melatonin onset time (DLMO).

In another embodiment of this aspect of the present invention, melatonin antagonist or inverse agonist is administered at a time wherein said administration produces in the human a plasma concentration of melatonin antagonist or inverse agonist for a time or in a concentration during a time interval from about CT 6 to about CT 18 that is greater than that produced during the time interval from about CT 18 to about CT 6, to provide a phase delay. For a phase advance, melatonin antagonist or inverse agonist is administered at a time wherein said administration produces in the human a plasma concentration of melatonin antagonist or inverse agonist for a time or in a concentration during a time interval from about CT 18 to about CT 6 that is greater than that produced during the time interval from about CT 6 to about CT 18, to produce a phase advance.

In another embodiment, the invention provides a method for achieving a circadian rhythm phase-shifting effect in a human, the method comprising administering to the human an amount of a compound that decreases endogenous production of melatonin in the human wherein said administration reduces endogenous plasma melatonin concentration in the human to a plasma concentration for a duration of time that is co-incident with a portion of the profile of endogenous melatonin production. In one embodiment of the method of the invention, the circadian rhythm phase-shifting effect is a phase advance and the duration of the effect of administration of a compound that decreases endogenous production of melatonin in the human on plasma melatonin concentration is from about CT 18 to about CT 1. In another embodiment, the circadian rhythm phase-shifting effect is a phase delay and the duration of the effect of administration a compound that decreases endogenous production of melatonin in the human on plasma melatonin concentration is from about CT 14 to about CT 18. In preferred embodiments, the administered melatonin reducing compound is a beta-blocker.

The invention also provides methods for administering melatonin to a human without causing a circadian rhythm phase-shifting effect. In this aspect, the invention provides a method of administering melatonin to a human without causing a phase shift in the human's circadian rhythms. The inventive methods comprise administering melatonin to a human wherein said administration produces in the human a plasma melatonin concentration of greater than quiescent melatonin levels wherein the duration of elevated plasma concentration greater than quiescent levels overlaps equally with both the onset time and offset time of endogenous melatonin production in the human. In an alternative embodiment of this aspect of the invention, melatonin is administered wherein said administration produces in the human a plasma melatonin concentration of greater than quiescent melatonin levels where in the duration of elevated plasma concentration coincides with equal portions of the phase advance and phase delay zones of the human's phase response curve.

Thus, in one embodiment of this aspect of the invention is provided a method comprising the step of administering to the human melatonin wherein said administration produces in the human a plasma melatonin concentration of greater than quiescent melatonin levels for a time wherein the rise of exogenous melatonin is about as many hours earlier than the onset as the fall of exogenous melatonin is later than the offset of the human's pre-treatment endogenous melatonin profile. In another embodiment, the invention provides a method comprising administering to the human melatonin wherein said administration produces in the human a plasma melatonin concentration of greater than quiescent melatonin levels for a time wherein the time of plasma melatonin concentration levels of greater than quiescent melatonin levels is co-incident with an equal portion of the phase advance and the phase delay zones of the individual's melatonin phase response curve.

Methods for administering melatonin antagonists, inverse agonists and compounds that reduce endogenous melatonin production in a human that do not produce a phase shift are also provided by the invention. In one embodiment of this aspect of the invention, the method comprises administering to the human a melatonin antagonist, inverse agonist or a compound that reduces melatonin production in a human, wherein said administration produces a plasma concentration of melatonin antagonist, inverse agonist or a compound that reduces melatonin production in a human for a time co-incident with equal portions of the phase advance and phase delay zones of the individual's melatonin phase response curve. In another embodiment, the method comprises administering to the human a melatonin antagonist, inverse agonist or a compound that reduces melatonin production in a human, wherein said administration produces a plasma concentration of melatonin antagonist, inverse agonist or a compound that reduces melatonin production in a human for a time wherein the rise of plasma concentration of melatonin antagonist, inverse agonist or a compound that reduces melatonin production in a human is about as many hours earlier than the onset as the fall of plasma concentration of melatonin antagonist, inverse agonist or a compound that reduces melatonin production in a human is later than the offset of the human's pre-treatment endogenous melatonin profile.

The methods of the invention are advantageously provided to alleviate a circadian rhythm-associated disorder in a human. In preferred embodiments, the circadian rhythm-associated disorder is jet lag, winter depression, shift-work related desynchronies or sleep disorders.

Specific preferred embodiments of the present invention will become evident from the following more detailed description of certain preferred embodiments and the claims.

DETAILED DESCRIPTION OF THE PREFERRED EMBODIMENTS

Figure 1:
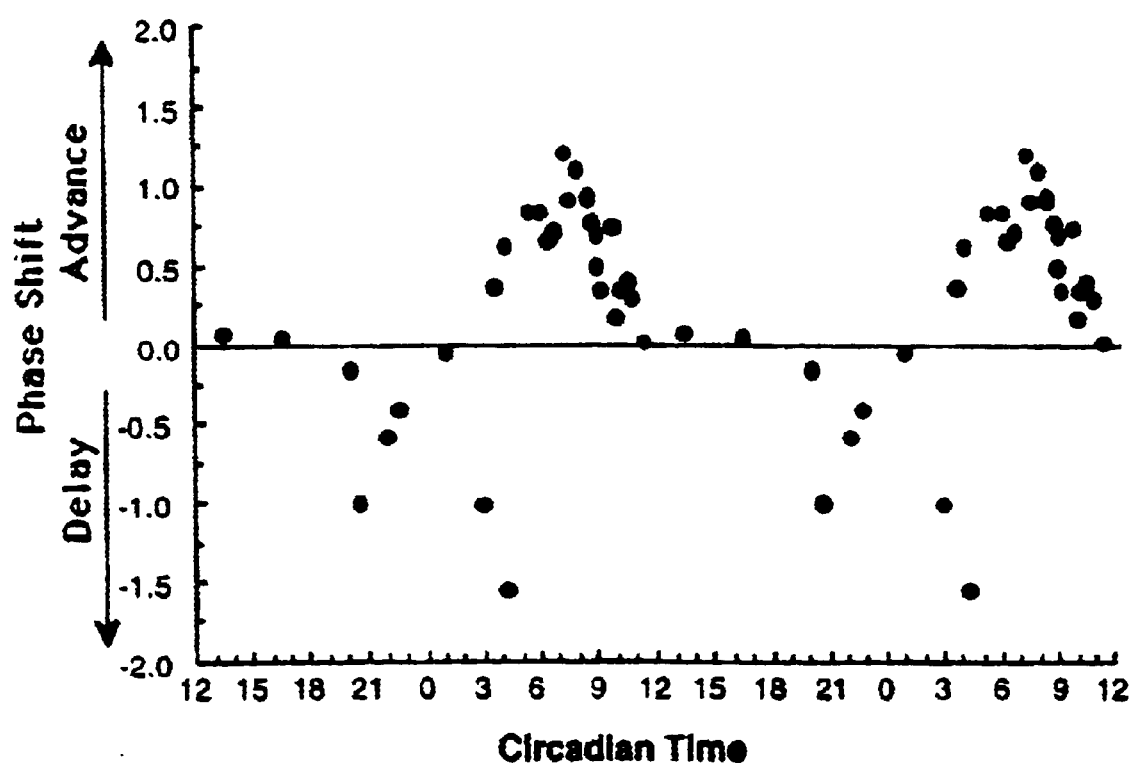
FIG. 1 illustrates circadian rhythm phase shifts in the melatonin PRC for 9 subjects who participated in melatonin phase response curve trials as described in Example 2.

The methods of this invention utilize enhancement and reduction of stimulation of the human melatonin phase response curve to produce a circadian-rhythm phase shift in a human. The methods of this invention prescribe particular exogenous melatonin administration and duration times during a course of exogenous melatonin treatment to effect a circadian rhythm phase shift. Exogenous melatonin administration times are prescribed according to the invention relative to an internal circadian rhythm marker, the DLMO time, rather than external markers such as destination bedtime (although administration times can be given as clock times that relate to known or estimated DLMO times). The invention thereby provides methods for achieving circadian rhythm phase-shifting effects that result in the effective treatment of a variety of circadian rhythm phase disturbances, including jet lag, winter depression, sleep disorders, shift-work and other human activity schedule-related disorders and desynchronies with external zeitgebers.

The present invention contemplates the administration of various doses of melatonin which promote quantitative shifts in an individual's endogenous circadian pacemaker. The administration of sufficient doses of melatonin is capable of shifting the endogenous circadian pacemaker, as well as the melatonin PRC, by an appropriate degree. A linear dose effect has been found as described herein and in U.S. Pat. Nos. 5,242,941 and 5,420,152, incorporated by reference, at melatonin dosages from about 0.125 mg to about 0.5 mg melatonin. The amount of melatonin administered to a human subject should be sufficient to achieve the desired circadian rhythm phase-shifting effect. In a preferred embodiment of this invention, a dosage of about 0.01 mg to about 100 mg, more preferably about 0.1 mg to about 10 mg, most preferably about 0.1 mg to about 1 mg, of exogenous melatonin is used to effect the desired change in phase of the circadian rhythm of endogenous melatonin production. For the purposes of this invention, the term "exogenously administered melatonin" encompasses various formulations of melatonin, melatonin agonists (that is, compounds that mimic melatonin's actions) and compounds that raise endogenous melatoriin levels. Therefore, whenever reference is made to increasing plasma melatonin levels due to administration of exogenous melatonin, this refers also to increasing plasma melatonin levels due to administration of a melatonin stimulant and increasing equivalent agonist levels due to administration of a melatonin agonist. In the latter case, when plasma levels of melatonin are referred to following a melatonin agonist, these melatonin levels are meant to be equivalent to levels of the melatonin agonist.

Pharmaceutical quality melatonin is commercially available. Since melatonin appears to be absorbed across almost all tissues, many routes of administration are possible. These include but are not limited to submucosal, sublingual, intranasal, ocular cul-de-sac, rectal, transdermal, buccal, intravenous, intramuscular, and subcutaneous methods of administration. A variety of administration means, including but not limited to capsules, tablets, suppositories, repositories, injections, transdermal or transbuccal patches or any reservoir capable of containing and dispensing melatonin, are also useful. In a preferred embodiment of this invention, melatonin is administered orally.

It may be advantageous to administer melatonin in immediate-release formulations, in formulations wherein the melatonin is continuously released physiologically for a set time (sustained-release formulations), or in formulations wherein the physiological release of melatonin is delayed (delayed-release formulations), or in combinations thereof. The present invention encompasses the use of such melatonin formulations in the methods of the instant invention.

The present invention contemplates the use of melatonin precursors, agonists and other compounds which mimic melatonin activity, in place of melatonin (N-acetyl-5-hydroxytryptamine) itself, as well as compounds that compete with melatonin at the melatonin receptor (melatonin antagonists) and compounds that stimulate melatonin receptors to have an effect opposite to that of melatonin (melatonin inverse agonists), in addition to drugs (melatonin blockers or melatonin stimulants) and interventions (such as exposure to light or darkness) that lower or raise, respectively, endogenous melatonin levels. For the purposes of this invention, the use of the term "melatonin" will also be understood to encompass all such melatonin agonists, precursors and other compounds that mimic melatonin activity, as well as compounds that increase endogenous melatonin production in the human or otherwise potentiate or enhance the physiological activity of melatonin in a human.

Further, the methods of the invention relate to the timing of the administration of the dosage, of melatonin and these other agents to the human. The timing of these agents in the human as described results in a specific phase shift (phase advance or phase delay) in the human's circadian rhythms.

The present invention is based on the melatonin phase response curve (PRC; see U.S. Pat. No. 5,242,941 and Example 2 below). The human melatonin PRC, shown in FIG. 1, indicates the presence of a time interval for each individual during which administration of exogenous melatonin results in clear and unequivocal phase-shifting responses. Within this interval, the time of administration of melatonin is related to the magnitude of the resulting phase shift of the PRC. The human melatonin PRC indicates the presence of time intervals for each individual during which administration of exogenous melatonin results in clear and unequivocal phase-shifting responses of the phase-advance and phase-delay types.

Melatonin administration as disclosed herein is achieved using melatonin formulations that increase plasma melatonin levels above quiescent levels present in a human during the day. For the purposes of this invention, the term "quiescent levels" and "quiescent melatonin levels" used with regard to endogenous melatonin plasma concentrations is intended to describe plasma melatonin levels that range from about 1 to about 10 pg/mL, depending on the individual and on the sensitivity of the melatonin assay, and which typically occur during the day in humans.

The existence of the DLMO provides for rendering the human melatonin phase response curve in terms of circadian time (designated CT) as well as clock time. Circadian time can be determined, for example, relative to at least two events: under entrained (steady-state) conditions, the first sufficiently bright light exposure after awakening, designated as CT 0; and the DLMO time, which is a physiologically-determined event that varies among individuals but typically occurs about 14 hours (CT 14) after first sufficiently bright light exposure after awakening. It will be understood that for most individuals, CT 0 is equivalent to wake-up time, but that some people awaken to darkness and do not receive sufficient light exposure until some time after awakening, which is CT 0 for these individuals.

In preferred embodiments of this invention, phase advances or phase delays in circadian rhythms can be effected by administration of an amount of exogenous melatonin based on any one of the following measures of the human's circadian rhythms: the individual's melatonin phase response curve, either actually measured or predicted; the individual's actual or estimated DLMO time, relative to other markers such as the individual's wake-up time (taken to be CT 0); or other circadian markers (such body core temperature, sleep onset times, and cortisol production) that can reasonably predict the phase relationships of the DLMO or the endogenous circadian pacemaker. Circadian time (CT) can be translated to clock times for ease of consumer or other use of the methods of the invention.

A modification of the method of Lewy and Markey (1978, Science 201: 741–3) is advantageously used to determine the time of onset of the patient's endogenous melatonin production, and can also be used to establish the individual's melatonin PRC. The preferred use of this method is taught in Example 1.

DLMO times are expected to vary from person to person. The most convenient method of estimating circadian times are relative to "sleep offset," defined as CT 0 and equal to the time of first sufficiently bright light exposure upon awakening. DLMO typically occurs 14 hours after such early morning light exposure, i.e. at CT 14. For example, for an individual who awakens at 7 a.m., DLMO time is typically 9 p.m. Thus, if the actual DLMO time is not determined as disclosed in Example 1, it can be estimated to be at about 9 p.m. for an individual who awakens at about 7 a.m, or 14 hours after the clock time of first sufficiently bright light exposure after awakening. Administration times given as circadian time can then be converted into clock times accordingly.

Determination of circadian time is done optimally using the DLMO time. However, in some individuals who have very low melatonin production (encompassing less than about 10% of the population), the DLMO will occur at slightly later times than CT 14, so that determination of the entire melatonin curve may be preferable in these low melatonin producers. Alternatively, DLMO time can be calculated as the time when a percent (e.g., about 25%) of peak endogenous production has been achieved, and the estimate of the DLMO's circadian time adjusted accordingly.

Markers for circadian time other than DLMO are also useful, for example sleep onset (bedtime), and in some cases these markers are more convenient than the DLMO time. There are also other physiological markers that may be used, including but not limited to the core body temperature minimum or the rising limb of the cortisol circadian rhythm. Preferred markers are markers that are tightly coupled to the endogenous circadian pacemaker (such as the DLMO), whereas other, less preferred markers such as the sleep rhythm (which may be influenced by social cues and other homeostatic factors) are somewhat less tightly coupled (although the sleep propensity rhythm is tightly coupled).

For the purposes of this invention, the increase in plasma melatonin or melatonin agonist concentration in a human resulting from administration of exogenous melatonin, melatonin agonist or compound used to stimulate endogenous melatonin production is termed the melatonin pulse; the time of the beginning of the pulse is termed the melatonin rise and the time of the end of the pulse is termed the melatonin fall. These terms are used to distinguish between the increase in plasma melatonin concentrations in a human resulting from pre-treatment endogenous production of melatonin, herein termed the melatonin profile, the time of the beginning of the profile is termed the melatonin onset, and the time of the end of the profile is termed the pretreatment endogenous offset. The threshold levels used to discern these times are typically about 10 pg/mL. In some individuals, specifically those termed "very low secretors," this threshold is decreased to about 1 pg/mL (or even less in some individuals). It is recognized that, as assay methodology improves, this lower threshold may be used more frequently, and could be even lower than these thresholds. For the purposes of this invention, melatonin onset and offset times are determined relative to plasma melatonin concentration levels of about 1–10 pg/mL; this range encompasses daytime (quiescent) melatonin levels in virtually all individuals.

The present invention provides methods for achieving a circadian rhythm phase-shifting effect whereby exogenous melatonin is administered co-incident with at least a portion of the phase advance or phase delay zone of the melatonin phase response curve to provide a phase advance or a phase delay, respectively. This invention provides for exogenous melatonin having a duration of preferably less than about 12 hours to be administered from about CT 6 to about CT 18 to achieve a phase advance, or from about CT 18 to about CT 6 to achieve a phase delay. Administration using this protocol has as one basis the stimulation of the greatest extent of the "area under the curve" (AUC) of the phase advance or phase delay zone of the melatonin PRC, while avoiding stimulation of the other zone of the PRC to achieve a circadian rhythm phase-shifting effect in one direction (phase advance) or the other (phase delay). In these embodiments of the methods of the invention, for phase advances, exogenous melatonin administration produces in the human a plasma melatonin concentration of greater than quiescent melatonin levels for a time or in a concentration during a time interval from about CT 6 to about CT 18 that is greater than that produced during the time interval from about CT 18 to about CT 6. For phase delays, exogenous melatonin administration produces in the human a plasma melatonin concentration of greater than quiescent melatonin levels for a time or in a concentration during a time interval from about CT 18 to about CT 6 that is greater than that produced during the time interval from about CT 6 to about CT 18.

The invention also provides methods for achieving a circadian rhythm phase-shifting effect comprising the step of elevating plasma melatonin concentration above quiescent melatonin levels at a time and for a duration that overlaps with the individual human's onset or offset of endogenous melatonin production. For a phase-advance, exogenous melatonin is administered at a time and in a formulation having a duration sufficient to provide for overlap of the elevated plasma melatonin concentration caused by administration of exogenous melatonin with the onset of increased plasma melatonin concentration caused by endogenous melatonin production. For most individuals, the time of onset of endogenous melatonin onset occurs at about CT 14 or typically at about 9 p.m., 14 hours after the first sufficiently-bright light exposure received by the human upon awakening. For different melatonin formulations, administration of melatonin before about CT 14 is advantageous for producing a phase advance. For example, immediate-release formulations are preferably administered from about CT 6 to the onset of endogenous melatonin production, whereas sustained-release formulations and delayed release formulations are administered to raise plasma melatonin concentration levels above quiescent melatonin levels preferably from about CT 6 to about CT 18. It will be recognized by those with skill in the art that alternative times of administration are also encompassed by the methods of the present invention, provided such alternative administration schedules produce elevated plasma melatonin concentration levels that overlap with the onset of endogenous melatonin production, to produce a phase advance.

For a phase delay, exogenous melatonin is administered at a time and in a formulation, having a duration sufficient to provide for overlap of the elevated plasma melatonin concentration caused by administration of exogenous melatonin with the offset of increased plasma melatonin concentration caused by endogenous melatonin production. Endogenous melatonin offset occurs at about CT 1, which is about one hour after an individual's first morning sufficiently-bright light exposure (which occurs at awakening for individuals who awaken after daybreak), and typically corresponds to clock time of about 8 a.m. For different melatonin formulations, administration of melatonin before about CT1 is advantageous for producing a phase delay. For example, immediate-release formulations are preferably administered from about CT 18 to the offset of endogenous melatonin production, whereas sustained-release formulations and delayed-release formulations are preferably administered to raise plasma melatonin concentration levels above quiescent melatonin levels from about CT 18 to about CT 6. It will be recognized by those with skill in the art that alternative times of administration are also encompassed by the methods of the present invention, provided such alternative administration schedules produce elevated plasma melatonin concentration levels that overlap with the offset of endogenous melatonin production to produce a phase delay.

Since the beginning of increased plasma melatonin concentrations defines the rise of the exogenous melatonin pulse, while the end of in creased plasma melatonin concentrations defines the fall of the exogenous melatonin pulse, the time between the rise and fall defines the duration of the pulse of increased plasma melatonin concentration due to exogenous melatonin administration. The duration of the pulse is expected to vary depending on the formulation of melatonin administered to the individual. Administration of immediate-release melatonin formulations (as disclosed in U.S. Pat. No. 5,242,941, incorporated by reference) is characterized by a rapid increase in plasma melatonin concentration, of up to several thousand-fold higher than typical endogenous melatonin plasma concentrations depending on the size of the total dose administered, followed by a gradual (compared with the rate of increase) clearance of elevated plasma melatonin levels to quiescent levels (i.e., defined herein as being less than about 1 to about 10 pg/mL). Sustained-release melatonin formulations (as disclosed in co-owned and co-pending U.S. Ser. No. 08/480,558, incorporated by reference) produce an elevated plasma melatonin concentration (i.e., defined herein as being greater than about 1 to about 10 pg/mL) over a longer time course, ranging from about 3 to about 19 hours in duration. Delayed-release formulations display the kinetics and profile of immediate-release formulations, but include a time lag or delay between administration time and the time of the exogenous melatonin rise. Formulations comprising mixtures and combinations of formulations having these plasma melatonin profiles are understood in the art and provide for flexibility and variety in melatonin administration regimes. Of particular importance in this regard is the use of sustained- or delayed-release formulations that provide for the rise of exogenous melatonin plasma concentrations at times later than administration times which would be inconvenient or counter-productive to address directly (such as causing a melatonin pulse during an individual's sleep phase to maximally stimulate one zone of the melatonin PRC while minimally stimulating the other; see below).

The magnitude of the phase-shifting effect caused by exogenous melatonin administration, according to the methods of the invention, depends on the difference between the time of the exogenous rise and the time of the endogenous onset (for a phase advance) or the difference between the time of the endogenous offset and the time of the exogenous fall (for a phase delay). Also, preferably the exogenous fall overlaps the endogenous onset for a phase advance, and the exogenous rise overlaps the endogenous offset for a phase delay. However, melatonin pulses wherein both the rise and the fall precede the endogenous melatonin onset, or wherein both the rise and the fall occur within the endogenous melatonin profile, also produce circadian rhythm phase-shifting effects (phase advances or phase delays, respectively), albeit less efficiently than administered pulses that overlap the endogenous onset or endogenous offset. In these embodiments of the invention, the magnitude, extent and direction (phase advance or phase delay) of the achieved phase-shifting effect is dependent on the difference between the midpoint of the plasma melatonin concentration duration of the exogenous pulse of melatonin administration and the midpoint of the plasma melatonin concentration duration of the endogenous profile of melatonin production.

The magnitude of the melatonin phase shift also depends on the extent of exogenous melatonin stimulation of each zone of the melatonin phase response curve (PRC). Phase advances of the greatest magnitude are produced by stimulation of the maximum portion of the phase-advance zone of the melatonin PRC, which extends from about CT 6 to about CT 18. Phase delays of the greatest magnitude are produced by stimulation of the maximum portion of the phase-delay zone of the melatonin PRC, which extends from about CT 18 to about CT 6. In addition, the magnitude of the achieved phase-shifting effect is diminished to the extent that the opposite zone of the melatonin PRC is stimulated (i.e., exogenous melatonin stimulation between about CT 18 and about CT 6 can diminish a phase advance and exogenous melatonin stimulation between about CT 6 and about CT 18 can diminish a phase delay). Thus, circadian rhythm phase-shifting is optimally achieved by stimulation of the appropriate zone of the melatonin PRC wherein stimulation of the other zone of the melatonin PRC is avoided. This appears to be important for achieving phase advances, so that administration of exogenous melatonin in a formulation having a maximum duration of greater than 12 hours is less advantageous that administration of formulations having a duration of 12 hours or less, that are administered to coincide with only the phase-advance zone of the melatonin PRC. However, at least in the case of phase delays in at least some individuals, stimulation of the greatest extent of the phase delay portion of the melatonin PRC can be accompanied by further stimulation of the phase advance portion of the PRC between about CT 6 and about CT 13, because such an exogenous melatonin pulse will provide both the greatest stimulation of the area under the curve of the delay portion of the melatonin PRC and the greatest difference between the endogenous offset and the exogenous fall, without overlap of endogenous melatonin onset. Thus, the negative effects on circadian rhythm phase-shifting produced by stimulation of the opposite (i.e., phase-advance portion of the melatonin PRC) is offset by the positive effects on circadian rhythm phase-shifting produced by increasing the magnitude of the greatest difference between the endogenous offset and the exogenous fall. However, even in this situation, for optimal production of phase delays there should be greater stimulation of the delay zone than the advance zone of the melatonin PRC.

The invention also provides methods for administering melatonin without producing a circadian rhythm phase-shifting effect. It will be understood by those with skill in the art that, as a consequence of the existence of the melatonin PRC (first disclosed in U.S. Pat. No. 5,242,941, issued Sep. 7, 1993 and incorporated herein by reference), almost any administration of exogenous melatonin will potentially cause a phase shift. Melatonin administration performed in ignorance of such effects on an individual's PRC runs the risk of causing inappropriate phase shifts, which may act contra to the other physiological effects intended to be produced by said melatonin administration. Thus, it is evident from the present disclosure and the teachings of U.S. Pat. No. 5,242,941 that an individual's melatonin PRC must be understood and taken into account whenever exogenous melatonin is administered to a human, even if a phase shift is to be minimized or avoided.

These considerations become especially important in the treatment of certain circadian rhythm-related pathological disorders. For example, because of the simultaneous existence (co-morbidity) of insomnia not related to phase disturbances and phase-related sleep problems, melatonin pulses may have to be carefully crafted to stimulate one zone of the melatonin PRC and to avoid stimulation of the other zone, as well as to take advantage of any soporific side effects associated with administration of melatonin.

In embodiments of the invention providing methods of administering melatonin without producing phase-shifting effects, exogenous melatonin is administered to provide an interval between the exogenous rise and the endogenous onset that is equal to the interval between the endogenous offset and the exogenous fall. (This is equivalent to providing the midpoint of the exogenous pulse to be about 12 hours out of phase with the midpoint of the endogenous profile.) Alternatively, the invention provides melatonin administration methods that avoid phase-shifting effects by stimulating the phase-advance and phase-delay zones of the melatonin PRC equally, with administration of exogenous melatonin having a duration that overlaps equal portions of the two zones of the melatonin PRC.

In alternative embodiments the invention also provides methods for administering melatonin antagonists, inverse agonists or compounds that reduce endogenous melatonin production without producing phase-shifting effects. In these embodiments of the invention, melatonin antagonists or inverse agonists are administered to provide an interval between the exogenous rise and the endogenous onset that is equal to the interval between the endogenous offset and the exogenous fall. Alternatively, the invention provides methods for administering melatonin antagonists or inverse agonists that avoid phase-shifting effects by stimulating the phase-advance and phase-delay zones of the melatonin PRC equally, with administration of melatonin antagonists or inverse agonists having a duration that overlaps equal portions of these two zones of the melatonin PRC.

The invention also provides methods for achieving a circadian rhythm phase shift wherein exposure (or lack of exposure) to sufficiently-bright light is used to affect the duration of a human's endogenous melatonin production profile. In these embodiments of the methods of the invention, exposure to light is provided to suppress endogenous melatonin production, so that exposure to light during the time when endogenous melatonin production would otherwise occur during the phase-advance zone of the melatonin PRC (about CT 14 to about CT 18) will produce a phase delay, and exposure to light during the time when endogenous melatonin production would otherwise occur during the phase-delay zone of the melatonin PRC (about CT 18 to about CT 1) will produce a phase advance. Comparison with the melatonin PRC reveals that light produces a phase response curve similar in shape but 12 hours out of phase with the melatonin PRC. Exposure to light coincident with the phase-advance zone of the melatonin PRC, particularly from about CT 14 to about CT 18 where endogenous melatonin production would otherwise occur, will delay, an individual's endogenous melatonin onset time by reducing endogenous melatonin production during the advance zone of the melatonin PRC, thus causing a phase delay. Similarly, exposure to light coincident with the phase-delay zone of the PRC, particularly from about CT 18 to about CT 1 where endogenous melatonin production would otherwise occur, will advance an individual's endogenous melatonin offset time and result in a phase advance. The use of compounds that reduce endogenous production of melatonin (e.g., beta-blockers, as described below) between part or all of the interval from about CT 14 to about CT 1 can be substituted for light suppression of endogenous melatonin production.

Conversely, lack of exposure to light (equivalent to exposure to dim light or darkness) will reduce suppression of endogenous melatonin production by ambient light and have some of the same effects and be subject to the same provisions for effecting circadian rhythm phase shifting as disclosed above for exogenous melatonin administration. For example, exposure to darkness during the phase-advance zone of the melatonin PRC, particularly between about CT 14 and about CT 18 will reduce suppression by light of endogenous melatonin production during the advance zone of the melatonin PRC and will shift an individual's melatonin onset time earlier, thereby resulting in a phase advance. Similarly, exposure to darkness during the phase-delay zone of the melatonin PRC, particularly from about CT 18 to about CT 1, will reduce suppression by light of endogenous melatonin production during the delay zone of the melatonin PRC and will shift an individual's endogenous melatonin offset to a later time, thereby resulting in a phase delay. Alternatively, other means of reducing bright light exposure, such as wearing dark or red-tinted goggles or other eye accouterment, are used to produce a circadian rhythm phase-shifting effect (as disclosed in U.S. Pat. No. 5,591,768, incorporated by reference). Exposure to darkness is also provided by the expedient of the individual taking a nap during the appropriate zone of the melatonin PRC to achieve the desired circadian rhythm phase-shifting effect.

Melatonin agonists or melatonin antagonists (and inverse agonists) are also provided wherein administration mimics, or opposes, respectively, the action of melatonin on the melatonin PRC to achieve the desired circadian rhythm phase-shifting effect. Melatonin blockers or stimulants also mimic the effects of bright light or darkness (or dim light), respectively, in their effects on endogenous melatonin production. The phase-shifting effects of melatonin inverse agonists, melatonin agonists and melatonin blockers can be predicted according to the melatonin PRC, and in the case of melatonin blockers, also according to how the post-treatment onset and offset of endogenous melatonin production relate to the pre-treatment onset and offset.

In a preferred embodiment, beta-blockers are administered to an individual to inhibit endogenous melatonin production and thereby mimic the effects of light on endogenous melatonin production. Preferably, beta-blockers are administered having a duration that overlaps either the onset or offset of endogenous melatonin production, wherein the change in endogenous melatonin onset or offset determines the extent of the phase shift produced: a later onset will cause a phase delay, and an earlier offset will cause a phase advance. Additionally, beta-blockers are preferably administered to coincide with a portion of the appropriate zone of the melatonin PRC to achieve a circadian rhythm phase-shifting effect. For a phase advance, administration of beta-blockers from about CT 18 to about CT 1 reduces endogenous melatonin production in the delay zone of the melatonin PRC as well as shifts the offset of endogenous melatonin production to an earlier time, thereby resulting in a phase advance. For a phase delay, administration of beta-blockers from about CT 14 to about CT 18 reduces endogenous melatonin production in the advance zone of the melatonin PRC as well as shifts the individual's endogenous melatonin onset to a later time, resulting in a phase delay. Thus, beta-blockers are administered according to the methods of the invention having a duration appropriate for overlap of endogenous melatonin onset or offset and to suppress endogenous melatonin production during the appropriate zone of the melatonin PRC.

Thus, to obtain a circadian rhythm phase-shifting effect according to the methods of this invention, melatonin administration is accomplished so that there is an overlap either between the rise in post-treatment melatonin plasma concentration levels and the offset of pre-treatment endogenous melatonin production, or between the fall in post-treatment levels and the onset of pre-treatment levels. In either event (and also when overlap occurs in both cases or occurs in neither case), the change in the onset/rise compared to the change in the offset/fall predicts the magnitude and direction of the resulting phase shift. An equal change in the onset/rise compared with the offset/fall is useful for avoiding a circadian rhythm phase shift, for example, when melatonin is administered for a reason other than phase shifting). These teachings apply to the administration of exogenous melatonin, melatonin agonists and light exposure, and to compounds that affect (enhance of diminish) endogenous melatonin production in a human, as well as melatonin antagonists and inverse agonists, which effectively "reduce" plasma melatonin levels by blocking the action of melatonin on melatonin receptors or by inducing the "inverse" response at such receptors. The invention also encompasses methods that stimulate one zone (i.e., phase advance or phase delay) of the melatonin PRC more than the other, and preferably stimulate one zone rather than the other, to produce a phase shift, while stimulating both zones equally when administering melatonin, melatonin agonists, melatonin antagonists, melatonin inverse agonists, compounds that endogenous melatonin production in a human, or light, to avoid a phase-shifting effect.

The present invention may be used in, but is not limited to, the following situations to achieve chronobiologic effects and/or to alleviate circadian rhythm phase disorders: jet lag; shift work; people who have a maladaptation to work and off-work schedules; submariners, or persons confined for research, exploration or industrial purposes below the seas; miners, explorers, spelunkers, researchers or those confined beneath the Earth; psychiatric patients; insomniacs; the comatose, or those who need to be maintained in a state of unconsciousness for medical, psychiatric or other reasons; medical residents, nurses, firemen, policemen or those whose duties require alertness and wakefulness at evening or nighttime hours, or those deprived of sleep for various periods because of their duties or responsibilities; the infantry, or other members of the armed forces whose duties require extreme levels of alertness and wakefulness, and who may be sleep deprived in the performance of these duties; astronauts in orbit around the Earth, on missions in space to the Earth's moon or to the planets or out of the known solar system, or in training for such missions; the blind or sight-impaired or all those whose ability to distinguish differences in light and dark may be permanently or temporarily impaired; residents of the far North or Antarctica, or all those who live in a climate or climates that possess abnormal amounts of light or darkness; those suffering from seasonal affective disorder, winter depression, or other forms of depression; infants, particularly newborns; the aged; Alzheimer's disease patients, or those suffering from other forms of dementia; the sick, or those who require dosages of medication at appropriate times in the circadian cycle; animal breeders, for use in controlling circadian time; and for ameliorating the phase-disrupting effects of changing from Standard to Daylight Savings Time or vice versa.

Five types of insomnia can also be helped by melatonin administration. One, termed pure insomnia, is not particularly related to a circadian phase disturbance, and melatonin is useful for its soporific qualities. Two insomnias are known to be circadian rhythm-related insomnias; advanced sleep phase syndrome (ASPS) and delayed sleep phase syndrome (DSPS). There are also two types of mixed insomnias, termed pure insomnia plus ASPS and pure insomnia plus DSPS. Since most people have intrinsic circadian periods greater than 24 hours (which explains why so many people have at least some difficulty falling asleep quickly initially and waking up easily and alert), an agent that causes a phase advance acts to re-entrain circadian rhythms to the 24 hour light/dark cycle.

Melatonin Administration Under Medical Supervision

The present invention provides methods useful in the treatment any of the above-listed conditions, under direct medical supervision, wherein melatonin administration times are chosen after determination of an individuals actual DLMO time. In certain instances, an individual's PRC must also be specifically determined, for example, in those patients where use of melatonin precursors, stimulants, analogs, agonists, inverse agonists, antagonists, or melatonin blockers require a more precise determination of dose and time of exogenous administration. Examples of such instances include individuals whose response to melatonin treatment, or absorption or metabolism of melatonin or melatonin agonists, antagonists or precursors may vary from the normal response, thereby necessitating medical supervision.

A certain portion of the human population falls outside of what is considered the "normal" human characteristics of drug absorption, or have circadian rhythms with unusual characteristics. These individuals may require a more accurate determination of the individual melatonin PRC before attempting intervention. Other individuals who may be suffering from pathological or clinical circadian rhythm phase disorders may also benefit from a more accurate determination of the melatonin PRC or at least the DLMO before intervention. In a controlled setting, under medical supervision, a more precise and specific intervention of the melatonin PRC or of just the baseline DLMO can be accomplished using the methods of the present invention to effect predictable phase advances or delays. In certain individuals, the endogenous circadian pacemaker (or "body clock") may in some circumstances (such as the result of melatonin or light/dark cycle induced phase shifts) shift faster than the DLMO. In such cases, the rate of change in the melatonin PRC may need to be determined directly for optimal scheduling of melatonin administration or light exposure, although estimations are possible here as well.

Under medical supervision, a subject can have the DLMO time determined carefully by sampling physiological levels of melatonin in blood, saliva or other biological fluids. The concentration of melatonin can be determined analytically using methods including but not limited to gas chromatography-mass spectrometry (GC-MS), radioimmunoassay (RIA) or enzyme-linked immunosorbent assay (ELISA) methods. The advantage of medical supervision is to more accurately and exactly determine an individual's DLMO time and establish their melatonin PRC. This information then enables specific and precise intervention by exogenous melatonin administration for adjusting s human's circadian rhythms in a predictable manner.

Melatonin Administration by the Individual

In another embodiment of the invention, melatonin administration can be performed directly by an individual without medical supervision. For such uses, times of exogenous melatonin administration can be described, for example in a table, instructing the individual to take melatonin at specific times based upon normal bedtime and waking time and the magnitude and direction of the desired phase shift. For example, the use of the methods herein described to alleviate the effects of jet lag can advantageously be enabled by an article of manufacture comprising melatonin in a consumer-accessible formulation, accompanied by charts or tables setting out proper clock times of exogenous melatonin administration based on the number of time zones crossed in travel and the direction of travel, and also based either on characteristically "normal" human DLMO times or with reference to any other indicia of an individual's actual DLMO time (such as the individual's actual wake-up time). In other specific examples of embodiments of the invention for treating jet lag, melatonin may be administered in timed-release formulations that are geared to release melatonin in conjunction with the number and direction of time zones crossed, releasing the melatonin at the proper times. Such articles of manufacture and melatonin formulations are expressly within the scope of the instant invention. Analogous articles of manufacture, formulations and methods of administration for treating other circadian rhythm phase disorders are also provided by and within the scope of the invention.

A. Kit for Determining DLMO

For many individuals a less precise determination of their DLMO time will enable them to use the methods provided by this invention to effect a desired circadian rhythm phase shift based on an estimate of their DLMO time. A convenient means for allowing an individual to adjust the DLMO in a predictable manner and without medical supervision would involve the use of a simple home assay kit. This assay kit would allow the individual to determine his own melatonin onset or DLMO time by sampling biological fluids at short intervals during the course of part of a normal day.

1. Dip Stick for Saliva

In one embodiment, the amount of melatonin or melatonin metabolite in the individual's saliva could be assayed simply by applying a saliva sample to an applicator stick designed to react with melatonin or melatonin metabolite in a concentration-dependent fashion. The individual could compare the assay sticks contacted with saliva over a period of time and use an interpreting means (such as a color comparison strip) to determine the approximate DLMO time. Once an individual had determined the DLMO time, tables or other instruction means based on the DLMO time and providing a schedule of exogenous melatonin administration times for achieving a desired phase shift could be used to inform the individual when and how much melatonin to take to achieve the desired phase shift.

2. Blood drop test

In another embodiment, an individual could use a drop of blood to assay for the physiological concentration of melatonin or melatonin metabolite, similar to methods currently in use for determining blood levels of sugar or cholesterol. This assay would result in a quantitatively more accurate determination of the individual's DLMO time compared with the previously-described dip stick method and would be useful for applications of the methods of the invention wherein more accurate estimates of the DLMO time are required.

Alternatively, in certain instances it may be advantageous to apply these approaches seriatim, i.e., wherein DLMO times are estimated using awakening as a circadian marker, and in cases where this estimate proves unsatisfactory or sub-optimal, DLMO times determined more precisely. The nighttime melatonin profile (including DLMO time) can be obtained by testing blood, urine, saliva or other body fluid for the presence of melatonin or physiological or metabolized products thereof.

The methods of this invention encompass melatonin administration times based upon an individual's PRC and DLMO time, whether actually determined or estimated. Administration times are prescribed relative to the DLMO time; however, the DLMO time will, by definition, change as a circadian rhythm phase shift is accomplished by exogenous melatonin administration and an individual's melatonin PRC is readjusted (accompanied by resynchronization of the individual's circadian rhythms with the external environment). Thus, exogenous melatonin administration times are, in preferred embodiments, also adjusted to provide a constant relationship between administration time and DLMO.

Melatonin can also be administered in combination with scheduling bright light administration, ordinary-intensity light exposure, or exposure to dim-light or darkness (or even sleep). In one embodiment of this aspect of the invention, melatonin administration using the methods disclosed herein is accompanied by having an individual wear dark or red goggles at the, time of melatonin administration, to provide for the additive effects of the combination of melatonin treatment plus darkness. In another embodiment of this aspect, the individual wears dark goggles at times including times other than the time of melatonin administration to avoid the occurrence of a conflicting external zeitgeber in opposition to the phase shift promoted by the exogenous melatonin administration protocol. In another embodiment, light can be used to suppress endogenous melatonin production when this would occur at the "wrong" time, i.e., at a time according to the melatonin PRC which would be antagonistic to the desired phase shift.

Undesirable endogenous melatonin production can also be suppressed pharmacologically by melatonin blockers using a number of pharmaceutical agents, including but not limited to alpha-2-noradrenergic agonists, beta-adrenergic receptor blockers and benzodiazepines. It may also be desirable to suppress all or a part of the endogenous melatonin profile, for example, to cause receptor supersensitivity; partial suppression creates a new onset or offset and reduces endogenous melatonin from stimulating the undesirable part of the melatonin PRC or eliminates potentiating effects of a competing melatonin, melatonin-like or darkness (sleep) signal. One example of this embodiment is the use of atenolol plus a very low dose of melatonin (0.125 mg) in the treatment of winter depression (as described in U.S. Pat. No. 5,591,768, incorporated by reference). Atenolol is given at about CT 14 and low-dose melatonin at about CT 8. Atenolol blocks endogenous melatonin production that would otherwise primarily occur during the delay zone (which promotes a phase advance), and it also induces supersensitivity to the melatonin administered at about CT 8. It is also noted that patients taking such drugs for other clinical reasons can be expected to have circadian rhythm side effects, so that it is advantageous to work a compensatory adjustment in their melatonin levels to avoid unwanted phase shifts.

Certain other drugs, such as melatonin stimulants (for example, tricyclic antidepressants, noradrenergic and serotoninergic re-uptake blockers, MAO inhibitors and alpha-2-adrenergic antagonists) can raise endogenous melatonin levels, particularly between about CT 14 and about CT 1. This side effect will also affect an individual patient's "biological clock" in ways predicted by the melatonin PRC.

Melatonin precursors such as, tryptophan, 5-hydroxytryptophan, serotonin and N-acetylserotonin may also raise endogenous melatonin levels and affect circadian rhythms, either via their conversion to melatonin, or by the direct action of these compounds on melatonin receptors. Such influences are predictable using the melatonin PRC, adjusted to account for absorption time, metabolic conversion rates, etc.

The invention also contemplates the co-administration of sedative-hypnotics, or soporific doses of melatonin (>1 mg) for use in circumstances in which the soporific compounds are administered along with lower doses of melatonin given primarily during wake times.

As mentioned above, the phase-shifting effects of compounds that act opposite to melatonin (antagonists, inverse agonists, blockers) can be analyzed and predicted by the melatonin PRC. In general, however, the phase-shifting effects of these compounds are more complex than those of melatonin because these effects depend on whether a particular compound acts directly on melatonin receptors to compete with melatonin binding (defined as an antagonist), or acts to reduce endogenous melatonin production (defined as a melatonin blocker) or acts to cause an effect opposite to melatonin (defined as an inverse agonist).

Melatonin Administration: Formulations

A. Fixed-dose Melatonin Formulations

In the simplest formulations, melatonin is provided as fixed-dose pharmaceutical compositions. Such compositions and means for making such compositions are well known in the art. Fixed-dose formulations provide a predictable phase shift in a "normal" individual when administered using the methods of the invention herein disclosed. Clock time for melatonin administration depends on the magnitude and direction of the desired shift, and the DLMO time of the individual.

1. Based on an individual's actual DLMO time

An accurately-determined DLMO time for an individual can be determined by medical assay or by the home assay methods disclosed above. The administration times appropriate for obtaining the desired phase shift are then predicted by the melatonin PRC. The times and dosages of exogenous melatonin administration provided by the present invention may be used to achieve the desired phase shift.

2. Based on an individual's estimated DLMO time

In many instances, the magnitude of the preferred phase shift, or the amount of an individual's desire for the phase shift {i.e., whether phase shifting is medically necessary (e.g., in winter depression patients) or less seriously (e.g., for jet lag)}, may permit the administration of melatonin based upon an estimated DLMO time. This can be done by using the phase position of an individual's typical wake-up and sleep-onset times as being about CT 0 and about CT 16, respectively. Using exogenous melatonin administration schedules based on such rough estimates of the DLMO time allow reasonably good intervention for most people. Such interventions can still encompass most of either the estimated advance or delay zone of the melatonin PRC without overlapping with the other zone of the PRC that predicts a phase-shifting effect opposite to the desired effect. Methods using estimated DLMO times are particularly applicable for alleviating circadian rhythm phase disturbances caused by transmeridional travel, shift work and other man-made circadian rhythm desynchronizations of human circadian rhythms. Immediately after a change in sleep/wake time, the DLMO is at about the same clock time as before the change. It then often shifts by about 1–3 hours per day, and after several days is again at about 14 hours after an individual's typical wake-up time of the new schedule.

B. Timed-Release Melatonin Formulations

Melatonin formulations can be designed to administer the dose of melatonin slowly over a period of time at a fixed rate, quickly at a specific time after the taking of the formulation, or at any other combination of release times and rates. Such formulations can be made by those with skill in the pharmaceutical arts.

1. That shift release time over the period of administration.

Formulations of melatonin can be designed which can be taken at the same time each day, but which will release melatonin at different times and rates. These formulations can be selected so that the timing of physiological activity of administered melatonin coincides with the times predicted by the melatonin PRC for achieving a desired phase-shifting effect, even though the clock time at which the individual takes melatonin does not change during the course of treatment. In one embodiment, such melatonin formulations could be dispensed in a kit much like birth control pills are currently dispensed, with specific formulations being administered in sequence to achieve the daily shift of exogenous melatotin administration times without requiring the individual to vary daily administration times.

2. That are of fixed time of release but can vary in dosage

The linear relationship between phase shift and melatonin dose has been demonstrated (see Example 6 U.S. Pat. No. 5,591,768). This suggests that formulations of melatonin that release varying doses of melatonin may be useful; methods for making such formulations are known in the art. The use of different dose formulations can also be used in combination over the period of administration. Such an administration format would allow phase shifting of circadian rhythms, including the melatonin PRC, in individuals having unique requirements, for example due to work schedule, disease, personal reaction to melatonin, life style, or other factors. Use of such a formulation would enable the individual to have gradually increasing or decreasing melatonin levels over time.

3. That shift release time and released dosage

Melatonin formulations that release different doses at different release times may also be useful. Such formulations would permit the melatonin dose and time of physiological action to be varied, while still being convenient to use. Use of such formulations would enable administration of sustained low levels of melatonin to achieve the desired phase shift, while avoiding the soporific side effects of large does of melatonin during desired hours of alertness. Similarly, sustained low-level release of melatonin during desired hours of alertness can be followed, or preceded by release of higher levels of melatonin during desired sleep times to enhance both soporific and indirect (sleep and darkness-mediated) phase-shifting effects.

The following Examples describe certain specific embodiments of the invention. However, many additional embodiments not described herein nevertheless fall within the spirit and scope of the present invention and claims.

EXAMPLE 1
Detection of Melatonin Levels in Human Plasma Using Gas Chromatography-Mass Spectrometry Prior to collection of human blood, subjects were kept in dim light for about 5 hours (usually between 6 p.m. and 11 p.m.). An intravenous line or heparin lock was inserted in a forearm vein and 5 mL of blood drawn every 30 minutes between 7 p.m. and 11 p.m. The blood samples were centrifuged for 5 minutes at 1000 g and 4° C., and the plasma aspirated into a silanized glass or plastic tube. Samples were assayed immediately or frozen for later analysis. Saliva samples can alternatively be collected and analyzed To a 1 mL aliquot of such plasma was added 50 picograms of N-acetyl-5-methoxy($\alpha,\alpha,\beta,\beta$-D$_4$)tryptamine as a chromatographic control. An equal volume of normal saline was added and the mixture gently shaken with 8 volumes of petroleum ether. The organic phase was removed, and melatonin and the added N-acetyl-5-methoxy($\alpha,\alpha,\beta,\beta$-D$_4$) tryptamine control extracted from the aqueous phase with 8 volumes of chloroform. The aqueous phase was then discarded, and the chloroform evaporated to dryness.

The dried extract containing melatonin and the added N-acetyl-5-methoxy($\alpha,\alpha,\beta,\beta$-D$_4$)tryptamine control was dissolved in 50 µL ethyl acetate. The melatonin contained in the plasma samples and the added N-acetyl-5-methoxy($\alpha,\alpha,\beta,\beta$-D$_4$)tryptamine control were then derivatized by the addition of 50 µL of pentafluoroproprionic acid anhydride and reacted at 70° C. for 10 minutes. These reaction products were then evaporated to dryness under nitrogen. The dried extract was partitioned between 0.5 mL acetonitrile and 1 mL hexane by vigorous mixing followed by centrifugation and removal of the hexane layer. This partitioning step was repeated twice more, except that the hexane was not removed after the final partitioning. The derivatives are stable and can be stored at −20° C. for several weeks.

The amount of melatonin present in each sample was determined by gas chromatographic-mass spectrometric analysis. Before injection onto the GC column, the dried derivatives were dissolved in 10 µL iso-octane. 2 µL of this volume were applied to a 30 m×25 µm fused silica capillary column {0.15 micron film thickness with a 5 m retention gap (Rtx 225, Restek Corp., Bellefonte, Pa.)}. The oven (HP 5890, Series 2) was programmed from 85° C. to 240° C. with helium as carrier gas (constant flow) and methane used as make-up gas (ionizer, 2.0 torr). Derivatized melatonin and the added N-acetyl-5-methoxy($\alpha,\alpha,\beta,\beta$-D$_4$)tryptamine derivatized control were found to elute from the column after 10–14 minutes.

Mass spectrographic analysis of the column eluant was then performed. Mass spectra were recorded using a Hewlett Packard 5989A mass spectrometer with an ETP Scientific electron multiplier using HP Chemstation software. The relative signals of melatonin and the added N-acetyl-5-methoxy($\alpha,\alpha,\beta,\beta$-D$_4$)tryptamine control were detected at m/e (mass/charge) ratios of 320 and 323, respectively. The amount of melatonin present in any unknown sample can be determined by comparison of the ratio of the intensities of these signals to a standard curve, prepared as described using known amounts of melatonin and added N-acetyl-5-methoxy($\alpha,\alpha,\beta,\beta$-D$_4$)tryptamine control.

EXAMPLE 2

Melatonin was administered to nine subjects as two doses of 0.25 mg, two hours apart, thereby simulating a sustained-release (SR) formulation. Subjects were administered melatonin by capsule for four days with the following regimen: placebo capsules were given for the first, two days and melatonin capsules were given during the last four days, followed by a day during which the dim light melatonin onset (DLMO) was determined. The DLMO was used because it is an excellent marker for circadian phase position. The week before this administration regime, each subject's baseline DLMO was assessed after a six-day course of treatment using only placebo capsules. Phase shifts were calculated by subtracting the post-treatment DLMO from the pre-treatment DLMO.

The results of these studies are shown in FIG. 1. FIG. 1 illustrates phase shifts (double-plotted) for nine subjects who participated in a total of 30 trials. The circadian time of administration is referenced to the time of the first capsule. In these studies, maximal phase advances were found to occur around CT 7.5 (see FIG. 1). The data clearly support the conclusion that the earlier melatonin is administered in the afternoon and evening, the greater the degree of the resulting phase advance. However, if melatonin is administered too early (i.e., before about CT 7.5), the extent of induced phase advances diminish in magnitude or, for very early administration times, phase delays occur. The phase-advancing effect of exogenous melatonin administration was found to depend on the initial time of ingesting the capsule. This results in a phase relationship between the exogenous rise and the endogenous onset, characterized in that—within certain limits—the earlier the rise occurs relative to the onset, the greater the phase advance. These results provided the first evidence of a phase response curve for melatonin in humans.

EXAMPLE 3

Melatonin was administered to five subjects as a single 0.5 mg (or immediate-release (IR)) dose. Subjects were administered placebo capsules for the first week of the study. For the second week, subjects were given placebo capsules for two days followed by four days of melatonin administration. Dim light melatonin onset (DLMO) times were determined at the end of each week. Phase shifts were calculated from a comparison of the post-treatment DLMO to the pre-treatment DLMO. Subjects participated in a series of twelve trials in which melatonin was administered at different times of the day and night, resulting in individual phase response curves (PRCs) for exogenous melatonin.

Figure 2:
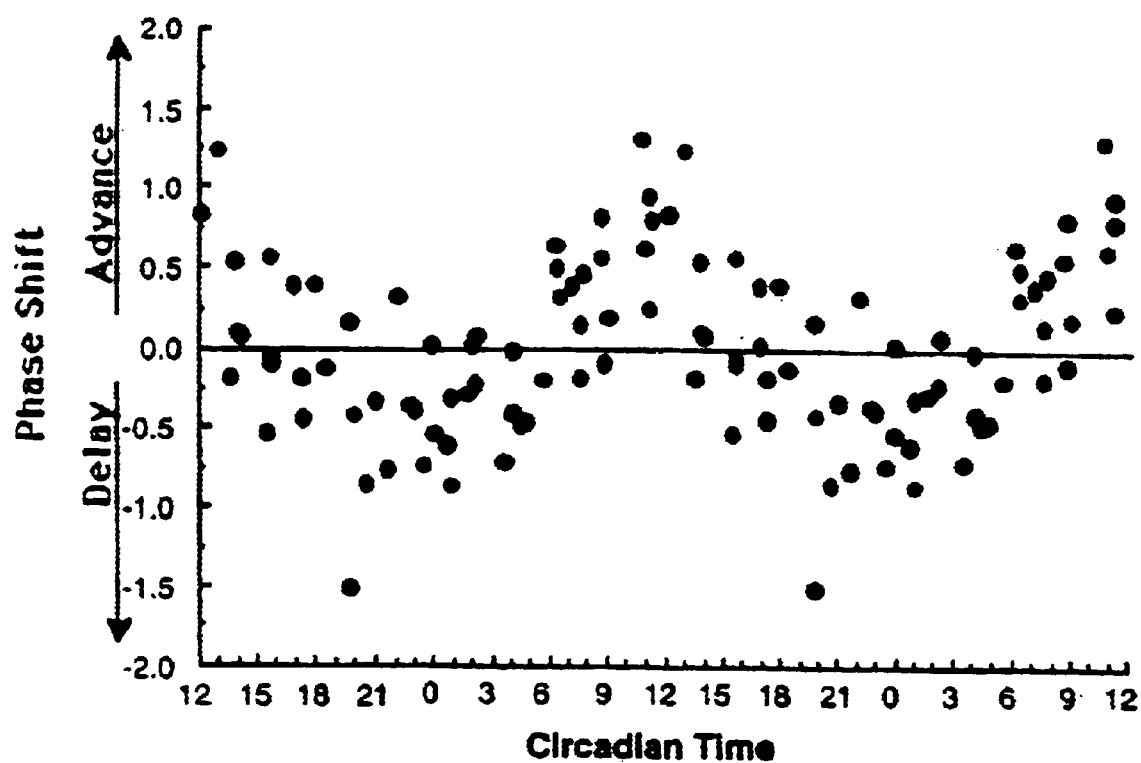
FIG. 2 illustrates circadian rhythm phase shifts in the melatonin PRC for 5 subjects who participated in melatonin phase response curve trials as described in Example 3.

The results of these studies are shown in FIG. 2, illustrating phase shifts (double-plotted) for five subjects (a total of twelve trials each). The results of these studies indicated that the circadian time for maximal phase advances was about CT 11. In this study, the same total dose of melatonin was administered as in the study described in Example 2. In this example, however, the earlier melatonin was administered prior to CT 11, the less the magnitude of the induced phase advance. Phase delays were found to begin at about the same time as found in Example 2 (i.e., at about CT 6).

This result was unexpected, because the IR dose results in a higher maximum physiological concentration of melatonin in the subject's bloodstream ($C_{max}$). This apparent discrepancy in the results of Examples 2 and 3 is explained by recognizing that the single IR dose has a shorter duration than the same total dose administered as a split dose in Example 2. Duration is understood to mean the amount of time exogenous melatonin administration causes or results in plasma melatonin concentration levels to exceed quiescent levels (which, in these individuals, was less than about 10 pg/mL). Because the IR dose is a shorter duration dosage form, these results suggest that the phase relationship between the fall of the exogenous melatonin pulse and the onset of the endogenous melatonin profile is one determinant of the magnitude of the induced phase shift. (Another determinant is the phase relationship between the exogenous rise and the endogenous onset, as described in U.S. Pat. No. 5,242,941, incorporated by reference). These results indicated that the fall of exogenous melatonin should overlap (i.e., occur later than) the onset of endogenous melatonin production. The consistent teachings of both these Examples is that the earlier the afternoon rise of exogenous melatonin relative, to the endogenous onset, the greater the phase advance observed.

Figure 3:
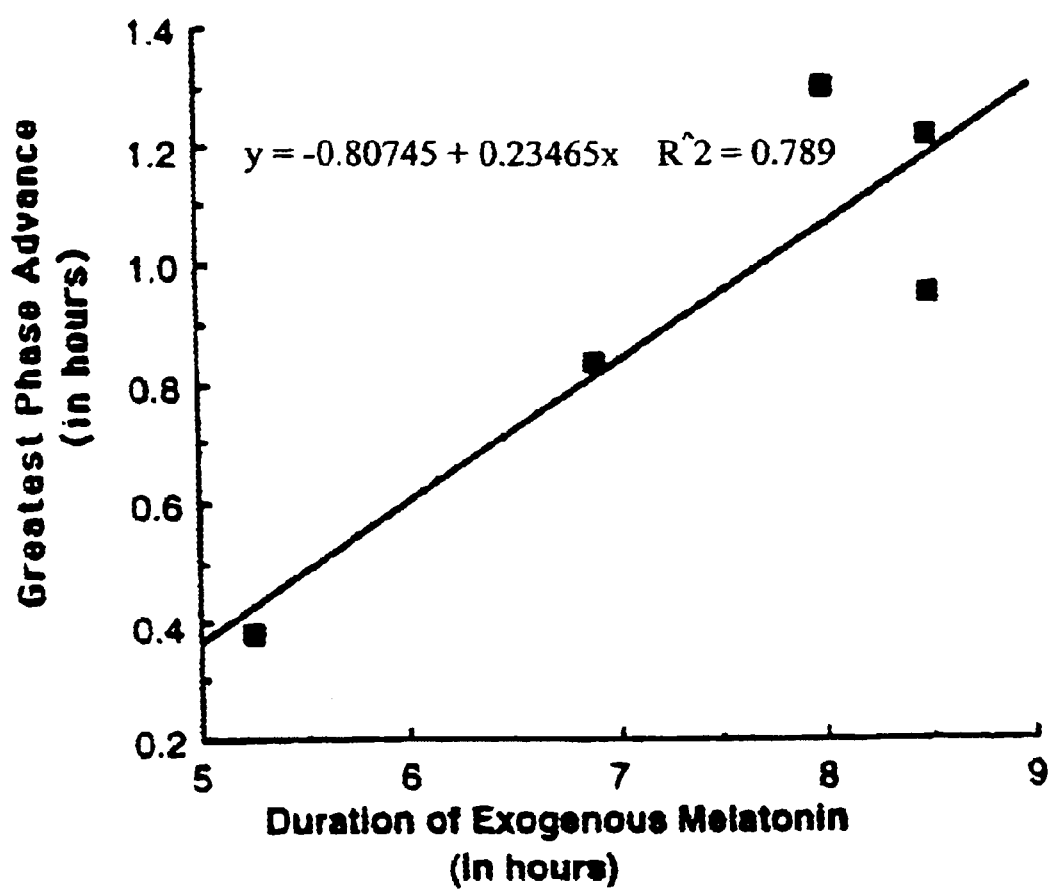
FIGS. 3 and 4 illustrate the relationship between the degree of phase advance and duration (FIG. 3) and half-life (FIG. 4) of exogenous melatonin administered as disclosed in Example 4.

There are a number of similarities between FIGS. 2 and 3. One of the most prominent similarities is that the crossover points between advance and delay responses, and between delay and advance responses, are about CT 18 and about CT 6, respectively. These crossover points divide the melatonin PRC in half. This division makes possible a method of using melatonin pulses for achieving a circadian rhythm phase-shifting effect wherein the duration of the exogenous melatonin pulse is about 12 hours, provided the pulse is localized to one half of the melatonin PRC or the other. Such an exogenous pulse stimulates one zone of the PRC and not the other in order to optimally cause a phase shift. This approach is termed the "area under the curve" (AUC) strategy. For optimizing phase shifting using the AUG strategy, the duration of the melatonin pulse is confined to these 12-hour intervals. For enhancing the magnitude of a phase shift, a dose of 12-hours duration is taken at the beginning of the appropriate interval, to stimulate the maximal portion of the appropriate AUC while avoiding as much as possible stimulating the other, inappropriate AUG of the melatonin PRC. Thus, in order to optimally cause a phase delay, melatonin is administered between about CT 18 and about CT 6. In order to cause a phase advance, melatonin is administered between about CT 6 and about CT 18. Based on the average DLMO time of 2100 (9 o'clock p.m.), these circadian times translate to clock times as follows. In order to cause a phase advance, melatonin is administered between about 1 p.m. and 1 a.m. In order to cause a phase delay, melatonin is administered between about 1 a.m. and about 1 p.m. According to the AUC strategy, the duration of the exogenous melatonin administered within these time periods should not be longer than the portion of the appropriate AUC remaining after melatonin is administered.

EXAMPLE 4

Melatonin was administered to five subjects as a single 0.5 mg IR dose. Subjects were administered placebo capsules for the first week of the study. For the second week, subjects were given placebo capsules for two days followed by four days of melatonin administration. DLMOs were determined at the end of each week. Phase shifts were calculated from the change from the pre-treatment DLMO to the post-treatment DLMO. Subjects participated in a series of twelve trials in which melatonin was administered at different times of the day and night, resulting in individual PRCs for exogenous melatonin. On one occasion, subjects were given 0.5 mg melatonin during the day under normal lighting conditions while plasma samples were drawn to assess pharmacokinetics of melatonin. Results of the pharmacokinetics were analyzed according to duration and half-life, and how they affected the magnitude of phase advances.

Figure 4:
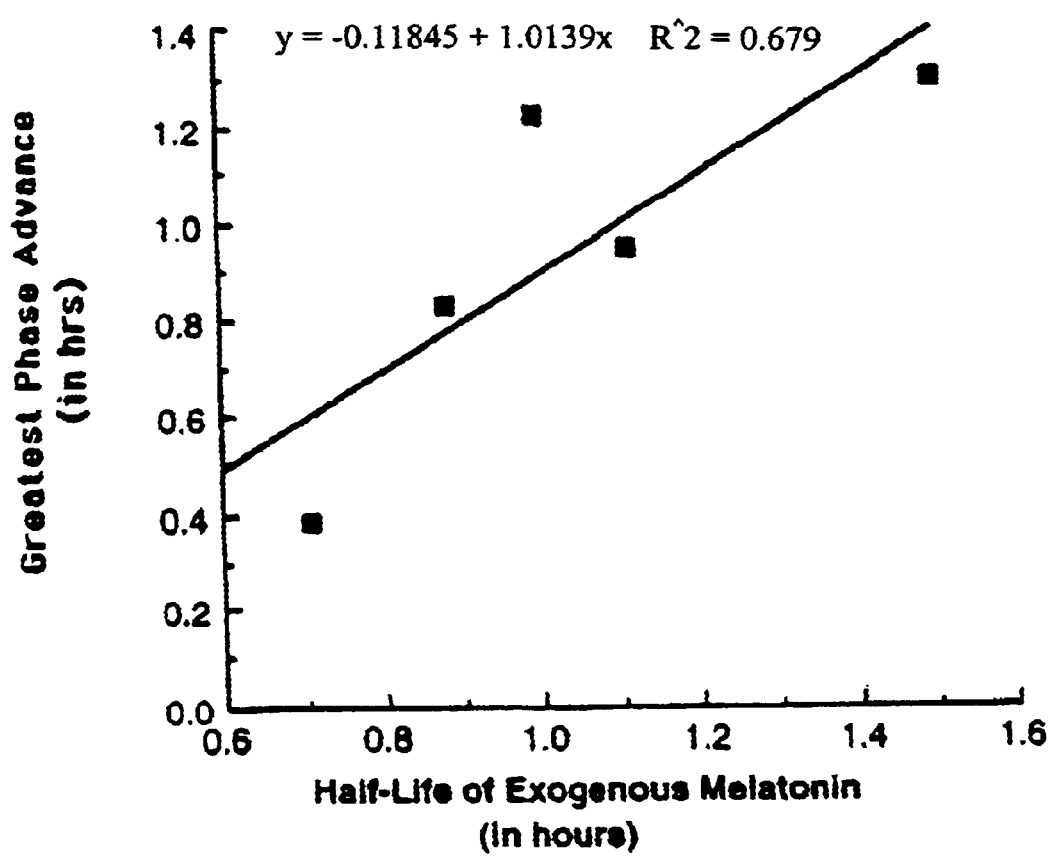

The results of these experiments are shown in FIGS. 3 and 4. FIG. 3 illustrates the relationship between the magnitude of the greatest phase advance observed for each subject versus the duration of the exogenous melatonin pulse. FIG. 4 illustrates the relationship between the magnitude of the greatest phase advance for each subject plotted against the half-life of exogenous melatonin. As is shown in the Figures, it was found that the greater the duration (FIG. 3) and the greater the half-life (FIG. 4) of exogenous melatonin, the greater the phase advance obtained. These results further supported the conclusion that, for achieving a maximal phase advance, exogenous melatonin is administered sufficiently early in the afternoon (as described by the melatonin PRC), and is of sufficient duration or half-life to permit the exogenous melatonin fall to overlap with the endogenous onset. These results also indicated that stimulation by exogenous melatonin of a greater extent of the AUC of the advance zone of the melatonin PRC caused a greater phase advance shift.

EXAMPLE 5

In this study, melatonin was administered to five subjects as a single 0.5 mg IR dose. Subjects were administered placebo capsules for the first week of the study. For the second week, subjects were given placebo capsules for two days followed by four days of melatonin administration. DLMOs were determined at the end of each week. Phase shifts were calculated from the change in the pre-treatment DLMO to the post-treatment DLMO. Subjects participated in a series of twelve trials in which melatonin was administered at different times of the day and night, resulting in individual PRCs to exogenous melatonin. On one occasion, subjects were given 0.5 mg melatonin during the day under normal lighting conditions while plasma samples were drawn to assess pharmacokinetics of melatonin. Results of the pharmacokinetics were analyzed according to duration and half-life, and how they affected the magnitude of phase delays.

Figure 5:
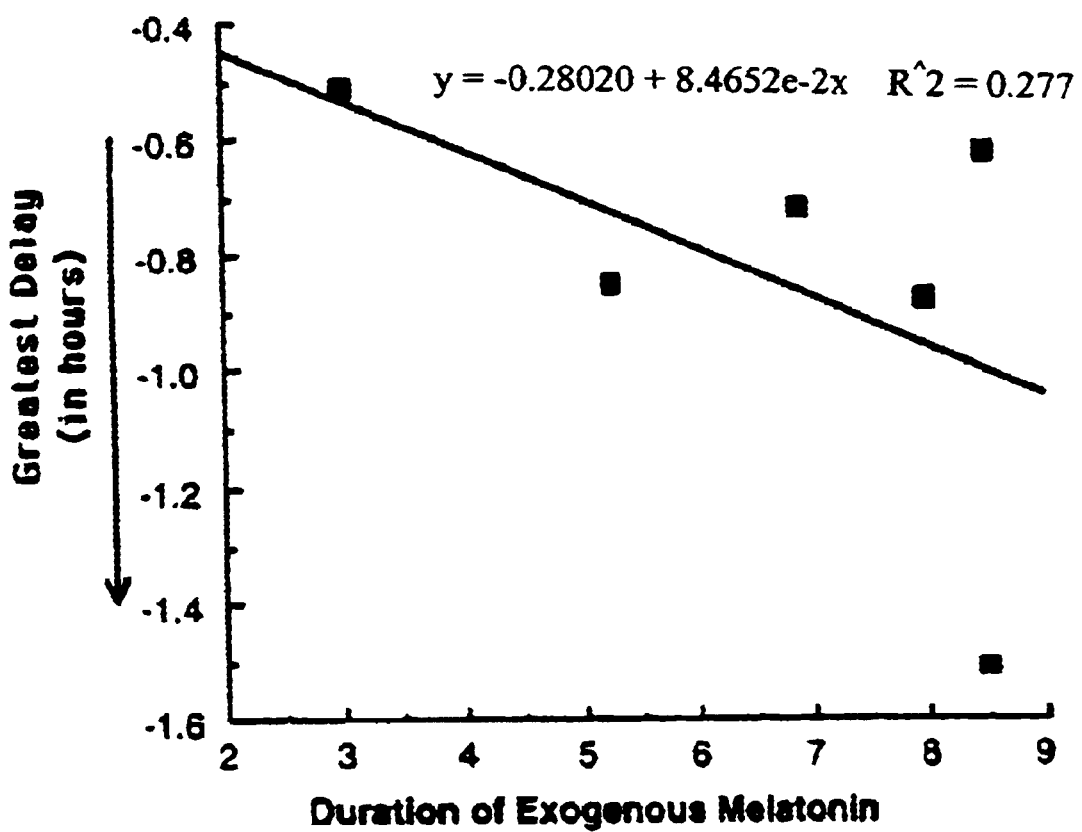
FIGS. 5 and 6 illustrate the relationship between the degree of phase advance and duration (FIG. 5) and half-life (FIG. 6) of exogenous melatonin administered as disclosed in Example 5.
Figure 6:
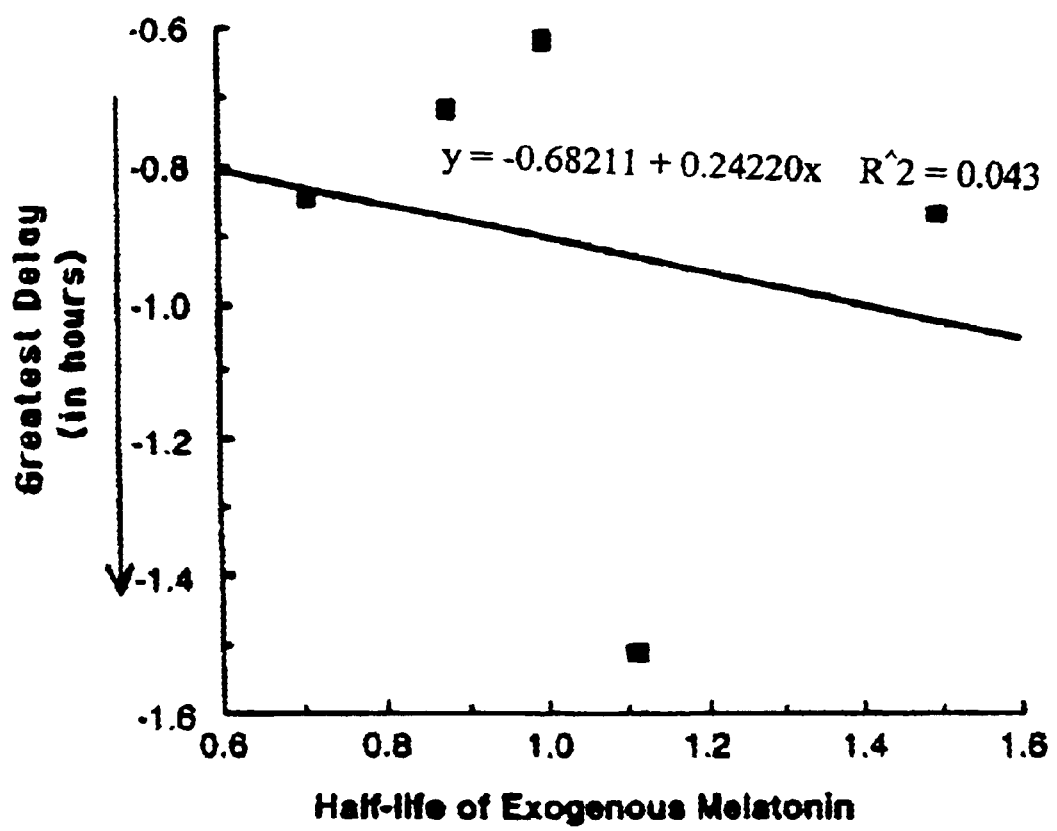

The results of these experiments are shown in FIGS. 5 and 6. FIG. 5 shows the relationship between the magnitude of the phase delay for each subject versus the duration of the exogenous melatonin pulse. FIG. 6 illustrates the relationship between the magnitude of the phase delay for each subject plotted against the half-life of exogenous melatonin. As is shown in these Figures, the greater the duration (FIG. 5) and the greater the half-life (FIG. 6) of exogenous melatonin, the greater the phase delay obtained.

These results extended the experimental results obtained in Example 4 with regard to phase advances to apply to phase delays. These results provided experimental evidence to support the conclusion that, for achieving a maximal phase delay, exogenous melatonin is administered during the delay zone of the PRC, and it has sufficient duration or half-life so that the exogenous melatonin rise overlaps with the endogenous offset. Thus, these results led to the conclusion that—within certain limits—the later the exogenous fall, the greater the phase delay obtained. These results also indicated that stimulation by exogenous melatonin of a greater extent of the AUC of the delay zone of the melatonin PRC caused a greater phase-delay shift.

EXAMPLE 6

The results obtained in Examples 2 through 5 were used to construct empirical tables of preferred melatonin administration times useful for maximizing the magnitude and extent of phase shifts obtained by exogenous melatonin administration (Tables 1 and 2). The right-hand column of Table 1 relates to maximizing a circadian phase-delaying effect by providing that the fall of exogenous plasma melatonin concentration occurs as late as possible, but before the next's night's onset. The middle column of Table 1 relates to achieving a circadian phase-shifting effect by stimulating the maximal extent of the area under the curve (AUC) of the delay zone of the melatonin PRC and avoiding as much as possible stimulating the advance zone of the melatonin PRC. Therefore, for an individual having an endogenous melatonin offset occurring at about CT 1, melatonin is optimally administered no later than at about CT 0, so that the rise overlaps (that is, occurs before) the offset. For this or any other preferred or desirable administration time for an exogenous melatonin dose, the duration of the exogenous melatonin pulse can be adjusted in order to optimize the magnitude of the phase delay. For administration at about CT 0, the duration of the melatonin dose is less than about 13 hours to avoid overlap of the fall of the exogenous dose with the onset of endogenous melatonin in the individual the next night. For individuals having an earlier endogenous offset (i.e., earlier than about CT 1, caused, for example, by early morning light exposure), exogenous melatonin is administered earlier than about CT 0. In this instance, the duration of the exogenous melatonin pulse can advantageously be longer than about 12 hours, provided the fall of the exogenous dose does not overlap the onset of the individual's endogenous melatonin production.

Alternatively, stimulating the maximal portion of the delay zone of the AUC of the melatonin PRC is useful for achieving a phase delay by an administration regime provided in the middle column of Table 1 for various immediate-release, sustained-release and combined immediate/sustained-release formulations. For example, melatonin can be administered at about CT 23 having a duration of less than or equal to about 7 hours, to avoid stimulation of the phase-advance zone of the melatonin PRC at about CT 6. A melatonin dose administered at about CT 23 and having a duration of up to 14 hours would be appropriate if a phase delay was achieved by the latest possible fall (while avoiding overlap with the endogenous onset).

Table 1 can also be used to calculate the proper administration time for an exogenous dose of any known (or predicted) duration. In this way, the circadian administration time can be optimized for any particular immediate- or sustained-release dose (or mixtures thereof). For example, a dose of melatonin having a 9-hour duration and administered to produce a phase delay is not administered after about CT 4 to avoid overlap with endogenous melatonin onset. Similarly, such a dose is not administered after about CT 21 to avoid stimulating the phase-advance zone of the AUC (i.e., from about CT 6 to about CT 18). In addition, melatonin is advantageously administered before about CT 0 so that the exogenous rise occurs prior to the endogenous offset. It is also advantageous to administer melatonin to produce plasma melatonin concentrations higher than endogenous levels during the interval when endogenous melatonin is produced.

The results obtained in Examples 2–5 were also used to construct a Table of times useful for maximizing the magnitude and extent of phase advances (Table 2). This Table begins at CT 6, since it is generally unwise to administer melatonin before this time to produce a phase advance. The middle column of this Table teaches overlap of the exogenous melatonin fall with endogenous melatonin onset for maximizing phase advances. The right-hand column teaches administering melatonin having a generally longer duration so that the maximal portion of the phase-advance zone of the area under the curve (AUC) is stimulated. The duration of plasma melatonin concentration taught in the right hand column of Table 2 are optimal, whereas the duration prescribed in the middle column of the Table is minimal. For any preferred or desirable administration time for an exogenous melatonin dose, the duration of the exogenous melatonin pulse can be adjusted in order to optimize the magnitude of the phase advance. For example, melatonin administered at about CT 10 advantageously has a duration of no less than about 4 hours and optimally about 8 hours.

Table 2 can also be used to calculate the proper administration time for an exogenous dose of known (or predicted) duration. Using the middle column of the Table, for example, a melatonin dose having a duration of about 7 hours is administered no earlier than about CT 7 (to overlap the endogenous onset at about CT 14). Similarly, a melatonin dose having a duration of about 3 hours is administered no earlier than about CT 11. In general, melatonin is administered at a time appropriate to ensure overlap between the exogenous fall and the endogenous onset, assuming the melatonin onset occurs at CT 14. In this way, the circadian administration time can be optimized for any particular IR or SR dose (or mixtures thereof) providing for overlap of the exogenous fall and the endogenous onset. Alternatively, the right-hand column of the Table is used to direct stimulation of the maximal portion of the AUC of the phase-advance zone of the melatonin PRC. For example, a dose having a duration of about 7 hours is optimally administered at about CT 7 rather than about CT 11, so as to stimulate the maximal portion of the of the phase-advance zone of the melatonin PRC, as well as to overlap the onset of endogenous melatonin production and to provide the earliest rise in exogenous melatonin levels.

EXAMPLE 7

Melatonin is often taken as a soporific agent. Frequently, a phase advance is also desired (i.e., the sleep phase is desired earlier than the individual's circadian rhythms dictate, due, for example, to transmeridional travel to the east). Melatonin's soporific effectiveness is thus two-fold: a phase advance in the sleep propensity rhythm can decrease, sleep latency, and a direct effect on sleep (often requiring a higher dose than required by the circadian rhythm phase shift) may also be produced by melatonin administration. Additionally, sleep can also help reset an individual's body clock by superimposing darkness upon the light/dark cycle. (Under any of these circumstances, however, a phase delay should be avoided.) However, in the event that melatonin causes instantaneous phase shifts, proper administration of melatonin can result in a phase advance in the sleep propensity rhythm (induced by giving melatonin in the beginning of the night), and in addition melatonin can be used to promote sleep maintenance by causing a phase delay in the sleep propensity rhythm by melatonin administration later in the night that stimulates the delay zone of the melatonin PRC. (Of course, melatonin stimulation of the delay zone should be avoided after sleep onset if the individual is having trouble awakening at the desired time.) This pattern of effect on sleep propensity and circadian rhythm phase shifting is advantageously achieved using a melatonin formulation comprising a sustained-release formulation, or alternatively, a combination of an immediate-release and a sustained- or delayed-release formulation.

If phase delays are to be avoided or minimized, the exogenous fall should be earlier than the endogenous offset, as well as to reduce stimulation of the AUC of the phase-delay zone of the melatonin PRC. Table 3 is constructed to optimize exogenous melatonin pulse duration to avoid the delay zone of the PRC. The middle column indicates the maximal duration of exogenous melatonin concentrations if the AUC strategy is not used (although, for phase advances, the fall should always precede the offset), whereas the right-hand column of the Table indicates the exogenous melatonin duration if the AUC strategy is used. If melatonin is taken at about CT 15, for example, and a phase delay is to be avoided, melatonin duration is not more than about nine hours to avoid a fall later than the offset, and is less than about three hours to avoid stimulation of the phase-delay zone of the melatonin PRC. When taking melatonin for its soporific effect, phase delays are avoided by not administering melatonin after about CT 17 (and at this time only if it has a one-hour duration), if the AUC strategy is used. Also, for some individuals who can benefit from melatonin's soporific effects, melatonin should be taken as early as possible so as to enhance phase delays; these include elderly people with sleep maintenance insomnia early morning awakening and other signs of abnormally phase-advanced circadian rhythms.

Sleep-time use of sedative-hypnotics and soporific (>1 mg) doses of melatonin can also be used alone or in combination with phase-shifting doses ($\leq 1$ mg) when direct soporific effects are needed in addition to the phase-shifting effects of low-dose daytime administration of melatonin.

EXAMPLE 8

Melatonin can also be administered to avoid a phase shift (for example, when melatonin is used specifically as a soporific). To achieve this result, melatonin is administered at preferred times and durations so that the rise of exogenous melatonin is the same number of hours earlier than the onset as the fall is later than the offset (as shown in Table 4). Table 4 assumes that the endogenous onset is about CT 14 and the offset is about CT 1, although it should be recognized that ambient light exposure will shorten the melatonin duration somewhat, delaying the onset and advancing the offset. Alternatively, melatonin is given at a time that provides stimulation of equal parts of the advance and delay zones of the melatonin PRC.

EXAMPLE 9
Jet Lag

The present invention and the teachings of U.S. Pat. Nos. 5,242,941 and 5,591,768 provide methods for the treatment of jet lag using melatonin administration. These teachings of this Example are primarily based on the area under the curve and overlap strategies and can be modified according to the teachings of the previous Examples. Table 5 provides preferred times for using light exposure to suppress endogenous melatonin production, when such endogenous melatonin production would otherwise cause a phase shift contrary to the direction of the desired phase shift. Table 5 teaches that light suppression of endogenous melatonin production will enhance a phase delay when exposure occurs between about CT 14 and about CT 18, and will enhance a phase advance when exposure occurs between about CT 18 and CT 1. These are also the preferred times when it would be advantageous to administer melatonin blockers. Table 5 also teaches times when additional hours of light exposure would benefit the desired phase shift on the first day of arrival and for subsequent days, whereby light exposure stimulates the light PRC. The Table describes two 12-hour intervals for light exposure, about CT 18 to about CT 6 for causing a phase delay and about CT 6 to about CT 18 for causing a phase advance. These are also the times that would be advantageous for administering melatonin inverse agonists and melatonin antagonists to achieve the phase shifts as indicated in the Table.

In addition, avoiding light exposure can reduce light suppression of endogenous melatonin production and thereby increase melatonin stimulation of the melatonin PRC. If appropriately timed, such endogenous melatonin stimulation will help with a desired phase shift. The present invention provides the use of avoiding light exposure for achieving a circadian rhythm phase shift. Table 6 provides an illustration of how avoiding light exposure on the first day after arrival and for subsequent days is used to affect circadian rhythm phase shifting for treating jet lag. The Table discloses preferred times that are particularly important for reducing light exposure to minimize light suppression of endogenous melatonin production and facilitate the desired phase shift. The Table also indicates the 12-hour intervals of each day when light exposure is reduced on the first day of arrival and for subsequent days that facilitates the desired phase shift by reducing stimulation of the light PRC. These 12-hour intervals of reduced light response (about CT 18 to about CT 6 for enhancing phase delays and about CT 6 to about CT 18 for enhancing phase advances) are also the times that are advantageously used for administration of exogenous melatonin, melatonin agonists and melatonin stimulants.

It will be understood that, in using these and other Tables herein which teach clock time administrations for shifting the body clock, the body clock can shift up to about 3–4 hours per day. To be conservative (that is, to avoid scheduling phase-shifting agents at the "wrong" time), the columns of these and other Tables change by one hour per day. However, an individual, particularly with treatment as disclosed by the invention, can shift more than one hour per day. The rate of phase-shifting for an individual can be simply monitored by using DLMO time (determined physiologically as described herein) or some other reliable circadian marker, to estimate how fast the circadian pacemaker is phase shifted over the course of treatment. Accordingly, an individual can "skip" the instructions on any given day and use the invention's instructions for the following day, or the day after that, etc. That is, instead of following instructions for Day 2 after arrival, one can follow them for Day 3, Day 4 or Day 5, depending on how fast one is phase shifting. For example, if one is shifting at the rate of two hours per day, then instructions for Day 3 should be substituted for Day 2 and instructions for Day 5 should be substituted for Day 3. If one is shifting faster, then instructions for Day 4 should be substituted for Day 2, etc. It will also be understood that Day 0 refers to the schedule before or during the day of travel. Individuals can monitor the rate of their phase shifting either by using the services of a physician or other clinical worker, or by using the "self-administered" tests (e.g., a melatonin dip-stick) as described above. However, one can usually assume that, if treated, phase shifting is going to occur at a rate of at least 2 hours per day.

One way to avoid bright light exposure is to sleep during the day ("taking a nap"). This behavior influences endogenous melatonin production by changing the pattern of light exposure experienced by a human and therefore influences the times and duration of endogenous melatonin production (because a nap will cause the biological clock to experience a dark pulse). Times of nap-taking are therefore important when considering circadian rhythm phase-shifting effects in a human. A tendency to nap is common in individuals experiencing transmeridional travel. Nap times are preferred when light exposure should be avoided or reduced, most particularly when the appropriate zone (advance or delay) of the melatonin PRC is advantageously stimulated by reducing light suppression of endogenous melatonin production. Table 6 indicates the times when napping advantageously has this effect on the endogenous melatonin PRC, as well as times when napping reduces stimulation of the light PRC by ambient light. Similarly, naps are to be avoided at certain times according to Table 5, particularly during times when it is desirable that endogenous melatonin production stimulates the appropriate zone of the melatonin PRC and most particularly when ambient light stimulates the appropriate zone of the light PRC. Of course, there may be other reasons to sleep that need to be taken into account. However, if an individual feels the need to sleep, Table 6 indicates the preferred times (to avoid stimulation by light of the light PRC) and most preferred times (to stimulate the melatonin PRC) to sleep.

Application of these teachings to alleviating the symptoms of jet lag are as follows. For a traveler going to Continental Europe from Portland, Oreg. (nine time zones to the east), a phase advance of 9 hours is required to re-entrain the traveler to local time and alleviate the symptoms of jet lag. For this traveler, light exposure {particularly bright artificial light or sunlight (which is brighter than indoor light)} preferably occurs between about 10 a.m. and about 10 p.m. Destination Time (DT). Light is particularly avoided in the morning before about 10 a.m. DT for the first day after arrival. This is the time when endogenous melatonin should not be suppressed by light, so that the absence of light (i.e., darkness) may facilitate (directly and indirectly) endogenous melatonin stimulation of the appropriate zone of the AUC of the melatonin PRC. (Indirect facilitation of melatonin's phase-shifting effects refers to simultaneous administration of darkness and melatonin having a mutually potentiating effect.) In other words, naps are preferably taken before about 10 a.m. DT and light exposure preferably occurs between about 10 a.m. and 10 p.m. DT. In addition, naps or prolonged darkness should be avoided between about 10 a.m. and 10 p.m. DT, and particularly between about 10 a.m. and 5 p.m. DT, because stimulation by endogenous melatonin at this time would stimulate the wrong zone of the melatonin PRC (the delay zone), and would thus work contrary to the desired 9-hour phase advance. Naps taken before about 10 a.m. are preferred, since this is also the time when light exposure should be avoided, and darkness at this time permits endogenous melatonin production to stimulate the appropriate (advance) zone of the melatonin PRC, thereby enhancing the desired 9-hour phase advance needed to adjust to the new time zone. For this traveler, napping after about 5 p.m. DT would be less likely to counteract the desired phase shift (since endogenous melatonin production will end at or before about this time). {However, it will be recognized that such evening naps might make it more difficult to fall asleep that night, and that light exposure between about 5 p.m. and about 10 p.m. may be helpful to enhance a phase advance by stimulating the appropriate (advance) zone of the light PRC.} For shorter trips to the east, or on subsequent days, these times are preferably moved earlier, as shown in more detail in Tables 5 and 6.

Tables 5 and 6 can also be used for prescribing times of bright light exposure and bright light avoidance for travelers making transmeridional trips to the west. For example, after the return trip to Portland (nine time zones to the west, requiring a 9-hour phase delay to re-entrain the traveler to local time and alleviate the symptoms of jet lag), Table 5 describes the times of nap avoidance and Table 6 describes the times of nap desirability. On the first day of arrival, naps should occur after about 4 p.m. DT, since light exposure is particularly undesirable before this time (with the same proviso as above that an evening nap might reduce sleep drive later in the night). Light exposure is avoided in general between about 4 p.m. and 4 a.m. DT for such a traveler. Naps are particularly avoided between about noon and about 4 p.m. DT, and light exposure is particularly desirable at this time, in order to suppress endogenous melatonin production. Light exposure is generally desirable for this traveler between about 4 a.m. and 4 p.m. DT. These times are shifted later for shorter trips and on subsequent days. Table 5 indicates the preferred times (to stimulate the light PRC) and most preferred times (to avoid stimulation of the melatonin PRC) to avoid sleep. These times need to be considered along with other considerations of sleep need and desirability, when scheduling sleep and nap times.

Alternatively, if naps are not taken at the appropriate times, light exposure may be reduced by the use of goggles, as previously described (see U.S. Pat. No. 5,591,768, incorporated by reference). The preferred times for obtaining light (Table 5) and avoiding light (Table 6) regarding the effects of light on endogenous melatonin production are also the times of the most sensitive (robust) parts of the light PRC. Avoiding light exposure at certain times after travel is important for avoiding re-entrainment by partition, that is, shifting the body clock in the opposite direction as traveled (which often results in the sleep/wake cycle shifting in one direction and the other circadian rhythms shifting in the other direction). Avoiding and obtaining light exposure may also be important for suppressing endogenous melatonin production.

Selective reduction of endogenous melatonin production during either the advance zone or the delay zone of the melatonin PRC is also achieved by the use of beta-blockers (or other pharmacological agents that reduce endogenous melatonin production or otherwise limit binding of melatonin to melatonin receptors). Preferred administration times for using beta-blockers to effect circadian rhythm phase shifting are provided in Table 7. For example, when traveling east nine time zones, a beta-blocker having a duration of about 7 hours is advantageously taken at about 10 a.m. DT upon the first day of arrival, thereby reducing endogenous melatonin production until about 5 p.m. DT. Timing of beta-blocker administration is earlier than about 10 a.m. for shorter trips (and on subsequent days) when traveling east, as shown in Table 7. For earlier administration times (which may prove inconvenient), a delayed-release (DR) form can be taken at bedtime rather than in the middle of the night to avoid interference with sleep. For travel nine time zones to the west, beta-blockers are taken at about 11 a.m. DT upon arrival. This time should be later for shorter trips, and on subsequent days (see Table 7). For traveling west, beta-blockers of four-hour duration are useful and can also be taken according to Table 7. This Table assumes no delay in the onset of action. This Table can be appropriately modified if the duration of action of the beta-blocker is different than seven hours (for eastward travel) or four hours (for westward travel) or if the onset of melatonin activity is not immediate. When going east, durations greater than 7 hours are acceptable; however, the duration should not be so great that it inhibits endogenous melatonin production in the beginning of the next night (this would reduce endogenous melatonin stimulation of the advance zone of the melatonin PRC), unless complete inhibition of endogenous melatonin production is desired. (Inhibition of the entire endogenous melatonin profile in some individuals might enhance phase shifting in either direction.) For facilitating phase advances, beta-blockers of longer duration are not necessary and should be taken earlier, ending at about CT 18; they should not be taken earlier than about CT 6, except with a DR formulation, unless complete inhibition of endogenous melatonin production is desired. When going west (requiring a phase delay), durations of greater than 4 hours are acceptable: for every hour of duration greater than 4 hours, the beta-blocker should be administered one hour earlier than is suggested in Table 7, or an appropriate DR formulation should be used. For facilitating phase delays, beta-blockers should ideally be about 4 hours in duration. However, administration should not occur when endogenous melatonin might stimulate the delay zone of the melatonin PRC, unless complete inhibition of endogenous-melatonin production is desired. Beta-blockers can be taken for a few days before travel and during the day of travel; these times are indicated in Table 7 in the rows designated 0 time zones and are given in Embarkation Time (E.T.).

Table 9 illustrates preferred melatonin administration duration times when taking more than about 1 mg at bedtime for alleviating jet lag according to the melatonin PRC. For example, for travel nine time zones to the east (requiring a phase advance), melatonin administration is disadvantageous prior to about 10 p.m. DT. A DR formulation may be necessary if one goes to bed earlier than 10 p.m. DT, which is very common on the plane or after a night of relative sleep deprivation on the plane. The duration of exogenously-administered melatonin should be at least nine hours to permit overlap of the fall with the onset and to maximize the extent of phase-shifting. However, melatonin duration should not be more than 12 hours, in order to avoid stimulating the delay zone of the melatonin PRC, unless the soporific effect during sleep times is more desirable. (Providing the latest possible fall before the next night's endogenous melatonin onset requires a longer duration.) As the melatonin PRC shifts on subsequent days, the dosage is reduced, or the duration shortened in other ways to avoid stimulation of the delay zone or to produce a fall later than the endogenous melatonin offset. Melatonin administration in the middle of the night (about 0.5–3 mg, preferably achieved using DR formulations) can be used to help sleep maintenance, but should not be taken after about 5 a.m. D.T. (see Table 8 for preferred administration times), unless the soporific effect during sleep times is more desirable. (Providing the latest possible fall before the next night's endogenous melatonin onset requires a longer duration.) This time should be moved earlier, on subsequent days and for shorter trips to the east.

For an individual traveling nine time zones to the west (which requires a phase delay of nine hours to re-synchronize the traveler to local time), melatonin administration at a dosage of 3 mg in an immediate-release dosage form (or a dose of this order of magnitude) taken at bedtime will coincidentally be helpful in causing both sleep as well as having a phase-shifting effect on the delay zone. For this administration regime, the exogenous melatonin rise precedes, and the fall occurs later than, the endogenous melatonin offset. For subsequent days, a set of SR formulations having increasingly longer durations are useful for facilitating the required phase delay (see Table 9). After a few days, formulations having longer durations (to selectively stimulate more of the delay zone of the melatonin PRC) advantageously are used to counter any inadvertent phase advance occurring if melatonin is taken too early during the advance zone of the melatonin PRC (i.e., before the endogenous melatonin onset), and also by causing a later fall. Alternatively, an administration regimen of low-dose SR melatonin formulation (e.g., having a 12-hour duration) taken at increasingly later times or combined with a DR formulation (see Table 10 for preferred administration times) can be used to effect the required phase delay using a bedtime administration protocol to produce a fall later than the endogenous offset. Also, melatonin duration may be higher if the soporific effect during sleep times is more desirable.

However, for travel less than three time zones west, bedtime administration is the wrong time, unless a very long SR formulation is taken that can cause a more potent phase delay by extending the new offset, or a low-dose (non-soporific) melatonin formulation is taken having a 12-hour duration and administered with a 1–3 hour DR component (see Table 10).

Melatonin administration before or on the day of travel can also be advantageous in some circumstances, and the desirability of administering low-dose and high-dose formulations depends in part on whether one intends to sleep on the plane and can take melatonin at a time given as the zero time in Table 6. However, under most circumstances melatonin administration is disadvantageous prior to 1 a.m. ET when going west or after 1 a.m. ET when going east, unless the soporific effect during sleep times is more desirable. To enhance a phase advance (required for eastward travel), melatonin is taken to stimulate the advance zone of the melatonin PRC (between about CT 6 and about CT 18), and to enhance a phase delay (required for westward travel), melatonin is taken to stimulate the delay zone of the melatonin PRC (between about CT 18 and about CT 6 or longer for some individuals). In addition, melatonin administration is advantageously accompanied by concomitant darkness for several hours. Melatonin agonists and stimulants can also be taken before travel at the same times as described for melatonin. Melatonin inverse agonists or melatonin antagonists are taken to stimulate the opposite zone, as described for melatonin, of the melatonin PRC (see Table 5). Table 5 also indicates when to take a melatonin blocker to suppress endogenous melatonin production. Light and dark can also be used as described before travel, but may interfere with sleep and wakefulness (see the row for 0 time zones in Tables 5 and 6).

Dosage forms comprising about 0.5 mg to about 3 mg of melatonin (or a dose of these orders of magnitude) are advantageously used for effecting phase shifting for. alleviating the symptoms of jet lag, as described in U.S. Pat. Nos. 5,242,941 and 5,591,768 (incorporated by reference). However, melatonin is taken no earlier than certain times, depending on the number of time zones crossed and the number of days after arrival (see Table 11 for preferred administration times), unless the soporific effect during sleep times is more desirable. For example, after traveling nine time zones to the west (requiring a phase delay), a 0.5 mg dose of melatonin is taken no earlier than about 4 p.m. DT, with later administration times prescribed for subsequent days. When traveling east, the approximate dose of 0.5 mg of melatonin can be taken in the middle of the night, following a low-to-moderate dose IR formulation, if one awakens after sleep onset. However, middle-of-the-night melatonin administration is not taken so late at night that it will stimulate the inappropriate zone of the melatonin PRC (for example, after about 5 a.m. DT the first day following a trip through nine time zones to the west; see Table 8).

A complication arises if an air traveler has not completely adjusted to the new time zone, especially when such a traveler returns to the embarkation point or other destination before complete synchrony has been achieved with local time of the first destination. This situation is illustrated as follows. If an individual has traveled 8 time zones to the east and stayed four days without using any schedule of light exposure or avoidance and without using any exogenous melatonin administration to speed adjustment, this individual will typically have shifted about 4 hours (instead of the 8 required for complete adjustment to the new time zone), since it takes at least about one day to shift about one hour without using any special techniques to enhance phase shifting. Upon returning to the west, this individual will need to adjust only 4 hours back to the original circadian phase. In this case, the Tables and teachings of the present invention are used by applying the schedule for a westward time zone difference of 4 hours, even though the traveler has crossed through 8 time zones.

Another way to treat such partial phase shifts is to consider the teachings of Tables 5–11 in terms of circadian time. These Tables are based on the assumption that CT 14 is about 9 p.m. for most people. For individuals who have not completely adjusted to a new time zone, however, this will not be the case. For example, an individual who has only half adjusted to an 8 hour trip to the east will typically have a DLMO at about 1 a.m. For example, in Table 5, when returning 8 time zones to the west, light exposure is obtained between about 9 a.m. and about 9 p.m. on Day 1 (since 1 a.m. is 4 hours later than 9 p.m., the times in the Table should be adjusted to be about 4 hours later). This adjustment can be made because, according to Table 5, in order to obtain a phase delay the light PRC is stimulated between about CT 6 and about CT 18 and endogenous melatonin stimulation of the melatonin PRC is suppressed by light exposure between about CT 14 and about CT 18. Table 5 was constructed using an algorithm for obtaining a phase delay by administering a melatonin antagonist or melatonin inverse agonist between about CT 6 and about CT 18 (which is also the time interval when light exposure will enhance a phase delay according to the light PRC), as well as by administering a compound that blocks endogenous melatonin production between about CT 14 and about CT 18; this is also the time interval when light exposure will enhance a phase delay, in part by suppressing endogenous melatonin production. Table 5 was also constructed using an algorithm for obtaining a phase advance by administering a melatonin antagonist or melatonin inverse agonist between about CT 18 and about CT 6 (which is also the time interval when light exposure will enhance a phase advance according to the light PRC), as well as by administering a compound that blocks endogenous melatonin production between about CT 18 and about CT 1; this is also the time when light exposure will enhance a phase advance, in part by suppressing endogenous melatonin production. Table 6 was constructed using an algorithm for obtaining a phase advance by administering melatonin, a melatonin agonist or a compound that stimulates endogenous melatonin production between about CT 6 and about CT 18, which is also the time interval when avoiding light exposure will enhance a phase advance according to the light PRC (from about CT 14 to about CT 18 is also the time interval when avoiding light exposure will enhance a phase advance by reducing suppression of endogenous melatonin production by light). Table 6 was also constructed using an algorithm for obtaining a phase delay by administering melatonin, a melatonin agonist or a compound that stimulates endogenous melatonin production between about CT 18 and about CT 6 (which is also the time interval when avoiding light exposure will enhance a phase delay according to the light PRC; from about CT 18 to about CT 1 is also the time interval when avoiding light exposure will enhance a phase delay by reducing suppression of endogenous melatonin production by light).

As disclosed above, beta-blocker administration can also be used to affect re-synchronization of circadian rhythms following transmeridional travel, as shown in Table 7. A beta-blocker is administered to block endogenous melatonin production between about CT 14 and about CT 18 to facilitate a phase delay, and between about CT 18 and about CT 1 to facilitate a phase advance. For Table 8, phase advances are enhanced by providing that middle-of-the-night melatonin not be administered after about CT 18, for enhancing a phase advance. Table 9 was constructed on the assumption that when melatonin is taken at bedtime (about 9 p.m.), it is advantageous to delay melatonin activity until after about CT 18 when traveling west (and to avoid melatonin activity between about CT 6 and about CT 18, which would stimulate a disadvantageous phase advance), and to ensure that melatonin activity ceases before about CT 18 when traveling east (and to provide melatonin stimulation of the greatest extent of the area under the curve between about CT 6 and about CT 18).

In Table 10, melatonin activity is maximal between about CT 18 and CT 6 to achieve a phase delay, and melatonin activity occurs between about CT 6 and about CT 18 to achieve a phase advance. Table 11 is provided for a melatonin formulation having a duration of about 5 hours, wherein, to achieve a phase delay, melatonin is administered no earlier than about CT 18. It will be understood that the algorithmic bases of these Tables are adjusted to account for incomplete circadian phase adjustments following air travel, and for individuals whose DLMO times are not 9 p.m.

In addition, it will be recognized that there are circumstances when it is desirable to achieve a phase shift after transmeridional travel whereby the phase shift is opposite to that of the direction of travel, i.e., when one would rather advance than delay, or (more likely) delay rather than advance. This non-intuitive principle is particularly pronounced with regard to phase delays. For example, a phase delay of 14 hours is generally preferable to a phase advance of 10 hours after eastward travel across ten time zones. The methods and teachings of this invention can be used to achieve a phase delay rather than a phase advance in such circumstances. Finally, melatonin, melatonin agonists, antagonists, inverse agonists and compounds that enhance or diminish endogenous melatonin production can be advantageously combined with a sedative/hypnotic of appropriate pharmacological activity and duration or a high-dose melatonin formulation (>1 mg) to be administered at a time whereby sleep loss is reduced during adjustment to the destination time zone.

EXAMPLE 10

Human Sleep Phase Disorders

Delayed sleep phase syndrome (DSPS) is characterized by difficulty falling asleep and difficulty waking up in the morning. In general, individuals suffering from DSPS need to have their circadian rhythms, including the melatonin circadian rhythm, gradually shifted earlier (i.e., phase advanced) by about 2–6 hours. DSPS can be treated with morning light exposure. According to the melatonin PRC, this magnitude of phase advance requires melatonin administration between about CT 6 and about CT 11. Assuming awakening at about 10 a.m. (which would equal about CT 0), exogenous melatonin would be administered between about 4 p.m. and about 9 p.m. According to the invention disclosed in U.S. Pat. No. 5,591,768 (incorporated by reference), the clock time of administration is shifted earlier each day, on the order of about 15–30 minutes, to keep the phase relationship between the time of administration and DLMO constant. The instant invention teaches that the fall of exogenous melatonin is timed to overlap the onset of endogenous melatonin and continues through the advance zone of the melatonin PRC. In an individual who awakens at about 10 a.m., endogenous melatonin onset typically occurs at about midnight. In order for the fall to overlap this onset, therefore, the duration of the exogenous melatonin pulse (administered at about 6 p.m.) is at least about six hours; however, to stimulate all of the advance zone of the melatonin PRC, the duration extends to about 4 a.m. and is be no more than about ten hours in duration, to avoid stimulation of any part of the delay zone of the AUC of the melatonin PRC. These times are shifted earlier on successive days until the desired sleep time is reached, at a rate dependent on how fast the individual is advancing their circadian rhythms (usually 15–30 minutes per day). A preferred formulation provides a low dose of melatonin for the first few hours after administration followed by rising melatonin levels (about six-fold) at about CT 15 to take advantage of any direct soporific effect of melatonin (since CT 16 typically corresponds to bed-time). A melatonin formulation can be combined with a short-acting sedative/hypnotic medication to treat patients with DSPS. Also, in view of the fact that every American experiences a transient DSPS when adjusting to Daylight Savings Time, the methods of this invention encompass methods for alleviating these acute circadian rhythm phase disorders associated with changing from Standard Time to Daylight Savings Time.

Advanced sleep phase syndrome (ASPS) is characterized by difficulty staying awake in the evening and difficulty maintaining sleep in the morning. ASPS can be treated with evening light exposure. According to the melatonin PRC as taught by U.S. Pat. No. 5,591,768, exogenous melatonin is administered immediately upon awakening (i.e., at about CT 0) to cause a phase delay that does not require awakening during the night to take the formulation. Alternatively, a DR formulation is administered that is formulated to increase melatonin levels at about CT 18 and continue through about CT 6 (to stimulate the AUC of the delay zone of the melatonin PRC and to avoid stimulating the advance zone of the melatonin PRC) or through about CT 13 (to produce the latest time of exogenous melatonin fall that does not overlap the onset of endogenous melatonin the next night). Additionally, administration times are shifted later each day, by about 15–30 minutes, as awakening times gradually shift to later clock times according to the teachings of U.S. Pat. No. 5,591,768. The instant invention teaches that melatonin is administered before about CT 1 and that the duration of elevated plasma melatonin concentration administered at about CT 1 is at least about five hours, in order to have exogenous melatonin production be continuous with the endogenous melatonin profile and to stimulate the remaining AUC of the delay zone of the melatonin PRC. Using another strategy, exogenous melatonin duration is advantageously about 13 hours (taken at about CT 0) to selectively stimulate the maximal portion of the AUC of the delay zone of the melatonin PRC and to provide a maximally delayed fall that does not overlap the next night's endogenous onset. Low-dose melatonin administration is important to avoid daytime sleepiness for administration times affecting plasma melatonin concentrations during an individual's day. In view of these considerations, a sustained-release formulation is preferred for treating ASPS. Longer-acting sedative/hypnotics or short-acting sedative/hypnotics with a delayed-release component can be taken with melatonin in the treatment of ASPS. Also, in view of the fact that every American experiences a transient ASPS when adjusting to Standard Time from Daylight Savings Time, the methods of this invention encompass methods for alleviating these acute circadian-rhythm phase disorders associated with changing from Daylight Savings Time to Standard Time. Melatonin agonists and stimulants can be substituted for melatonin, accompanied by reduced light exposure; melatonin antagonists and inverse agonists can be given during the opposite zone of the melatonin PRC as recommended for melatonin, accompanied by light exposure; and melatonin blockers can be given during the opposite zone of the melatonin PRC as recommended for melatonin, accompanied by light exposure, that also coincides with the endogenous melatonin profile, as described in Example 9.

Mixed ASPS/DSPS sleep disorders are characterized by those individuals who have trouble falling asleep and staying asleep. These individuals are advantageously administered exogenous melatonin so that the exogenous rise precedes the endogenous onset and melatonin stimulates the AUC of the advance zone of the melatonin PRC, having plasma melatonin concentration levels increase at about CT 15 to induce sleep, and then providing high plasma melatonin levels until desired wake-up time (stimulating the AUC of the delay zone of the melatonin PRC) to delay sleep propensity, and providing a drop-off in levels as quickly as possible slightly before or around sleep offset.

EXAMPLE 11

Winter Depression

Winter depression can be treated by achieving a circadian rhythm phase shift using exogenous melatonin administration. In winter depression, most patients are thought to be abnormally phase delayed when depressed in the winter. According to the melatonin PRC as taught by U.S. Pat. No. 5,242,941, exogenous melatonin is administered in the afternoon or early evening, in order to provide a corrective phase advance. According to the teachings of U.S. Pat. No. 5,591,768, administration clock times are shifted earlier by about one hour after about one week of treatment, in order to stimulate the same point on the melatonin PRC after the melatonin PRC has shifted as a result of exogenous melatonin treatment; in this way, the phase relationship between melatonin administration and the melatonin PRC is maintained. In addition, it has been determined that individuals with winter depression are extremely sensitive to the soporific effects of melatonin. Consequently, the lowest possible dose (about 0.025 to about 0.25 mg) is administered. Only a sustained-release formulation (or repeated administration of low-dose immediate release formulations) can provide a sufficiently long duration of a such dose of melatonin so that the exogenous melatonin fall is later than the endogenous melatonin onset (at about CT 14). Thus, in order to treat winter depression by causing an optimal phase advance, the lowest possible dose is used with extremely careful timing of its rise and fall, so that the rise occurs as early as about CT 6 or about CT 8, the fall overlaps the endogenous onset, and the maximal portion of the AUC of the advance zone of the melatonin PRC is stimulated (the end of which is as late as about CT 18), while stimulation of the delay zone of the melatonin PRC is avoided. Such low-dose SR formulations preferably have a duration of about 11–12 hours.

Patients with winter depression were treated with either melatonin (N=5) or placebo (N=5). All subjects were screened prior to being admitted into the study and met the following criteria: 1) the DSM-IV criteria (American Psychiatric Association, 1994) for moderate to severe major depressive disorder (without psychotic episodes) or bipolar disorder (depressed or not otherwise specified) with a winter type seasonal pattern; 2) scored $\leq 20$ on the Structured Interview Guide for the Hamilton Depression Rating Scale Seasonal Affective Disorder Version (SIGH-SAD) (Williams et al., 1994, *Structured Interview Guide for the Hamilton Depression Scale-Seasonal Effective Disorder Version* (*SIGH-SAD*), New York: New York State Psychiatric Institute) with Hamilton Depression Scale (HAM-D) (Hamilton, 1967, *Brit. J. Soc. Clin. Psychol.* 6: 278–296) $\leq 10$ and an atypical score $\leq 5$ (Terman et al., 1990, *Neuropsychopharmacol.* 2: 1–22); 3) reported that a depression developed during the fall or winter and remitted the following spring for at least the two preceding years; 4) were in good physical health; 5) were not suicidal; 6) were not using psychotropic medications for the prior four weeks or other medications that interfered with endogenous melatonin production; 7) did not have other serious psychiatric, medical illnesses or sleep disorders; and 8) were not working a night shift schedule.

Prior to inclusion in the study, subjects were interviewed by a physician and also completed 7 a health and sleep screening questionnaire. Written informed consent was obtained for all participants.

The study was a three-week, parallel-group design, consisting of a pre-treatment assessment followed by three treatment weeks. Subjects were randomly assigned to either a melatonin or placebo group and were counter balanced based on their initial depression scores (SIGH-SAD) and their reported awakening times. Each group received melatonin or placebo in two daily capsules at about CT 8 and about CT 12, estimated from each subject's initial reported awakening time (about CT 0). The dose of melatonin was 0.125 mg per capsule.

For behavioral ratings, subjects were initially interviewed face-to-face using the 29-item Structured Interview Guide for the Hamilton Depression Rating Scale—Seasonal Affective Disorder version (SIGH-SAD). Two subsequent interviews were done weekly by telephone and the third and final interview was conducted in person. All interviews were conducted by a researcher blind to treatment conditions.

For the three-week period, subjects completed a Likert daily rating form and a daily sleep diary. To specifically assess fatigue associated with the capsule, subjects also completed a Profile of Mood States (POMS) 30 minutes after ingestion of each capsule. In addition, pre-study and weekly expectations questionnaires were completed.

Ten patients (9 females) with winter depression were admitted into the study. The mean age of the melatonin group was 37 (SD=13.6; range: 22–58) and the placebo group was 32.2 (SD=8.6; range: 22–42). The mean pre-treatment SIGH-SAD score for the placebo group was 29.4; the melatonin group mean was 29.2. The initial reported mean wake up time for the placebo group was 7:12 AM; the melatonin group mean was 7:20 AM. Two subjects in the melatonin group dropped out of the study after the second week of treatment, because of interfering school constraints. Therefore, the sample size for the third week was too small to be included in the analyses, although it should be mentioned that the means for the third treatment week were identical to those of the first two treatment weeks (mean changes in depression ratings occurred during the first week of treatment and remained constant through the end of the study).

Figure 7:
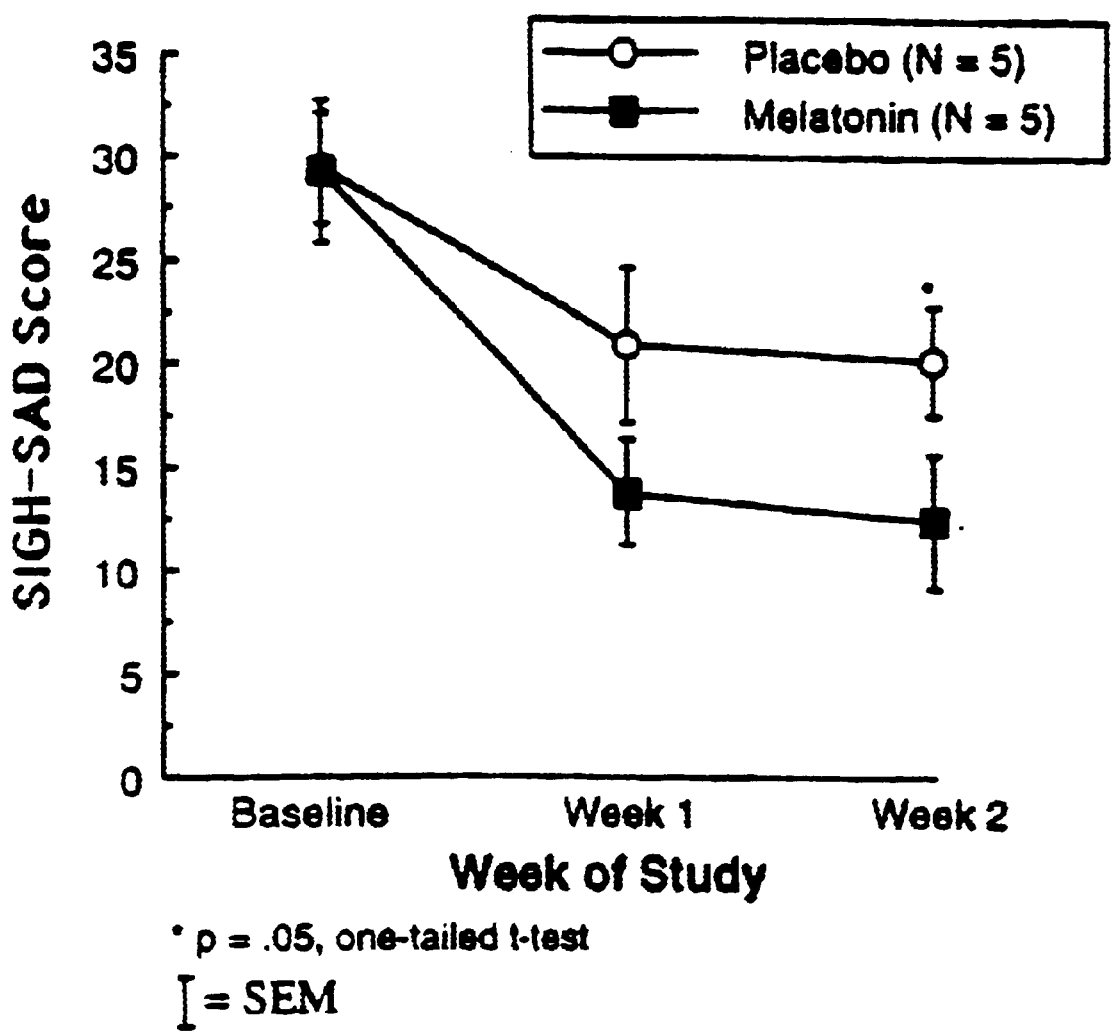
FIG. 7 describes the changes in depression ratings in patients with winter depression in response to melatonin treatment compared to placebo, as disclosed in Example 11.
Figure 8:
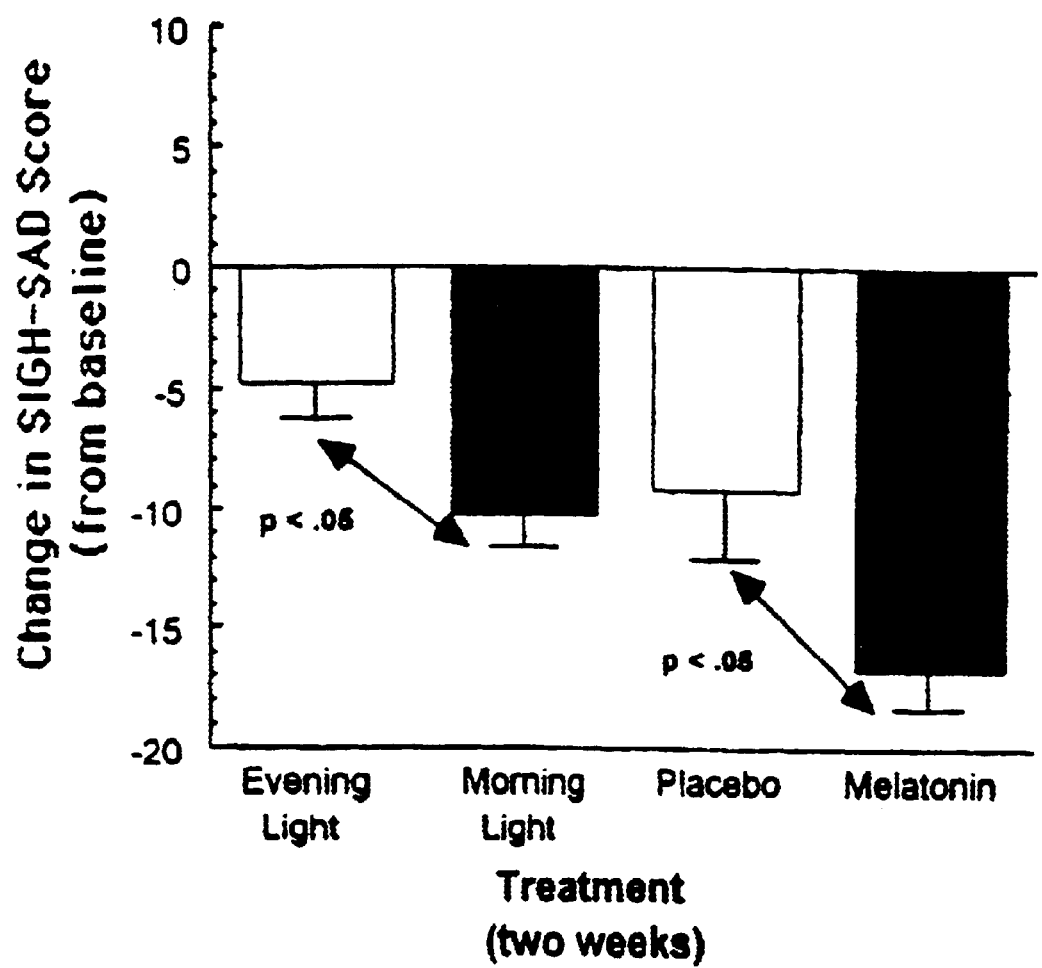
FIG. 8 describes the changes in depression ratings in patients with winter depression in response to melatonin or light treatment compared to placebo, as disclosed in Example 11.

A two-way repeated measures ANOVA using treatment group (melatonin and placebo) as a grouping factor and week (pre-treatment and at Week 2) as the repeated measure showed a main effect for week (p<0.0001) and a significant (week*group) interaction (p=0.049). A one-tailed, unpaired t-test for SIGH-SAD scores after two weeks of capsules revealed a significant difference (p=0.05) between the melatonin and placebo groups (see FIG. 7). Unpaired t-tests for change scores from pre-treatment to Weeks One and Two showed significant differences between the groups (p<0.05). These scores were 15.4 in Week 1 for the group administered melatonin (Standard Error of the Mean=2:18) and 8.4 for the group administered-placebo (S.E.M.=2.04). For Week 2 of treatment, the scores were 16.8 for the melatonin group (S.E.M.=1.5) and 9.2 for the placebo group (S.E.M.=2.91). By classifying subjects into non-responders and responders using the criteria of 39% or greater decrease in SIGH-SAD ratings to a score of 21 or less, there was only one responder in the placebo group, whereas all five subjects responded to melatonin (p=0.048, Fisher's Exact test).

These data indicate that melatonin can be used to treat winter depression. Remarkably, this melatonin regimen seems to be as effective by some, if not all measures, as morning light exposure, the current treatment of choice. (The treatment of choice for winter depression has been morning bright light exposure which causes a corrective phase advance.) In the present study, the melatonin dose was lowered to minimize soporific side effects that can be interpreted by the patient as symptoms of their disease. Normally, such a low dose is not expected to cause much of a phase advance. However, by giving the first dose at about CT 8 the phase-advancing properties of melatonin are enhanced according to our invention, provided that its duration was continuous with the endogenous melatonin onset. Such durations were achieved by a second immediate release melatonin administration given at about CT 12. The two doses also provide for near-maximal stimulation of the AUC of the advance zone of the melatonin PRC. For perhaps both of these reasons, an appropriate phase advance can be reasonably expected using this regimen. In addition, soporific side effects are avoided using this low dosage form. These data clearly indicate that the optimal melatonin treatment for winter depression is administration of the lowest possible dose in a SR formulation, beginning shortly after about CT 6 and extending to between about CT 14 and about CT 18, provided that the administered dose at the same time avoids soporific side effects before bedtime. The same treatment regimen can be applied to the treatment of any phase-delay disorder, including but not limited to subsyndromal winter depression and delayed sleep phase syndrome, even in its mildest form in which an individual has trouble falling asleep and waking up alert at the desired time. Melatonin can be given alone, in combination with morning bright light exposure and in combination with a melatonin blocker, such as a beta-blocker, to reduce endogenous melatonin production throughout the night or primarily during the delay zone of the melatonin PRC. Melatonin agonists and stimulants can be substituted for melatonin, accompanied by reduced light exposure; melatonin antagonists and inverse agonists can be given during the opposite zone of the melatonin PRC as recommended for melatonin, accompanied by light exposure, as described in Example 9.

EXAMPLE 12

Shift Work

Shift work produces circadian rhythm phase disorders in workers required to periodically change working hours. For workers changing to a later shift (for example, from a day shift (8 a.m. to 4 p.m.) to an evening shift (4 p.m. to 12 a.m.)), the invention disclosed in U.S. Pat. No. 5,242,941 describes melatonin administration on the delay zone of the melatonin PRC (i.e., between about CT 18 and CT 6). According to the teachings of U.S. Pat. No. 5,591,768, delay-specific administration of exogenous melatonin is performed at a later clock time on each day over a course of treatment (typically, about 4–6 days, the number of days during the work week). According to the instant invention, exogenous melatonin is administered at about CT 18 (about 1 a.m.), in order to selectively stimulate most of the delay zone. Melatonin can also be given at this time, advantageously before shifting the sleep/wake schedule (appearing in Row Day 0). Melatonin formulations administered at about CT 18 preferably have a duration of about 12 hours, in order to stimulate all of the delay zone. For some individuals, the latest possible fall may be more effective in causing a phase delay than avoiding stimulating any portion of the AUC of the advance zone of the melatonin PRC (as long as the fall ends before that night's onset). In this case, the duration of increased exogenous melatonin plasma concentration is optimally longer, about 19 hours. Whatever time of administration is chosen, however, the exogenous melatonin rise precedes and the fall occurs after the endogenous melatonin offset to create a circadian rhythm phase-delaying effect. An optimal modality for administering melatonin under these circumstances is a SR formulation, so that a lower dose can be used to avoid sleepiness until about 9 a.m. (when night workers usually go to bed). In addition, over the last few days of a treatment period, DR formulations having a delay of up to about 4 hours can be administered, allowing the capsule to be taken no later than bedtime, i.e., around 9 a.m. (see Table 12 for preferred administration times).

To be conservative (that is, to avoid scheduling phase-shifting agents at the "wrong" time), the columns of these and other Tables change by one hour per day. However, an individual, particularly with treatment as disclosed by the invention, can shift more than one hour per day. The rate of phase-shifting for an individual can be simply monitored by using DLMO time (determined physiologically as described herein) or some other reliable circadian marker, to estimate how fast the circadian pacemaker is phase shifted over the course of treatment. Accordingly, for some individuals who shift more quickly than average, the suggested administration time for Day 3 can be substituted for Day 2, Day 5 for Day 3, etc. For those individuals who shift even more quickly, Day 4 and be substituted for Day 2, Day 6 for Day 3, etc. Individuals can monitor the rate of their phase shifting either by using the services of a physician or other clinical worker, or by using the "self-administered" tests (e.g., a melatonin dip-stick) as described above. However, one can usually assume that, if treated, phase shifting is going to occur at a rate of at least 1–2 hours per day.

For treatment embodiments comprising beta-blockers (or any pharmacologic means of reducing melatonin production or blocking SCN melatonin receptors), the drugs are taken at about 9 p.m., and then at successively later clock times until about 9 a.m., and are taken only in formulations having a duration of less than about four hours (see Table 13 for preferred administration times). Beta-blockers having durations longer than about 4 hours can be used according to modification of the instructions comprising the Tables. For example, a beta-blocker with a 12-hour duration and used for delaying to the night-work schedule is taken on Day 1 at about 1 p.m. to avoid reducing endogenous melatonin production on any part of the delay zone of the melatonin PRC, while still reducing endogenous melatonin stimulation of the advance zone of the melatonin PRC. Of course, this means that the beta-blocker is also taken when, at least in part, no endogenous melatonin production is occurring; therefore, a four-hour duration is preferable. However, beta-blockade should not occur when endogenous melatonin might stimulate the delay zone of the melatonin PRC unless complete inhibition of endogenous melatonin production is desired. For facilitating phase delays, beta-blocker formulations having shorter duration times are advantageously administered at earlier times, to end at about CT 18; however, they should not be taken earlier than about CT 6, except for DR formulations, unless complete inhibition of endogenous melatonin production is desired (which might enhance phase shifting).

Alternatively, shift workers can advance the phase of their circadian rhythms to the nighttime work schedule. To do this, the instant invention teaches administration of exogenous melatonin in a sustained-release formulation having about a 12-hour duration and an administration time of about 9 a.m. (bedtime). However for the first few days of treatment, a delayed-release/sustained-release formulation is given in which levels substantially rise four hours after bedtime administration on the first day, with decreasing delays on subsequent days. After this initial delayed-release regimen, a SR formulation should be taken at successively earlier administration clock times (see Table 14 for preferred-administration times). Treatment regimes using beta-blockers (having a seven-hour duration) prescribe drugs administration at 1 a.m. and then at successively earlier administration clock times. At the endpoint of treatment, beta-blockers are taken at about 9 a.m. (bedtime) with the delayed-release interval decreasing from about 7 to about 5 hours (see Table 15 for preferred administration times). The delayed-release interval is needed to avoid getting up during the daytime sleep period. For facilitating phase advances, beta-blockers ideally have about seven hours duration, unless complete inhibition of melatonin endogenous is desired (which might enhance phase shifting).

When shifting back to the off-work week, a phase advance is sometimes preferred. According to the melatonin PRC taught in U.S. Pat. No. 5,242,941, this can be achieved by exogenous melatonin administration at about 1 a.m., assuming that the circadian rhythms have completely adapted to the 12-hour phase shift during the previous week. Consequently, a DR formulation would be essential, because taking melatonin at bedtime might stimulate part of the delay zone of the melatonin PRC (contrary to the desired phase advance). Preferred administration times for a delayed-release formulation set to release melatonin four hours after the final administration, in order to stimulate the advance zone of the melatonin PRC, are shown in Table 16. Sustained-release formulations are also preferred to provide low melatonin plasma levels at the end of the pulse to avoid the soporific effects of melatonin. After a few days of treatment, the SR formulation would not need the DR component and would be taken at times successively earlier. Beta-blockers can be taken at 1 p.m. and then successively earlier (see Table 17 for preferred administration times), preferably having a duration of about 7 hours. For the last few days, beta-blocker are taken having a DR component, set to produce a substantial rise in beta-blocker levels at about 9 hours after administration and then having decreasing delayed-release intervals on subsequent days, ending with a delayed administration time of about 5 hours on Day 12. This regime is constructed to avoid the need to wake up to take a formulation (which would interfere with sleep). Beta-blocker formulations preferably have a duration of less than about 12 hours, unless complete inhibition of endogenous melatonin production is desired.

Some shift workers prefer to delay to the off-work week. These workers take a 12-hour SR melatonin formulation at about 1 p.m. on the first day and then successively later. For the last few days of the treatment regime, preferred melatonin administration times are held constant at about 9 p.m. with successively longer DR components, until melatonin is administered having about a 3-hour delayed-release interval on Day 12 (see Table 18 for preferred administration times). This is done to avoid having to wake up to take a formulation (which would interfere with sleep). Beta-blockers of at least about 7 but not more than about 12 hours duration should be taken at about 9 a.m. and then successively later until about 9 p.m. on Day 12, or the last day of administration if re-setting is completed sooner (see Table 19 for preferred administration times). Beta-blockers should never be taken with a duration of more than 12 hours, unless complete inhibition of endogenous melatonin production is desired.

For shift workers who have not adjusted completely or for some other reason do not start the work week or off-work week with a baseline DLMO of 9 p.m., the teachings of Tables 12–19 are modified or the appropriate algorithm for each Table used to determine the appropriate melatonin administration time. If the worker has not completely shifted 12 hours by the end of the work week, one would start on the appropriate row of the appropriate Table (the same thinking applies to the shift worker who has not completely adjusted to the off-work schedule when using the work week Tables). For Tables 12 and 18, melatonin having an about 12-hour duration is administered to cause elevated plasma melatonin concentrations between about CT 18 and about CT 6 to achieve a phase delay. For Tables 14 and 16, melatonin having an about 12-hour duration is administered to cause elevated plasma melatonin concentrations between about CT 6 and about CT 18 to achieve a phase advance. For Tables 13 and 19, beta-blocker levels are elevated between about CT 14 and about CT 18 for facilitating a phase delay. For Tables 15 and 17, beta-blockers should be active between about CT 18 and about CT 1 for facilitating a phase advance. Melatonin agonists and stimulants can be substituted for melatonin, accompanied by reduced light exposure; melatonin antagonists and inverse agonists can be given during the opposite zone of the melatonin PRC as recommended for melatonin, accompanied by light exposure, as described in Example 9.

EXAMPLE 13

Many infants, most totally blind people, and a few sighted adults have free-running circadian rhythms that are not entrained to the light/dark cycle. These individuals therefore would benefit from the applications of the methods of this invention to entrain their free-running circadian rhythms to about a 24 hour period.

Most free-running people have an intrinsic circadian period of slightly more than 24 hours. For these people, a small daily phase advance is required to entrain their intrinsic circadian period to about 24 hours. Entrainment of sighted people can be accomplished using appropriately-timed bright exposure. Exogenous melatonin administration is used in a method provided by the invention wherein melatonin, a melatonin agonist or a compound that stimulates endogenous production of melatonin in a human is administered at a time and for a duration of plasma melatonin or agonist concentration greater than quiescent melatonin or equivalent agonist plasma concentration wherein the time overlaps with the endogenous melatonin onset and preferably does not overlap endogenous melatonin offset. Exogenous melatonin agonist or a compound that stimulates endogenous production of melatonin in a human is also effectively administered wherein a greater portion of the advance zone of the melatonin PRC (from about CT 6 to about CT 18) is stimulated than the delay zone of the melatonin PRC (from about CT 18 to about CT 6). For the blind, melatonin administration is required daily (or almost daily) to maintain entrainment of their intrinsically free-running circadian rhythms. For sighted people, melatonin administration can be supplemented with increased light exposure scheduled to occur during a greater portion of the time interval between about CT 18 to about CT 6 (particularly from about CT 18 to about CT 1) than the time interval from about CT 6 to about CT 18 (particularly between about CT 14 and about CT 18). For both sighted and blind people, melatonin antagonists or inverse agonists can be administered instead of, or even in addition to, exogenous melatonin at times described for light exposure. For both sighted and blind people, compounds that block endogenous melatonin production can be administered instead of or along with the other phase-shifting agents disclosed herein, most preferably during the time interval from about CT 14 to about CT 18, or to coincide with the entire endogenous melatonin profile (about CT 14 to about CT 1).

Some free-running individuals have intrinsic circadian periods that are slightly less than 24 hours. These people require a phase delay to entrain their intrinsic circadian period to about 24 hours. Exogenous melatonin administration is used in a method provided by the invention wherein melatonin, a melatonin agonist or a compound that stimulates endogenous production of melatonin in a human is administered at a time and for a duration of plasma melatonin or agonist concentration greater than quiescent melatonin or equivalent agonist plasma concentration wherein the time overlaps with the endogenous melatonin offset and preferably does not overlap endogenous melatonin onset. Exogenous melatonin agonist or a compound that stimulates endogenous production of melatonin in a human is also effectively administered wherein a greater portion of the delay zone of the melatonin PRC (from about CT 18 to about CT 6) is stimulated than the advance zone of the melatonin PRC (from about CT 6 to about CT 18). For the blind, melatonin administration is required daily (or almost daily) to maintain entrainment of their intrinsically free-running circadian rhythms. For sighted people, melatonin administration can be supplemented with increased light exposure scheduled to occur during a greater portion of the time interval between about CT 6 to about CT 18 (particularly from about CT 14 to about CT 18) than the time interval from about CT 18 to about CT 6 (particularly between about CT 18 and about CT 1). For both sighted and blind people, melatonin antagonists or inverse agonists can be administered instead of, or even in addition to, exogenous melatonin at times described for light exposure. For both sighted and blind people, compounds that block endogenous melatonin production can be administered instead of or along with the other phase-shifting agents disclosed herein, most preferably or to coincide with the entire endogenous melatonin profile also co-incident with the melatonin profile (about CT 14 to about CT 1).

It should be understood that the foregoing disclosure emphasizes certain specific embodiments of the invention and that all modifications or alternatives equivalent thereto are within the spirit and scope of the invention as set forth in the appended claims.

TABLE 1

To Produce a Phase Delay

| CT of Administration | If AUC Important, Duration of Exogenous Pulse of at Least About: | If AUC not Important, Duration of Exogenous Pulse of at Least About: |
|---|---|---|
| 18 | ≦12 hrs | ≦19 hrs |
| 19 | ≦11 hrs | ≦18 hrs |
| 20 | ≦10 hrs | ≦17 hrs |
| 21 | ≦9 hrs | ≦16 hrs |
| 22 | ≦8 hrs | ≦15 hrs |
| 23 | ≦7 hrs | ≦14 hrs |
| 0 | ≦6 hrs | ≦13 hrs |
| 1 | ≦5 hrs | ≦12 hrs |
| 2 | ≦4 hrs | ≦11 hrs |
| 3 | ≦3 hrs | ≦10 hrs |
| 4 | ≦2 hrs | ≦9 hrs |
| 5 | ≦1 hrs | ≦8 hrs |

TABLE 2

To Produce a Phase Advance

| CT of Administration | Duration of Exogenous Pulse of at Least About: | Optimal Duration of Exogenous Pulse of About |
|---|---|---|
| 6 | 8 hrs | 12 hrs |
| 7 | 7 hrs | 11 hrs |
| 8 | 6 hrs | 10 hrs |
| 9 | 5 hrs | 9 hrs |
| 10 | 4 hrs | 8 hrs |
| 11 | 3 hrs | 7 hrs |
| 12 | 2 hrs | 6 hrs |
| 13 | 1 hr | 5 hrs |
| 14 | — | 4 hrs |
| 15 | — | 3 hrs |
| 16 | — | 2 hrs |
| 17 | — | 1 hr |

TABLE 3

Melatonin used as a soporific, to avoid phase delays

| At CT | Maximal Duration of Exogenous Pulse, if AUC not Important, Should be About: | Maximal Duration of Exogenous Pulse, if AUC Important, Should be About: |
|---|---|---|
| 12 | <12 hrs | <6 hrs |
| 13 | <11 hrs | <5 hrs |
| (DLMO) 14 | <10 hrs | <4 hrs |
| 15 | <9 hrs | <3 hrs |
| (Bedtime) 16 | <8 hrs | <2 hrs |
| 17 | <7 hrs | <1 hr |
| 18 | Avoid | Avoid |
| 19 | Avoid | Avoid |

TABLE 5

When to Obtain Light Exposure for Stimulating the Light PRC
(and When to Take a Melatonin Antagonist or Inverse Agonist), and
When to Obtain Light Exposure for Avoiding (or Reducing)
Stimulation of the Melatonin PRC by Suppressing Endogenous Melatonin Productions
(and When to Take a Compound that Blocks Endogenous Production of Melatonin)
(Row 0 is in Embarkation Time, all others are in Destination Time.)

| Time Zones | | Light Exposure to: | Day 1 | Day 2 | Day 3 | Day 4 | Day 5 |
|---|---|---|---|---|---|---|---|
| ↑ | 15 | Stim. Light PRC | 10 pm– 10 am | 11 pm– 11 am | M– N | 1 am– 1 pm | 2 am– 2 pm |
|   |    | Avoid Stim. Mel. PRC | 9 am– 1 pm | 7 am– 11 am | 8 am– N | 9 am– 1 pm | 10 am– 2 pm |
| ↑ | 14 | Stim. Light PRC | 11 pm– 11 am | M– N | 1 am– 1 pm | 2 am– 2 pm | 3 am– 3 pm |
|   |    | Avoid Stim. Mel. PRC | 7 am– 11 am | 8 am– N | 9 am– 1 pm | 10 am– 2 pm | 11 am– 3 pm |
| ↑ | 13 | Stim. Light PRC | M– N | 1 am– 1 pm | 2 am– 2 pm | 3 am– 3 pm | 4 am– 4 pm |
|   |    | Avoid Stim. Mel. PRC | 8 am– N | 9 am– 1 pm | 10 am– 2 pm | 11 am– 3 pm | N– 4 pm |
| ↑ | 12 | Stim. Light PRC | 1 am– 1 pm | 2 am– 2 pm | 3 am– 3 pm | 4 am– 4 pm | 5 am– 5 pm |
|   |    | Avoid Stim. Mel. PRC | 9 am– 1 pm | 10 am– 2 pm | 11 am– 3 pm | N– 4 pm | 1 pm– 5 pm |
| ↑ | 11 | Stim. Light PRC | 2 am– 2 pm | 3 am– 3 pm | 4 am– 4 pm | 5 am– 5 pm | 6 am– 6 pm |
|   |    | Avoid Stim. Mel. PRC | 10 am– 2 pm | 11 am– 3 pm | N– 4 pm | 1 pm– 5 pm | 2 pm– 6 pm |
| ↑ | 10 | Stim. Light PRC | 3 am– 3 pm | 4 am– 4 pm | 5 am– 5 pm | 6 am– 6 pm | 7 am– 7 pm |
|   |    | Avoid Stim. Mel. PRC | 11 am– 3 pm | N– 4 pm | 1 pm– 5 pm | 2 pm– 6 pm | 3 pm– 7 pm |
| ↑ | 9 | Stim. Light PRC | 4 am– 4 pm | 5 am– 5 pm | 6 am– 6 pm | 7 am– 7 pm | 8 am– 8 pm |
|   |    | Avoid Stim. Mel. PRC | N– 4 pm | 1 pm– 5 pm | 2 pm– 6 pm | 3 pm– 7 pm | 4 pm– 8 pm |
| ↑ | 8 | Stim. Light PRC | 5 am– 5 pm | 6 am– 6 pm | 7 am– 7 pm | 8 am– 8 pm | 9 am– 9 pm |
|   |    | Avoid Stim. Mel. PRC | 1 pm– 5 pm | 2 pm– 6 pm | 3 pm– 7 pm | 4 pm– 8 pm | 5 pm– 9 pm |
| ↑ | 7 | Stim. Light PRC | 6 am– 6 pm | 7 am– 7 pm | 8 am– 8 pm | 9 am– 9 pm | 10 am– 10 pm |
|   |    | Avoid Stim. Mel. PRC | 2 pm– 6 pm | 3 pm– 7 pm | 4 pm– 8 pm | 5 pm– 9 pm | 6 pm– 10 pm |
| ↑ | 6 | Stim. Light PRC | 7 am– 7 pm | 8 am– 8 pm | 9 am– 9 pm | 10 am– 10 pm | 11 am– 11 pm |
|   |    | Avoid Stim. Mel. PRC | 3 pm– 7 pm | 4 pm– 8 pm | 5 pm– 9 pm | 6 pm– 10 pm | 7 pm– 11 pm |
| ↑ | 5 | Stim. Light PRC | 8 am– 8 pm | 9 am– 9 pm | 10 am– 10 pm | 11 am– 11 pm | N– M |
|   |    | Avoid Stim. Mel. PRC | 4 pm– 8 pm | 5 pm– 9 pm | 6 pm– 10 pm | 7 pm– 11 pm | 8 pm– M |
| ↑ | 4 | Stim. Light PRC | 9 am– 9 pm | 10 am– 10 pm | 11 am– 11 pm | N– M | 1 pm– 1 am |
|   |    | Avoid Stim. Mel. PRC | 5 pm– 9 pm | 6 pm– 10 pm | 7 pm– 11 pm | 8 pm– M | 9 pm– 1 am |
| ↑ | 3 | Stim. Light PRC | 10 am– 10 pm | 11 am– 11 pm | N– M | 1 pm– 1 am | |

TABLE 5-continued

When to Obtain Light Exposure for Stimulating the Light PRC
(and When to Take a Melatonin Antagonist or Inverse Agonist), and
When to Obtain Light Exposure for Avoiding (or Reducing)
Stimulation of the Melatonin PRC by Suppressing Endogenous Melatonin Productions
(and When to Take a Compound that Blocks Endogenous Production of Melatonin)
(Row 0 is in Embarkation Time, all others are in Destination Time.)

| Time Zones | | | | | | | |
|---|---|---|---|---|---|---|---|
| | | Avoid Stim. Mel. PRC | 6 pm– 10 pm | 7 pm– 11 pm | 8 pm– M | 9 pm– 1 am | |
| ↑ | 2 | Stim. Light PRC | 11 am– 11 pm | N– M | 1 pm– 1 am | | |
| | | Avoid Stim. Mel. PRC | 7 pm– 11 pm | 3 pm– M | 9 pm– 1 am | | |
| ↑ | 1 | Stim. Light PRC | N– M | 1 pm– 1 am | | | |
| | | Avoid Stim. Mel. PRC | 8 pm– M | 9 pm– 1 am | | | |
| West | 0 | Stim. Light PRC | 1 pm– 1 am | | | | |
| | | Avoid Stim. Mel. PRC | 9 pm– 1 am | | | | |
| East | 0 | Stim. Light PRC | 1 am– 1 pm | | | | |
| | | Avoid Stim. Mel. PRC | 1 am– 8 am | | | | |
| ↓ | 1 | Stim. Light PRC | 2 am– 2 pm | 1 am– 1 pm | | | |
| | | Avoid Stim. Mel. PRC | 2 am– 9 am | 1 am– 8 am | | | |
| ↓ | 2 | Stim. Light PRC | 3 am– 3 pm | 2 am– 2 pm | 1 am– 1 pm | | |
| | | Avoid Stim. Mel. PRC | 3 am– 10 am | 2 am– 9 am | 1 am– 8 am | | |
| ↓ | 3 | Stim. Light PRC | 4 am– 4 pm | 3 am– 3 pm | 2 am– 2 pm | 1 am– 1 pm | |
| | | Avoid Stim. Mel. PRC | 4 am– 11 am | 3 am– 10 am | 2 am– 9 am | 1 am– 8 am | |
| ↓ | 4 | Stim. Light PRC | 5 am– 5 pm | 4 am– 4 pm | 3 am– 3 pm | 2 am– 2 pm | 1 am– 1 pm |
| | | Avoid Stim. Mel. PRC | 5 am– N | 4 am– 11 am | 3 am– 10 am | 2 am– 9 am | 1 am– 8 am |
| ↓ | 5 | Stim. Light PRC | 6 am– 6 pm | 5 am– 5 pm | 4 am– 4 pm | 3 am– 3 pm | 2 am– 2 pm |
| | | Avoid Stim. Mel. PRC | 6 am– 1 pm | 5 am– N | 4 am– 11 am | 3 am– 10 am | 2 am– 9 am |
| ↓ | 6 | Stim. Light PRC | 7 am– 7 pm | 6 am– 6 pm | 5 am– 5 pm | 4 am– 4 pm | 3 am– 3 pm |
| | | Avoid Stim. Mel. PRC | 7 am– 2 pm | 6 am– 1 pm | 5 am– N | 4 am– 11 am | 3 am– 10 am |
| ↓ | 7 | Stim. Light PRC | 8 am– 8 pm | 7 am– 7 pm | 6 am– 6 pm | 5 am– 5 pm | 4 am– 4 pm |
| | | Avoid Stim. Mel. PRC | 8 am– 3 pm | 7 am– 2 pm | 6 am– 1 pm | 5 am– N | 4 am– 11 am |
| ↓ | 8 | Stim. Light PRC | 9 am– 9 pm | 8 am– 8 pm | 7 am– 7 pm | 6 am– 6 pm | 5 am– 5 pm |
| | | Avoid Stim. Mel. PRC | 9 am– 4 pm | 8 am– 3 pm | 7 am– 2 pm | 6 am– 1 pm | 5 am– N |
| ↓ | 9 | Stim. Light PRC | 10 am– 10 pm | 9 am– 9 pm | 8 am– 8 pm | 7 am– 7 pm | 6 am– 6 pm |
| | | Avoid Stim. Mel. PRC | 10 am– 5 pm | 9 am– 4 pm | 8 am– 3 pm | 7 am– 2 pm | 6 am– 1 pm |
| ↓ | 10 | Stim. Light PRC | 11 am– 11 pm | 10 am– 10 pm | 9 am– 9 pm | 8 am– 8 pm | 7 am– 7 pm |
| | | Avoid Stim. Mel. PRC | 11 am– 6 pm | 10 am– 5 pm | 9 am– 4 pm | 8 am– 3 pm | 7 am– 2 pm |
| ↓ | 11 | Stim. Light PRC | N– M | 11 am– 11 pm | 10 am– 10 pm | 9 am– 9 pm | 8 am– 8 pm |
| | | Avoid Stim. Mel. PRC | N– 7 pm | 11 am– 6 pm | 10 am– 5 pm | 9 am– 4 pm | 8 am– 3 pm |
| ↓ | 12 | Stim. Light PRC | 1 pm– 1 am | N– M | 11 am– 11 pm | 10 am– 10 pm | 9 am– 9 pm |
| | | Avoid Stim. Mel. PRC | 1 pm– 8 pm | N– 7 pm | 11 am– 6 pm | 10 am– 5 pm | 9 am– 4 pm |
| ↓ | 13 | Stim. Light PRC | 2 pm– 2 am | 1 pm– 1 am | N– M | 11 am– 11 pm | 10 am– 10 pm |
| | | Avoid Stim. Mel. PRC | 2 pm– 9 pm | 1 pm– 8 pm | N– 7 pm | 11 am– 6 pm | 10 am– 5 pm |
| ↓ | 14 | Stim. Light PRC | 3 pm– 3 am | 2 pm– 2 am | 1 pm– 1 am | N– M | 11 am– 11 pm |
| | | Avoid Stim. Mel. PRC | 3 pm– 10 pm | 2 pm– 9 pm | 1 pm– 8 pm | N– 7 pm | 11 am– 6 pm |
| ↓ | 15 | Stim. Light PRC | 4 pm– 4 am | 3 pm– 3 am | 2 pm– 2 am | 1 pm– 1 am | N– M |
| | | Avoid Stim. Mel. PRC | 4 pm– 11 pm | 3 pm– 10 pm | 2 pm– 9 pm | 1 pm– 8 pm | N– 7 pm |

| Time Zones | | Day 6 | Day 7 | Day 8 | Day 9 | Day 10 | Day 11 |
|---|---|---|---|---|---|---|---|
| ↑ | 15 | 3 am– 3 pm | 4 am– 4 pm | 5 am– 5 pm | 6 am– 6 pm | 7 am– 7 pm | 8 am– 8 pm |
| | | 11 am– 3 pm | N– 4 pm | 1 pm– 5 pm | 2 pm– 6 pm | 3 pm– 7 pm | 4 pm– 8 pm |
| ↑ | 14 | 4 am– 4 pm | 5 am– 5 pm | 6 am– 6 pm | 7 am– 7 pm | 8 am– 8 pm | 9 am– 9 pm |
| | | N– 4 pm | 1 pm– 5 pm | 2 pm– 6 pm | 3 pm– 7 pm | 4 pm– 8 pm | 5 pm– 9 pm |
| ↑ | 13 | 5 am– 5 pm | 6 am– 6 pm | 7 am– 7 pm | 8 am– 8 pm | 9 am– 9 pm | 10 am– 10 pm |
| | | 1 pm– 5 pm | 2 pm– 6 pm | 3 pm– 7 pm | 4 pm– 8 pm | 5 pm– 9 pm | 6 pm– 10 pm |
| ↑ | 12 | 6 am– 6 pm | 7 am– 7 pm | 8 am– 8 pm | 9 am– 9 pm | 10 am– 10 pm | 11 am– 11 pm |
| | | 2 pm– 6 pm | 3 pm– 7 pm | 4 pm– 8 pm | 5 pm– 9 pm | 6 pm– 10 pm | 7 pm– 11 pm |
| ↑ | 11 | 7 am– 7 pm | 8 am– 8 pm | 9 am– 9 pm | 10 am– 10 pm | 11 am– 11 pm | N– M |
| | | 3 pm– 7 pm | 4 pm– 8 pm | 5 pm– 9 pm | 6 pm– 10 pm | 7 pm– 11 pm | 8 pm– M |
| ↑ | 10 | 8 am– 8 pm | 9 am– 9 pm | 10 am– 10 pm | 11 am– 11 pm | N– M | 1 pm– 1 am |
| | | 4 pm– 8 pm | 5 pm– 9 pm | 6 pm– 10 pm | 7 pm– 11 pm | 8 pm– M | 9 pm– 1 am |
| ↑ | 9 | 9 am– 9 pm | 10 am– 10 pm | 11 am– 11 pm | N– M | 1 pm– 1 am | |
| | | 5 pm– 9 pm | 6 pm– 10 pm | 7 pm– 11 pm | 8 pm– M | 9 pm– 1 am | |
| ↑ | 8 | 10 am– 10 pm | 11 am– 11 pm | N– M | 1 pm– 1 am | 9 pm– 1 am | |
| | | 6 pm– 10 pm | 7 pm– 11 pm | 8 pm– M | 9 pm– 1 am | | |
| ↑ | 7 | 11 am– 11 pm | N– M | 1 pm– 1 am | | | |
| | | 7 pm– 11 pm | 8 pm– M | 9 pm– 1 am | | | |
| ↑ | 6 | N– M | 1 pm– 1 am | | | | |
| | | 8 pm– M | 9 pm– 1 am | | | | |
| ↑ | 5 | 1 pm– 1 am | | | | | |
| | | 9 pm– 1 am | | | | | |
| ↑ | 4 | | | | | | |
| ↑ | 3 | | | | | | |
| ↑ | 2 | | | | | | |
| ↑ | 1 | | | | | | |
| West | 0 | | | | | | |
| East | 0 | | | | | | |
| ↓ | 1 | | | | | | |
| ↓ | 2 | | | | | | |

TABLE 5-continued

When to Obtain Light Exposure for Stimulating the Light PRC
(and When to Take a Melatonin Antagonist or Inverse Agonist), and
When to Obtain Light Exposure for Avoiding (or Reducing)
Stimulation of the Melatonin PRC by Suppressing Endogenous Melatonin Productions
(and When to Take a Compound that Blocks Endogenous Production of Melatonin)
(Row 0 is in Embarkation Time, all others are in Destination Time.)

| | | | | | | | |
|---|---|---|---|---|---|---|---|
| ↓ | 3 | | | | | | |
| ↓ | 4 | | | | | | |
| ↓ | 5 | 1 am– 1 pm | | | | | |
| | | 1 am– 8 am | | | | | |
| ↓ | 6 | 2 am– 2 pm | 1 am– 1 pm | | | | |
| | | 2 am– 9 am | 1 am– 8 am | | | | |
| ↓ | 7 | 3 am– 3 pm | 2 am– 2 pm | 1 am– 1 pm | | | |
| | | 3 am– 10 am | 2 am– 9 am | 1 am– 8 am | | | |
| ↓ | 8 | 4 am– 4 pm | 3 am– 3 pm | 2 am– 2 pm | 1 am– 1 pm | | |
| | | 4 am– 11 am | 3 am– 10 am | 2 am– 9 am | 1 am– 8 am | | |
| ↓ | 9 | 5 am– 5 pm | 4 am– 4 pm | 3 am– 3 pm | 2 am– 2 pm | 1 am– 1 pm | |
| | | 5 am– N | 4 am– 11 am | 3 am– 10 am | 2 am– 9 am | 1 am– 8 am | |
| ↓ | 10 | 6 am– 6 pm | 5 am– 5 pm | 4 am– 4 pm | 3 am– 3 pm | 2 am– 2 pm | 1 am– 1 pm |
| | | 6 am– 1 pm | 5 am– N | 4 am– 11 am | 3 am– 10 am | 2 am– 9 am | 1 am– 8 am |
| ↓ | 11 | 7 am– 7 pm | 6 am– 6 pm | 5 am– 5 pm | 4 am– 4 pm | 3 am– 3 pm | 2 am– 2 pm |
| | | 7 am– 2 pm | 6 am– 1 pm | 5 am– N | 4 am– 11 am | 3 am– 10 am | 2 am– 9 am |
| ↓ | 12 | 8 am– 8 pm | 7 am– 7 pm | 6 am– 6 pm | 5 am– 5 pm | 4 am– 4 pm | 3 am– 3 pm |
| | | 8 am– 3 pm | 7 am– 2 pm | 6 am– 1 pm | 5 am– N | 4 am– 11 am | 3 am– 10 am |
| ↓ | 13 | 9 am– 9 pm | 8 am– 8 pm | 7 am– 7 pm | 6 am– 6 pm | 5 am– 5 pm | 4 am– 4 pm |
| | | 9 am– 4 pm | 8 am– 3 pm | 7 am– 2 pm | 6 am– 1 pm | 5 am– N | 4 am– 11 am |
| ↓ | 14 | 10 am– 10 pm | 9 am– 9 pm | 8 am– 8 pm | 7 am– 7 pm | 6 am– 6 pm | 5 am– 5 pm |
| | | 10 am– 5 pm | 9 am– 4 pm | 8 am– 3 pm | 7 am– 2 pm | 6 am– 1 pm | 5 am– N |
| ↓ | 15 | 11 am– 11 pm | 10 am– 10 pm | 9 am– 9 pm | 8 am– 8 pm | 7 am– 7 pm | 6 am– 6 pm |
| | | 11 am– 6 pm | 10 am– 5 pm | 9 am– 4 pm | 8 am– 3 pm | 7 am– 2 pm | 6 am– 1 pm |

| | Time Zones | Day 12 | Day 13 | Day 14 | Day 15 | Day 16 |
|---|---|---|---|---|---|---|
| ↑ | 15 | 9 am– 9 pm | 10 am– 10 pm | 11 am– 11 pm | N– M | 1 pm– 1 am |
| | | 5 pm– 9 pm | 6 pm– 10 pm | 7 pm– 11 pm | 8 pm– M | 9 pm– 1 am |
| ↑ | 14 | 10 am– 10 pm | 11 am– 11 pm | N– M | 1 pm– 1 am | |
| | | 6 pm– 10 pm | 7 pm– 11 pm | 8 pm– M | 9 pm– 1 am | |
| ↑ | 13 | 11 am– 11 pm | N– M | 1 pm– 1 am | | |
| | | 7 pm– 11 pm | 8 pm– M | 9 pm– 1 am | | |
| ↑ | 12 | N– M | 1 pm– 1 am | | | |
| | | 8 pm– M | 9 pm– 1 am | | | |
| ↑ | 11 | 1 pm– 1 am | | | | |
| | | 9 pm– 1 am | | | | |
| ↑ | 10 | | | | | |
| ↑ | 9 | | | | | |
| ↑ | 8 | | | | | |
| ↑ | 7 | | | | | |
| ↑ | 6 | | | | | |
| ↑ | 5 | | | | | |
| ↑ | 4 | | | | | |
| ↑ | 3 | | | | | |
| ↑ | 2 | | | | | |
| ↑ | 1 | | | | | |
| West | 0 | | | | | |
| East | 0 | | | | | |
| ↓ | 1 | | | | | |
| ↓ | 2 | | | | | |
| ↓ | 3 | | | | | |
| ↓ | 4 | | | | | |
| ↓ | 5 | | | | | |
| ↓ | 6 | | | | | |
| ↓ | 7 | | | | | |
| ↓ | 8 | | | | | |
| ↓ | 9 | | | | | |
| ↓ | 10 | | | | | |
| ↓ | 11 | 1 am– 1 pm | | | | |
| | | 1 am– 8 am | | | | |
| ↓ | 12 | 2 am– 2 pm | 2 am– 2 pm | | | |
| | | 2 am– 9 am | 2 am– 9 am | | | |
| ↓ | 13 | 3 am– 3 pm | 3 am– 3 pm | 3 am– 3 pm | | |
| | | 3 am– 10 am | 3 am– 10 am | 3 am– 10 am | | |
| ↓ | 14 | 4 am– 4 pm | 4 am– 4 pm | 4 am– 4 pm | 4 am– 4 pm | |
| | | 4 am– 11 am | 4 am– 11 am | 4 am– 11 am | 4 am– 11 am | |
| ↓ | 15 | 5 am– 5 pm | 5 am– 5 pm | 5 am– 5 pm | 5 am– 5 pm | 5 am– 5 pm |
| | | 5 am– N | 5 am– N | 5 am– N | 5 am– N | 5 am– N |

TABLE 6

When to Avoid Light Exposure to Avoid Stimulating the Light PRC
(and When to Take Melatonin, a Melatonin Agonist or a Compound that Stimulates
Endogenous Melatonin Production, and When to Avoid Light Exposure to Enhance their Phase-Shifting Effects);
When to Reduce Light Suppression of Endogenous Melatonin Production in order to Stimulate the Melatonin PRC
(Row 0 is in Embarkation Time, all others are in Destination Time)

| Time Zones | | Light Exposure to: | Day 1 | Day 2 | Day 3 | Day 4 | Day 5 |
|---|---|---|---|---|---|---|---|
| ↑ | 15 | Avoid Stim. Light PRC | 10 am– 10 pm | 11 am– 11 pm | N– M | 1 pm– 1 am | 2 pm– 2 am |
| | | Stim. Mel. PRC | 10 am– 5 pm | 11 am– 6 pm | N– 7 pm | 1 pm– 8 pm | 2 pm– 9 pm |
| ↑ | 14 | Avoid Stim. Light PRC | 11 am– 11 pm | N– M | 1 pm– 1 am | 2 pm– 2 am | 3 pm– 3 am |
| | | Stim. Mel. PRC | 11 am– 6 pm | N– 7 pm | 1 pm– 8 pm | 2 pm– 9 pm | 3 pm– 10 pm |
| ↑ | 13 | Avoid Stim. Light PRC | N– M | 1 pm– 1 am | 2 pm– 2 am | 3 pm– 3 am | 4 pm– 4 am |
| | | Stim. Mel. PRC | N– 7 pm | 1 pm– 8 pm | 2 pm– 9 pm | 3 pm– 10 pm | 4 pm– 11 pm |
| ↑ | 12 | Avoid Stim. Light PRC | 1 pm– 1 am | 2 pm– 2 am | 3 pm– 3 am | 4 pm– 4 am | 5 pm– 5 am |
| | | Stim. Mel. PRC | 1 pm– 8 pm | 2 pm– 9 pm | 3 pm– 10 pm | 4 pm– 11 pm | 5 pm– M |
| ↑ | 11 | Avoid Stim. Light PRC | 2 pm– 2 am | 3 pm– 3 am | 4 pm– 4 am | 5 pm– 5 am | 6 pm– 6 am |
| | | Stim. Mel. PRC | 2 pm– 9 pm | 3 pm– 10 pm | 4 pm– 11 pm | 5 pm– M | 6 pm– 1 am |
| ↑ | 10 | Avoid Stim. Light PRC | 3 pm– 3 am | 4 pm– 4 am | 5 pm– 5 am | 6 pm– 6 am | 7 pm– 7 am |
| | | Stim. Mel. PRC | 3 pm– 10 pm | 4 pm– 11 pm | 5 pm– M | 6 pm– 1 am | 7 pm– 2 am |
| ↑ | 9 | Avoid Stim. Light PRC | 4 pm– 4 am | 5 pm– 5 am | 6 pm– 6 am | 7 pm– 7 am | 8 pm– 8 am |
| | | Stim. Mel. PRC | 4 pm– 11 pm | 5 pm– M | 6 pm– 1 am | 7 pm– 2 am | 8 pm– 3 am |
| ↑ | 8 | Avoid Stim. Light PRC | 5 pm– 5 am | 6 pm– 6 am | 7 pm– 7 am | 8 pm– 8 am | 9 pm– 9 am |
| | | Stim. Mel. PRC | 5 pm– M | 6 pm– 1 am | 7 pm– 2 am | 8 pm– 3 am | 9 pm– 4 am |
| ↑ | 7 | Avoid Stim. Light PRC | 6 pm– 6 am | 7 pm– 7 am | 8 pm– 8 am | 9 pm– 9 am | 10 pm– 10 am |
| | | Stim. Mel. PRC | 6 pm– 1 am | 7 pm– 2 am | 8 pm– 3 am | 9 pm– 4 am | 10 pm– 5 am |
| ↑ | 6 | Avoid Stim. Light PRC | 7 pm– 7 am | 8 pm– 8 am | 9 pm– 9 am | 10 pm– 10 am | 11 pm– 11 am |
| | | Stim. Mel. PRC | 7 pm– 2 am | 8 pm– 3 am | 9 pm– 4 am | 10 pm– 5 am | 11 pm– 6 am |
| ↑ | 5 | Avoid Stim. Light PRC | 8 pm– 8 am | 9 pm– 9 am | 10 pm– 10 am | 11 pm– 11 am | M– N |
| | | Stim. Mel. PRC | 8 pm– 3 am | 9 pm– 4 am | 10 pm– 5 am | 11 pm– 6 am | M– 7 am |
| ↑ | 4 | Avoid Stim. Light PRC | 9 pm– 9 am | 10 pm– 10 am | 11 pm– 11 am | M– N | 1 am– 1 pm |
| | | Stim. Mel. PRC | 9 pm– 4 am | 10 pm– 5 am | 11 pm– 6 am | M– 7 am | 1 am– 8 am |
| ↑ | 3 | Avoid Stim. Light PRC | 10 pm– 10 am | 11 pm– 11 am | M– N | 1 am– 1 pm | |
| | | Stim. Mel. PRC | 10 pm– 5 am | 11 pm– 6 am | M– 7 am | 1 am– 8 am | |
| ↑ | 2 | Avoid Stim. Light PRC | 11 pm– 11 am | M– N | 1 am– 1 pm | | |
| | | Stim. Mel. PRC | 11 pm– 6 am | M– 7 am | 1 am– 8 am | | |
| ↑ | 1 | Avoid Stim. Light PRC | M– N | 1 am– 1 pm | | | |
| | | Stim. Mel. PRC | M– 7 am | 1 am– 8 am | | | |
| West | 0 | Avoid Stim. Light PRC | 1 am– 1 pm | | | | |
| | | Stim. Mel. PRC | 1 am– 8 am | | | | |
| East | 0 | Avoid Stim. Light PRC | 1 pm– 1 am | | | | |
| | | Stim. Mel. PRC | 9 pm– 1 am | | | | |
| ↓ | 1 | Avoid Stim. Light PRC | 2 pm– 2 am | 1 pm– 1 am | | | |
| | | Stim. Mel. PRC | 10 pm– 2 am | 9 pm– 1 am | | | |
| ↓ | 2 | Avoid Stim. Light PRC | 3 pm– 3 am | 2 pm– 2 am | 1 pm– 1 am | | |
| | | Stim. Mel. PRC | 11 pm– 3 am | 10 pm– 2 am | 9 pm– 1 am | | |
| ↓ | 3 | Avoid Stim. Light PRC | 4 pm– 4 am | 3 pm– 3 am | 2 pm– 2 am | 1 pm– 1 am | |
| | | Stim. Mel. PRC | M– 4 am | 11 pm– 3 am | 10 pm– 2 am | 9 pm– 1 am | |
| ↓ | 4 | Avoid Stim. Light PRC | 5 pm– 5 am | 4 pm– 4 am | 3 pm– 3 am | 2 pm– 2 am | 1 pm– 1 am |
| | | Stim. Mel. PRC | 1 am– 5 am | M– 4 am | 11 pm– 3 am | 10 pm– 2 am | 9 pm– 1 am |
| ↓ | 5 | Avoid Stim. Light PRC | 6 pm– 6 am | 5 pm– 5 am | 4 pm– 4 am | 3 pm– 3 am | 2 pm– 2 am |
| | | Stim. Mel. PRC | 2 am– 6 am | 1 am– 5 am | M– 4 am | 11 pm– 3 am | 10 pm– 2 am |
| ↓ | 6 | Avoid Stim. Light PRC | 7 pm– 7 am | 6 pm– 6 am | 5 pm– 5 am | 4 pm– 4 am | 3 pm– 3 am |
| | | Stim. Mel. PRC | 3 am– 7 am | 2 am– 6 am | 1 am– 5 am | M– 4 am | 11 pm– 3 am |
| ↓ | 7 | Avoid Stim. Light PRC | 8 pm– 8 am | 7 pm– 7 am | 6 pm– 6 am | 5 pm– 5 am | 4 pm– 4 am |
| | | Stim. Mel. PRC | 4 am– 8 am | 3 am– 7 am | 2 am– 6 am | 1 am– 5 am | M– 4 am |
| ↓ | 8 | Avoid Stim. Light PRC | 9 pm– 9 am | 8 pm– 8 am | 7 pm– 7 am | 6 pm– 6 am | 5 pm– 5 am |
| | | Stim. Mel. PRC | 5 am– 9 am | 4 am– 8 am | 3 am– 7 am | 2 am– 6 am | 1 am– 5 am |
| ↓ | 9 | Avoid Stim. Light PRC | 10 pm– 10 am | 9 pm– 9 am | 8 pm– 8 am | 7 pm– 7 am | 6 pm– 6 am |
| | | Stim. Mel. PRC | 6 am– 10 am | 5 am– 9 am | 4 am– 8 am | 3 am– 7 am | 2 am– 6 am |
| ↓ | 10 | Avoid Stim. Light PRC | 11 pm– 11 am | 10 pm– 10 am | 9 pm– 9 am | 8 pm– 8 am | 7 pm– 7 am |
| | | Stim. Mel. PRC | 7 am– 11 am | 6 am– 10 am | 5 am– 9 am | 4 am– 8 am | 3 am– 7 am |
| ↓ | 11 | Avoid Stim. Light PRC | M– N | 11 pm– 11 am | 10 pm– 10 am | 9 pm– 9 am | 8 pm– 8 am |
| | | Stim. Mel. PRC | 8 am– N | 7 am– 11 am | 6 am– 10 am | 5 am– 9 am | 4 am– 8 am |
| ↓ | 12 | Avoid Stim. Light PRC | 1 am– 1 pm | M– N | 11 pm– 11 am | 10 pm– 10 am | 9 pm– 9 am |
| | | Stim. Mel. PRC | 9 am– 1 pm | 8 am– N | 7 am– 11 am | 6 am– 10 am | 5 am– 9 am |
| ↓ | 13 | Avoid Stim. Light PRC | 2 am– 2 pm | 1 am– 1 pm | M– N | 11 pm– 11 am | 10 pm– 10 am |
| | | Stim. Mel. PRC | 10 am– 2 pm | 9 am– 1 pm | 8 am– N | 7 am– 11 am | 6 am– 10 am |
| ↓ | 14 | Avoid Stim. Light PRC | 3 am– 3 pm | 2 am– 2 pm | 1 am– 1 pm | M– N | 11 pm– 11 am |
| | | Stim. Mel. PRC | 11 am– 3 pm | 10 am– 2 pm | 9 am– 1 pm | 8 am– N | 7 am– 11 am |
| ↓ | 15 | Avoid Stim. Light PRC | 4 am– 4 pm | 3 am– 3 pm | 2 am– 2 pm | 1 am– 1 pm | M– N |
| | | Stim. Mel. PRC | N– 4 pm | 11 am– 3 pm | 10 am– 2 pm | 9 am– 1 pm | 8 am– N |

| Time Zones | | Day 6 | Day 7 | Day 8 | Day 9 | Day 10 | Day 11 |
|---|---|---|---|---|---|---|---|
| ↑ | 15 | 3 pm– 3 am | 4 pm– 4 am | 5 pm– 5 am | 6 pm– 6 am | 7 pm– 7 am | 8 pm– 8 am |
| | | 3 pm– 10 pm | 4 pm– 11 pm | 5 pm– M | 6 pm– 1 am | 7 pm– 2 am | 8 pm– 3 am |
| ↑ | 14 | 4 pm– 4 am | 5 pm– 5 am | 6 pm– 6 am | 7 pm– 7 am | 8 pm– 8 am | 9 pm– 9 am |
| | | 4 pm– 11 pm | 5 pm– M | 6 pm– 1 am | 7 pm– 2 am | 8 pm– 3 am | 9 pm– 4 am |

TABLE 6-continued

When to Avoid Light Exposure to Avoid Stimulating the Light PRC
(and When to Take Melatonin, a Melatonin Agonist or a Compound that Stimulates
Endogenous Melatonin Production, and When to Avoid Light Exposure to Enhance their Phase-Shifting Effects);
When to Reduce Light Suppression of Endogenous Melatonin Production in order to Stimulate the Melatonin PRC
(Row 0 is in Embarkation Time, all others are in Destination Time)

| | | | | | | | |
|---|---|---|---|---|---|---|---|
| ↑ | 13 | 5 pm– 5 am<br>5 pm– M | 6 pm– 6 am<br>6 pm– 1 am | 7 pm– 7 am<br>7 pm– 2 am | 8 pm– 8 am<br>8 pm– 3 am | 9 pm– 9 am<br>9 pm– 4 am | 10 pm– 10 am<br>10 pm– 5 am |
| ↑ | 12 | 6 pm– 6 am<br>6 pm– 1 am | 7 pm– 7 am<br>7 pm– 2 am | 8 pm– 8 am<br>8 pm– 3 am | 9 pm– 9 am<br>9 pm– 4 am | 10 pm– 10 am<br>10 pm– 5 am | 11 pm– 11 am<br>11 pm– 6 am |
| ↑ | 11 | 7 pm– 7 am<br>7 pm– 2 am | 8 pm– 8 am<br>8 pm– 3 am | 9 pm– 9 am<br>9 pm– 4 am | 10 pm– 10 am<br>10 pm– 5 am | 11 pm– 11 am<br>11 pm– 6 am | M– N<br>M– 7 am |
| ↑ | 10 | 8 pm– 8 am<br>8 pm– 3 am | 9 pm– 9 am<br>9 pm– 4 am | 10 pm– 10 am<br>10 pm– 5 am | 11 pm– 11 am<br>11 pm– 6 am | M– N<br>M– 7 am | 1 am– 1 pm<br>1 am– 8 am |
| ↑ | 9 | 9 pm– 9 am<br>9 pm– 4 am | 10 pm– 10 am<br>10 pm– 5 am | 11 pm– 11 am<br>11 pm– 6 am | M– N<br>M– 7 am | 1 am– 1 pm<br>1 am– 8 am | |
| ↑ | 8 | 10 pm– 10 am<br>10 pm– 5 am | 11 pm– 11 am<br>11 pm– 6 am | M– N<br>M– 7 am | 1 am– 1 pm<br>1 am– 8 am | | |
| ↑ | 7 | 11 pm– 11 am<br>11 pm– 6 am | M– N<br>M– 7 am | 1 am– 1 pm<br>1 am– 8 am | | | |
| ↑ | 6 | M– N<br>M– 7 am | 1 am– 1 pm<br>1 am– 8 am | | | | |
| ↑ | 5 | 1 am– 1 pm<br>1 am– 8 am | | | | | |
| ↑ | 4 | | | | | | |
| ↑ | 3 | | | | | | |
| ↑ | 2 | | | | | | |
| ↑ | 1 | | | | | | |
| West | 0 | | | | | | |
| East | 0 | | | | | | |
| ↓ | 1 | | | | | | |
| ↓ | 2 | | | | | | |
| ↓ | 3 | | | | | | |
| ↓ | 4 | | | | | | |
| ↓ | 5 | 1 pm– 1 am<br>9 pm– 1 am | | | | | |
| ↓ | 6 | 2 pm– 2 am<br>10 pm– 2 am | 1 pm– 1 am<br>9 pm– 1 am | | | | |
| ↓ | 7 | 3 pm– 3 am<br>11 pm– 3 am | 2 pm– 2 am<br>10 pm– 2 am | 1 pm– 1 am<br>9 pm– 1 am | | | |
| ↓ | 8 | 4 pm– 4 am<br>M– 4 am | 3 pm– 3 am<br>11 pm– 3 am | 2 pm– 2 am<br>10 pm– 2 am | 1 pm– 1 am<br>9 pm– 1 am | | |
| ↓ | 9 | 5 pm– 5 am<br>1 am– 5 am | 4 pm– 4 am<br>M– 4 am | 3 pm– 3 am<br>11 pm– 3 am | 2 pm– 2 am<br>10 pm– 2 am | 1 pm– 1 am<br>9 pm– 1 am | |
| ↓ | 10 | 6 pm– 6 am<br>2 am– 6 am | 5 pm– 5 am<br>1 am– 5 am | 4 pm– 4 am<br>M– 4 am | 3 pm– 3 am<br>11 pm– 3 am | 2 pm– 2 am<br>10 pm– 2 am | 1 pm– 1 am<br>9 pm– 1 am |
| ↓ | 11 | 7 pm– 7 am<br>3 am– 7 am | 6 pm– 6 am<br>2 am– 6 am | 5 pm– 5 am<br>1 am– 5 am | 4 pm– 4 am<br>M– 4 am | 3 pm– 3 am<br>11 pm– 3 am | 2 pm– 2 am<br>10 pm– 2 am |
| ↓ | 12 | 8 pm– 8 am<br>4 am– 8 am | 7 pm– 7 am<br>3 am– 7 am | 6 pm– 6 am<br>2 am– 6 am | 5 pm– 5 am<br>1 am– 5 am | 4 pm– 4 am<br>M– 4 am | 3 pm– 3 am<br>11 pm– 3 am |
| ↓ | 13 | 9 pm– 9 am<br>5 am– 9 am | 8 pm– 8 am<br>4 am– 8 am | 7 pm– 7 am<br>3 am– 7 am | 6 pm– 6 am<br>2 am– 6 am | 5 pm– 5 am<br>1 am– 5 am | 4 pm– 4 am<br>M– 4 am |
| ↓ | 14 | 10 pm– 10 am<br>6 am– 10 am | 9 pm– 9 am<br>5 am– 9 am | 8 pm– 8 am<br>4 am– 8 am | 7 pm– 7 am<br>3 am– 7 am | 6 pm– 6 am<br>2 am– 6 am | 5 pm– 5 am<br>1 am– 5 am |
| ↓ | 15 | – 11 am<br>7 am– 11 am | 10 pm– 10 am<br>6 am– 10 am | 9 pm– 9 am<br>5 am– 9 am | 8 pm– 8 am<br>4 am– 8 am | 7 pm– 7 am<br>3 am– 7 am | 6 pm– 6 am<br>2 am– 6 am |

| | Time Zones | Day 12 | Day 13 | Day 14 | Day 15 | Day 16 |
|---|---|---|---|---|---|---|
| ↑ | 15 | 9 pm– 9 am<br>9 pm– 4 am | 10 pm– 10 am<br>10 pm– 5 am | 11 pm– 11 am<br>11 pm– 6 am | M– N<br>M– 7 am | 1 am– 1 pm<br>1 am– 8 am |
| ↑ | 14 | 10 pm– 10 am<br>10 pm– 5 am | 11 pm– 11 am<br>11 pm– 6 am | M– N<br>M– 7 am | 1 am– 1 pm<br>1 am– 8 am | |
| ↑ | 13 | 11 pm– 11 am<br>11 pm– 6 am | M– N<br>M– 7 am | 1 am– 1 pm<br>1 am– 8 am | | |
| ↑ | 12 | M– N<br>M– 7 am | 1 am– 1 pm<br>1 am– 8 am | | | |
| ↑ | 11 | 1 am– 1 pm<br>1 am– 8 am | | | | |
| ↑ | 10 | | | | | |
| ↑ | 9 | | | | | |
| ↑ | 8 | | | | | |
| ↑ | 7 | | | | | |
| ↑ | 6 | | | | | |
| ↑ | 5 | | | | | |
| ↑ | 4 | | | | | |
| ↑ | 3 | | | | | |
| ↑ | 2 | | | | | |
| ↑ | 1 | | | | | |

TABLE 6-continued

When to Avoid Light Exposure to Avoid Stimulating the Light PRC
(and When to Take Melatonin, a Melatonin Agonist or a Compound that Stimulates
Endogenous Melatonin Production, and When to Avoid Light Exposure to Enhance their Phase-Shifting Effects);
When to Reduce Light Suppression of Endogenous Melatonin Production in order to Stimulate the Melatonin PRC
(Row 0 is in Embarkation Time, all others are in Destination Time)

| | | | | | | |
|---|---|---|---|---|---|---|
| West | 0 | | | | | |
| East | 0 | | | | | |
| ↓ | 1 | | | | | |
| ↓ | 2 | | | | | |
| ↓ | 3 | | | | | |
| ↓ | 4 | | | | | |
| ↓ | 5 | | | | | |
| ↓ | 6 | | | | | |
| ↓ | 7 | | | | | |
| ↓ | 8 | | | | | |
| ↓ | 9 | | | | | |
| ↓ | 10 | | | | | |
| ↓ | 11 | 1 pm– 1 am | | | | |
| | | 9 pm– 1 am | | | | |
| ↓ | 12 | 2 pm– 2 am | 1 pm– 1 am | | | |
| | | 10 pm– 2 am | 9 pm– 1 am | | | |
| ↓ | 13 | 3 pm– 3 am | 2 pm– 2 am | 1 pm– 1 am | | |
| | | 11 pm– 3 am | 10 pm– 2 am | 9 pm– 1 am | | |
| ↓ | 14 | 4 pm– 4 am | 3 pm– 3 am | 2 pm– 2 am | 1 pm– 1 am | |
| | | M– 4 am | 11 pm– 3 am | 10 pm– 2 am | 9 pm– 1 am | |
| ↓ | 15 | 5 pm– 5 am | 4 pm– 4 am | 3 pm– 3 am | 2 pm– 2 am | 1 pm– 1 am |
| | | 1 am– 5 am | M– 4 am | 11 pm– 3 am | 10 pm– 2 am | 9 pm– 1 am |

TABLE 4

To Avoid a Phase Shift

| CT of Administration | Duration of Exogenous Pulse |
|---|---|
| 13 | ≅13 hrs |
| 12 | ≅14 hrs |
| 11 | ≅15 hrs |
| 10 | ≅16 hrs |
| 9 | ≅17 hrs |
| 8 | ≅18 hrs |
| 7 | ≅19 hrs |

TABLE 7

Times to Take a β-Blocker, With or Without a Delayed-Release (DR).
β-Blocker of 7-hour Duration Going East, 4-hour Duration Going West.
Assume Immediate Onset of Action.

| Time Zones | | Day 1 | Day 2 | Day 3 | Day 4 | Day 5 | Day 6 |
|---|---|---|---|---|---|---|---|
| ↑ | 15 | 5 am | 6 am | 7 am | 8 am | 9 am | 10 am |
| ↑ | 14 | 6 am | 7 am | 8 am | 9 am | 10 am | 11 am |
| ↑ | 13 | 7 am | 8 am | 9 am | 10 am | 11 am | Noon |
| ↑ | 12 | 8 am | 9 am | 10 am | 11 am | Noon | 1 pm |
| ↑ | 11 | 9 am | 10 am | 11 am | Noon | 1 pm | 2 pm |
| ↑ | 10 | 10 am | 11 am | Noon | 1 pm | 2 pm | 3 pm |
| ↑ | 9 | 11 am | Noon | 1 pm | 2 pm | 3 pm | 4 pm |
| ↑ | 8 | Noon | 1 pm | 2 pm | 3 pm | 4 pm | 5 pm |
| ↑ | 7 | 1 pm | 2 pm | 3 pm | 4 pm | 5 pm | 6 pm |
| ↑ | 6 | 2 pm | 3 pm | 4 pm | 5 pm | 6 pm | 7 pm |
| ↑ | 5 | 3 pm | 4 pm | 5 pm | 6 pm | 7 pm | 8 pm |
| ↑ | 4 | 4 pm | 5 pm | 6 pm | 7 pm | 8 pm | |
| ↑ | 3 | 5 pm | 6 pm | 7 pm | 8 pm | | |
| ↑ | 2 | 6 pm | 7 pm | 8 pm | | | |
| ↑ | 1 | 7 pm | 8 pm | | | | |
| West | 0 | 8 pm | | | | | |
| East | 0 | 9 pm, 4 h DR | | | | | |
| ↓ | 1 | 9 pm, 5 h DR | 9 pm, 4 h DR | | | | |

TABLE 7-continued

Times to Take a β-Blocker, With or Without a Delayed-Release (DR).
β-Blocker of 7-hour Duration Going East, 4-hour Duration Going West.
Assume Immediate Onset of Action.

| | | | | | | | |
|---|---|---|---|---|---|---|---|
| ↓ | 2 | 9 pm, 6 h DR | 9 pm, 5 h DR | 9 pm, 4 h DR | | | |
| ↓ | 3 | 9 pm, 7 h DR | 9 pm, 6 h DR | 9 pm, 5 h DR | 9 pm, 4 h DR | | |
| ↓ | 4 | 9 pm, 8 h DR | 9 pm, 7 h DR | 9 pm, 6 h DR | 9 pm, 5 h DR | 9 pm, 4 h DR | |
| ↓ | 5 | 9 pm, 9 h DR | 9 pm, 8 h DR | 9 pm, 7 h DR | 9 pm, 6 h DR | 9 pm, 5 h DR | 9 pm, 4 h DR |
| ↓ | 6 | 7 am | 9 pm, 9 h DR | 9 pm, 8 h DR | 9 pm, 7 h DR | 9 pm, 6 h DR | 9 pm, 5 h DR |
| ↓ | 7 | 8 am | 7 am | 9 pm, 9 h DR | 9 pm, 8 h DR | 9 pm, 7 h DR | 9 pm, 6 h DR |
| ↓ | 8 | 9 am | 8 am | 7 am | 9 pm, 9 h DR | 9 pm, 8 h DR | 9 pm, 7 h DR |
| ↓ | 9 | 10 am | 9 am | 8 am | 7 am | 9 pm, 9 h DR | 9 pm, 8 h DR |
| ↓ | 10 | 11 am | 10 am | 9 am | 8 am | 7 am | 9 pm, 9 h DR |
| ↓ | 11 | Noon | 11 am | 10 am | 9 am | 8 am | 7 am |
| ↓ | 12 | 1 pm | Noon | 11 am | 10 am | 9 am | 8 am |
| ↓ | 13 | 2 pm | 1 pm | Noon | 11 am | 10 am | 9 am |
| ↓ | 14 | 3 pm | 2 pm | 1 pm | Noon | 11 am | 10 am |
| ↓ | 15 | 4 pm | 3 pm | 2 pm | 1 pm | Noon | 11 am |

| Time Zones | | Day 7 | Day 8 | Day 9 | Day 10 | Day 11 | Day 12 |
|---|---|---|---|---|---|---|---|
| ↑ | 15 | 11 am | Noon | 1 pm | 2 pm | 3 pm | 4 pm |
| ↑ | 14 | Noon | 1 pm | 2 pm | 1 pm | 4 pm | 5 pm |
| ↑ | 13 | 1 pm | 2 pm | 3 pm | 4 pm | 5 pm | 6 pm |
| ↑ | 12 | 2 pm | 3 pm | 4 pm | 5 pm | 6 pm | 7 pm |
| ↑ | 11 | 1 pm | 4 pm | 5 pm | 6 pm | 7 pm | 8 pm |
| ↑ | 10 | 4 pm | 5 pm | 6 pm | 7 pm | 8 pm | |
| ↑ | 9 | 5 pm | 6 pm | 7 pm | 8 pm | | |
| ↑ | 8 | 6 pm | 7 pm | 8 pm | | | |
| ↑ | 7 | 7 pm | 8 pm | | | | |
| ↑ | 6 | 8 pm | | | | | |
| ↑ | 5 | | | | | | |
| ↑ | 4 | | | | | | |
| ↑ | 3 | | | | | | |
| ↑ | 2 | | | | | | |
| ↑ | 1 | | | | | | |
| West | 0 | | | | | | |
| East | 0 | | | | | | |
| ↓ | 1 | | | | | | |
| ↓ | 2 | | | | | | |
| ↓ | 3 | | | | | | |
| ↓ | 4 | | | | | | |
| ↓ | 5 | | | | | | |
| ↓ | 6 | 9 pm, 4 h DR | | | | | |
| ↓ | 7 | 9 pm, 5 h DR | 9 pm, 4 h DR | | | | |
| ↓ | 8 | 9 pm, 6 h DR | 9 pm, 5 h DR | 9 pm, 4 h DR | | | |
| ↓ | 9 | 9 pm, 7 h DR | 9 pm, 6 h DR | 9 pm, 5 h DR | 9 pm, 4 h DR | | |
| ↓ | 10 | 9 pm, 8 h DR | 9 pm, 7 h DR | 9 pm, 6 h DR | 9 pm, 5 h DR | 9 pm, 4 h DR | |
| ↓ | 11 | 9 pm, 9 h DR | 9 pm, 8 h DR | 9 pm, 7 h DR | 9 pm, 6 h DR | 9 pm, 5 h DR | 9 pm, 4 h DR |
| ↓ | 12 | 7 am | 9 pm, 9 h DR | 9 pm, 8 h DR | 9 pm, 7 h DR | 9 pm, 6 h DR | 9 pm, 5 h DR |
| ↓ | 13 | 8 am | 7 am | 9 pm, 9 h DR | 9 pm, 8 h DR | 9 pm, 7 h DR | 9 pm, 6 h DR |
| ↓ | 14 | 9 am | 8 am | 7 am | 9 pm, 9 h DR | 9 pm, 8 h DR | 9 pm, 7 h DR |
| ↓ | 15 | 10 am | 9 am | 8 am | 7 am | 9 pm, 9 h DR | 9 pm, 8 h DR |

| Time Zones | | Day 13 | Day 14 | Day 15 | Day 16 |
|---|---|---|---|---|---|
| ↑ | 15 | 5 pm | 6 pm | 7 pm | 8 pm |
| ↑ | 14 | 6 pm | 7 pm | 8 pm | |
| ↑ | 13 | 7 pm | 8 pm | | |
| ↑ | 12 | 8 pm | | | |
| ↑ | 11 | | | | |
| ↑ | 10 | | | | |
| ↑ | 9 | | | | |
| ↑ | 8 | | | | |
| ↑ | 7 | | | | |
| ↑ | 6 | | | | |
| ↑ | 5 | | | | |
| ↑ | 4 | | | | |
| ↑ | 3 | | | | |
| ↑ | 2 | | | | |
| ↑ | 1 | | | | |
| West | 0 | | | | |
| East | 0 | | | | |
| ↓ | 1 | | | | |
| ↓ | 2 | | | | |
| ↓ | 3 | | | | |
| ↓ | 4 | | | | |
| ↓ | 5 | | | | |
| ↓ | 6 | | | | |

TABLE 7-continued

Times to Take a β-Blocker, With or Without a Delayed-Release (DR).
β-Blocker of 7-hour Duration Going East, 4-hour Duration Going West.
Assume Immediate Onset of Action.

| | | | | | |
|---|---|---|---|---|---|
| ↓ | 7 | | | | |
| ↓ | 8 | | | | |
| ↓ | 9 | | | | |
| ↓ | 10 | | | | |
| ↓ | 11 | | | | |
| ↓ | 12 | 9 pm, 4 h DR | | | |
| ↓ | 13 | 9 pm, 5 h DR | 9 pm, 4 h DR | | |
| ↓ | 14 | 9 pm, 6 h DR | 9 pm, 5 h DR | 9 pm, 4 h DR | |
| ↓ | 15 | 9 pm, 7 h DR | 9 pm, 6 h DR | 9 pm, 5 h DR | 9 pm, 4 h DR |

TABLE 8

When to Take Middle-of-the-night Melatonin Going East, Combined with a Lower to Moderate Dose
IR Formulation at Bedtime (Assume About 9 pm and About 0.5 mg has About a 5 h duration). Do Not Take After:

| Time Zones | | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|---|
| East | 0 | 1 am | | | | | | | | | | |
| ↓ | 1 | 1 am | | | | | | | | | | |
| ↓ | 2 | 1 am | | | | | | | | | | |
| ↓ | 3 | 1 am | | | | | | | | | | |
| ↓ | 4 | 1 am | | | | | | | | | | |
| ↓ | 5 | 1 am | | | | | | | | | | |
| ↓ | 6 | 2 am | 1 am | | | | | | | | | |
| ↓ | 7 | 3 am | 2 am | 1 am | | | | | | | | |
| ↓ | 8 | 4 am | 3 am | 2 am | 1 am | | | | | | | |
| ↓ | 9 | 5 am | 4 am | 3 am | 2 am | 1 am | | | | | | |
| ↓ | 10 | 6 am | 5 am | 4 am | 3 am | 2 am | 1 am | | | | | |
| ↓ | 11 | 7 am | 6 am | 5 am | 4 am | 3 am | 2 am | 1 am | | | | |
| ↓ | 12 | 8 am | 7 am | 6 am | 5 am | 4 am | 3 am | 2 am | 1 am | | | |
| ↓ | 13 | 9 am | 8 am | 7 am | 6 am | 5 am | 4 am | 3 am | 2 am | 1 am | | |
| ↓ | 14 | 10 am | 9 am | 8 am | 7 am | 6 am | 5 am | 4 am | 3 am | 2 am | 1 am | |
| ↓ | 15 | 11 am | 10 am | 9 am | 8 am | 7 am | 6 am | 5 am | 4 am | 3 am | 2 am | 1 am |

TABLE 9

Maximal (Ideal) Duration of Melatonin at Bedtime
(Assume About 9 pm), With or Without a Delayed-Release (DR)

| Time Zones | | Day 1 | Day 2 | Day 3 | Day 4 | Day 5 | Day 6 | Day 7 |
|---|---|---|---|---|---|---|---|---|
| ↑ | 15 | 1 h | 2 h | 3 h | 4 h | 5 h | 6 h | 7 h |
| ↑ | 14 | 2 h | 3 h | 4 h | 5 h | 6 h | 7 h | 8 h |
| ↑ | 13 | 3 h | 4 h | 5 h | 6 h | 7 h | 8 h | 9 h |
| ↑ | 12 | 4 h | 5 h | 6 h | 7 h | 8 h | 9 h | 10 h |
| ↑ | 11 | 5 h | 6 h | 7 h | 8 h | 9 h | 10 h | 11 h |
| ↑ | 10 | 6 h | 7 h | 8 h | 9 h | 10 h | 11 h | 12 h |
| ↑ | 9 | 7 h | 8 h | 9 h | 10 h | 11 h | 12 h | 12 h, 1 h DR |
| ↑ | 8 | 8 h | 9 h | 10 h | 11 h | 12 h | 12 h, 1 h DR | 12 h, 2 h DR |
| ↑ | 7 | 9 h | 10 h | 11 h | 12 h | 12 h, 1 h DR | 12 h, 2 h DR | 12 h, 3 h DR |
| ↑ | 6 | 10 h | 11 h | 12 h | 12 h, 1 h DR | 12 h, 2 h DR | 12 h, 3 h DR | 12 h, 4 h DR |
| ↑ | 5 | 11 h | 12 h | 12 h, 1 h DR | 12 h, 2 h DR | 12 h, 3 h DR | 12 h, 4 h DR | |
| ↑ | 4 | 12 h | 12 h, 1 h DR | 12 h, 2 h DR | 12 h, 3 h DR | 12 h, 4 h DR | | |
| ↑ | 3 | 12 h, 1 h DR | 12 h, 2 h DR | 12 h, 3 h DR | 12 h, 4 h DR | | | |
| ↑ | 2 | 12 h, 2 h DR | 12 h, 3 h DR | 12 h, 4 h DR | | | | |
| ↑ | 1 | 12 h, 3 h DR | 12 h, 4 h DR | | | | | |
| West | 0 | 12 h, 4 h DR | | | | | | |
| East | 0 | 4 h | | | | | | |
| ↓ | 1 | 5 h | 4 h | | | | | |
| ↓ | 2 | 6 h | 5 h | 4 h | | | | |
| ↓ | 3 | 7 h | 6 h | 5 h | 4 h | | | |
| ↓ | 4 | 8 h | 7 h | 6 h | 5 h | 4 h | | |
| ↓ | 5 | 9 h | 8 h | 7 h | 6 h | 5 h | 4 h | |
| ↓ | 6 | 10 h | 9 h | 8 h | 7 h | 6 h | 5 h | 4 h |
| ↓ | 7 | 11 h | 10 h | 9 h | 8 h | 7 h | 6 h | 5 h |
| ↓ | 8 | 12 h | 11 h | 10 h | 9 h | 8 h | 7 h | 6 h |
| ↓ | 9 | 12 h, 1 h DR | 12 h | 11 h | 10 h | 9 h | 8 h | 7 h |
| ↓ | 10 | 12 h, 2 h DR | 12 h, 1 h DR | 12 h | 11 h | 10 h | 9 h | 8 h |
| ↓ | 11 | 12 h, 3 h DR | 12 h, 2 h DR | 12 h, 1 h DR | 12 h | 11 h | 10 h | 9 h |
| ↓ | 12 | 12 h, 4 h DR | 12 h, 3 h DR | 12 h, 2 h DR | 12 h, 1 h DR | 12 h | 11 h | 10 h |

TABLE 9-continued

Maximal (Ideal) Duration of Melatonin at Bedtime
(Assume About 9 pm), With or Without a Delayed-Release (DR)

| | | | | | | | | |
|---|---|---|---|---|---|---|---|---|
| ↓ | 13 | 12 h, 5 h DR | 12 h, 4 h DR | 12 h, 3 h DR | 12 h, 2 h DR | 12 h, 1 h DR | 12 h | 11 h |
| ↓ | 14 | 12 h, 6 h DR | 12 h, 5 h DR | 12 h, 4 h DR | 12 h, 3 h DR | 12 h, 2 h DR | 12 h, 1 h DR | 12 h |
| ↓ | 15 | 12 h, 7 h DR | 12 h, 6 h DR | 12 h, 5 h DR | 12 h, 4 h DR | 12 h, 3 h DR | 12 h, 2 h DR | 12 h, 1 h DR |

| Time Zones | | Day 8 | Day 9 | Day 10 | Day 11 | Day 12 |
|---|---|---|---|---|---|---|
| ↑ | 15 | 8 h | 9 h | 10 h | 11 h | 12 h |
| ↑ | 14 | 9 h | 10 h | 11 h | 12 h | 12 h, 1 h DR |
| ↑ | 13 | 10 h | 11 h | 12 h | 12 h, 1 h DR | 12 h, 2 h DR |
| ↑ | 12 | 11 h | 12 h | 12 h, 1 h DR | 12 h, 2 h DR | 12 h, 3 h DR |
| ↑ | 11 | 12 h | 12 h, 1 h DR | 12 h, 2 h DR | 12 h, 3 h DR | 12 h, 4 h DR |
| ↑ | 10 | 12 h, 1 h DR | 12 h, 2 h DR | 12 h, 3 h DR | 12 h, 4 h DR | |
| ↑ | 9 | 12 h, 2 h DR | 12 h, 3 h DR | 12 h, 4 h DR | | |
| ↑ | 8 | 12 h, 3 h DR | 12 h, 4 h DR | | | |
| ↑ | 7 | 12 h, 4 h DR | | | | |
| ↑ | 6 | | | | | |
| ↑ | 5 | | | | | |
| ↑ | 4 | | | | | |
| ↑ | 3 | | | | | |
| ↑ | 2 | | | | | |
| ↑ | 1 | | | | | |
| West | 0 | | | | | |
| East | 0 | | | | | |
| ↓ | 1 | | | | | |
| ↓ | 2 | | | | | |
| ↓ | 3 | | | | | |
| ↓ | 4 | | | | | |
| ↓ | 5 | | | | | |
| ↓ | 6 | | | | | |
| ↓ | 7 | 4 h | | | | |
| ↓ | 8 | 5 h | 4 h | | | |
| ↓ | 9 | 6 h | 5 h | 4 h | | |
| ↓ | 10 | 7 h | 6 h | 5 h | 4 h | |
| ↓ | 11 | 8 h | 7 h | 6 h | 5 h | 4 h |
| ↓ | 12 | 9 h | 8 h | 7 h | 6 h | 5 h |
| ↓ | 13 | 10 h | 9 h | 8 h | 7 h | 6 h |
| ↓ | 14 | 11 h | 10 h | 9 h | 8 h | 7 h |
| ↓ | 15 | 12 h | 11 h | 10 h | 9 h | 8 h |

| Time Zones | | Day 13 | Day 14 | Day 15 | Day 16 |
|---|---|---|---|---|---|
| ↑ | 15 | 12 h, 1 h DR | 12 h, 2 h DR | 12 h, 3 h DR | 12 h, 4 h DR |
| ↑ | 14 | 12 h, 2 h DR | 12 h, 3 h DR | 12 h, 4 h DR | |
| ↑ | 13 | 12 h, 3 h DR | 12 h, 4 h DR | | |
| ↑ | 12 | 12 h, 4 h DR | | | |
| ↑ | 11 | | | | |
| ↑ | 10 | | | | |
| ↑ | 9 | | | | |
| ↑ | 8 | | | | |
| ↑ | 7 | | | | |
| ↑ | 6 | | | | |
| ↑ | 5 | | | | |
| ↑ | 4 | | | | |
| ↑ | 3 | | | | |
| ↑ | 2 | | | | |
| ↑ | 1 | | | | |
| West | 0 | | | | |
| East | 0 | | | | |
| ↓ | 1 | | | | |
| ↓ | 2 | | | | |
| ↓ | 3 | | | | |
| ↓ | 4 | | | | |
| ↓ | 5 | | | | |
| ↓ | 6 | | | | |
| ↓ | 7 | | | | |
| ↓ | 8 | | | | |
| ↓ | 9 | | | | |
| ↓ | 10 | | | | |
| ↓ | 11 | | | | |
| ↓ | 12 | 4 h | | | |
| ↓ | 13 | 5 h | 4 h | | |
| ↓ | 14 | 6 h | 5 h | 4 h | |
| ↓ | 15 | 7 h | 6 h | 5 h | 4 h |

TABLE 10

When to Take Low-Dose of Melatonin, About 12-hour Duration, Going East or West,
With or Without a Delayed-Release (DR).

| Time Zones | | Day 1 | Day 2 | Day 3 | Day 4 | Day 5 | Day 6 |
|---|---|---|---|---|---|---|---|
| ↑ | 15 | 10 am | 11 am | Noon | 1 pm | 2 pm | 3 pm |
| ↑ | 14 | 11 am | Noon | 1 pm | 2 pm | 3 pm | 4 pm |
| ↑ | 13 | Noon | 1 pm | 2 pm | 3 pm | 4 pm | 5 pm |
| ↑ | 12 | 1 pm | 2 pm | 3 pm | 4 pm | 5 pm | 6 pm |
| ↑ | 11 | 2 pm | 3 pm | 4 pm | 5 pm | 6 pm | 7 pm |
| ↑ | 10 | 3 pm | 4 pm | 5 pm | 6 pm | 7 pm | 8 pm |
| ↑ | 9 | 4 pm | 5 pm | 6 pm | 7 pm | 8 pm | 9 pm |
| ↑ | 8 | 5 pm | 6 pm | 7 pm | 8 pm | 9 pm | 9 pm, 1 h DR |
| ↑ | 7 | 6 pm | 7 pm | 8 pm | 9 pm | 9 pm, 1 h DR | 9 pm, 2 h DR |
| ↑ | 6 | 7 pm | 8 pm | 9 pm | 9 pm, 1 h DR | 9 pm, 2 h DR | 9 pm, 3 h DR |
| ↑ | 5 | 8 pm | 9 pm | 9 pm, 1 h DR | 9 pm, 2 h DR | 9 pm, 3 h DR | 9 pm, 4 h DR |
| ↑ | 4 | 9 pm | 9 pm, 1 h DR | 9 pm, 2 h DR | 9 pm, 3 h DR | 9 pm, 4 h DR | |
| ↑ | 3 | 9 pm, 1 h DR | 9 pm, 2 h DR | 9 pm, 3 h DR | 9 pm, 4 h DR | | |
| ↑ | 2 | 9 pm, 2 h DR | 9 pm, 3 h DR | 9 pm, 4 h DR | | | |
| ↑ | 1 | 9 pm, 3 h DR | 9 pm, 4 h DR | | | | |
| West | 0 | 9 pm, 4 h DR | | | | | |
| East | 0 | 1 pm | | | | | |
| ↓ | 1 | 2 pm | 1 pm | | | | |
| ↓ | 2 | 3 pm | 2 pm | 1 pm | | | |
| ↓ | 3 | 4 pm | 3 pm | 2 pm | 1 pm | | |
| ↓ | 4 | 5 pm | 4 pm | 3 pm | 2 pm | 1 pm | |
| ↓ | 5 | 6 pm | 5 pm | 4 pm | 3 pm | 2 pm | 1 pm |
| ↓ | 6 | 7 pm | 6 pm | 5 pm | 4 pm | 3 pm | 2 pm |
| ↓ | 7 | 8 pm | 7 pm | 6 pm | 5 pm | 4 pm | 3 pm |
| ↓ | 8 | 9 pm | 8 pm | 7 pm | 6 pm | 5 pm | 4 pm |
| ↓ | 9 | 9 pm, 1 h DR | 9 pm | 8 pm | 7 pm | 6 pm | 5 pm |
| ↓ | 10 | 9 pm, 2 h DR | 9 pm, 1 h DR | 9 pm | 8 pm | 7 pm | 6 pm |
| ↓ | 11 | 9 pm, 3 h DR | 9 pm, 2 h DR | 9 pm, 1 h DR | 9 pm | 8 pm | 7 pm |
| ↓ | 12 | 9 pm, 4 h DR | 9 pm, 3 h DR | 9 pm, 2 h DR | 9 pm, 1 h DR | 9 pm | 8 pm |
| ↓ | 13 | 9 pm, 5 h DR | 9 pm, 4 h DR | 9 pm, 3 h DR | 9 pm, 2 h DR | 9 pm, 1 h DR | 9 pm |
| ↓ | 14 | 9 pm, 6 h DR | 9 pm, 5 h DR | 9 pm, 4 h DR | 9 pm, 3 h DR | 9 pm, 2 h DR | 9 pm, 1 h DR |
| ↓ | 15 | 9 pm, 7 h DR | 9 pm, 6 h DR | 9 pm, 5 h DR | 9 pm, 4 h DR | 9 pm, 3 h DR | 9 pm, 2 h DR |

| Time Zones | | Days 7 | Day 8 | Day 9 | Day 10 | Day 11 |
|---|---|---|---|---|---|---|
| ↑ | 15 | 4 pm | 5 pm | 6 pm | 7 pm | 8 pm |
| ↑ | 14 | 5 pm | 6 pm | 7 pm | 8 pm | 9 pm |
| ↑ | 13 | 6 pm | 7 pm | 8 pm | 9 pm | 9 pm, 1 h DR |
| ↑ | 12 | 7 pm | 8 pm | 9 pm | 9 pm, 1 h DR | 9 pm, 2 h DR |
| ↑ | 11 | 8 pm | 9 pm | 9 pm, 1 h DR | 9 pm, 2 h DR | 9 pm, 3 h DR |
| ↑ | 10 | 9 pm | 9 pm, 1 h DR | 9 pm, 2 h DR | 9 pm, 3 h DR | 9 pm, 4 h DR |
| ↑ | 9 | 9 pm, 1 h DR | 9 pm, 2 h DR | 9 pm, 3 h DR | 9 pm, 4 h DR | |
| ↑ | 8 | 9 pm, 2 h DR | 9 pm, 3 h DR | 9 pm, 4 h DR | | |
| ↑ | 7 | 9 pm, 3 h DR | 9 pm, 4 h DR | | | |
| ↑ | 6 | 9 pm, 4 h DR | | | | |
| ↑ | 5 | | | | | |
| ↑ | 4 | | | | | |
| ↑ | 3 | | | | | |
| ↑ | 2 | | | | | |
| ↑ | 1 | | | | | |
| West | 0 | | | | | |
| East | 0 | | | | | |
| ↓ | 1 | | | | | |
| ↓ | 2 | | | | | |
| ↓ | 3 | | | | | |
| ↓ | 4 | | | | | |
| ↓ | 5 | | | | | |
| ↓ | 6 | 1 pm | | | | |
| ↓ | 7 | 2 pm | 1 pm | | | |
| ↓ | 8 | 3 pm | 2 pm | 1 pm | | |
| ↓ | 9 | 4 pm | 3 pm | 2 pm | 1 pm | |
| ↓ | 10 | 5 pm | 4 pm | 3 pm | 2 pm | 1 pm |
| ↓ | 11 | 6 pm | 5 pm | 4 pm | 3 pm | 2 pm |
| ↓ | 12 | 7 pm | 6 pm | 5 pm | 4 pm | 3 pm |
| ↓ | 13 | 8 pm | 7 pm | 6 pm | 5 pm | 4 pm |
| ↓ | 14 | 9 pm | 8 pm | 7 pm | 6 pm | 5 pm |
| ↓ | 15 | 9 pm, 1 h DR | 9 pm | 8 pm | 7 pm | 6 pm |

| Time Zones | | Day 12 | Day 13 | Day 14 | Day 15 | Day 16 |
|---|---|---|---|---|---|---|
| ↑ | 15 | 9 pm | 9 pm, 1 h DR | 9 pm, 2 h DR | 9 pm, 3 h DR | 9 pm, 4 h DR |
| ↑ | 14 | 9 pm, 1 h DR | 9 pm, 2 h DR | 9 pm, 3 h DR | 9 pm, 4 h DR | |
| ↑ | 13 | 9 pm, 2 h DR | 9 pm, 3 h DR | 9 pm, 4 h DR | | |
| ↑ | 12 | 9 pm, 3 h DR | 9 pm, 4 h DR | | | |

TABLE 10-continued

When to Take Low-Dose of Melatonin, About 12-hour Duration, Going East or West,
With or Without a Delayed-Release (DR).

| | | | | | | |
|---|---|---|---|---|---|---|
| ↑ | 11 | 9 pm, 4 h DR | | | | |
| ↑ | 10 | | | | | |
| ↑ | 9 | | | | | |
| ↑ | 8 | | | | | |
| ↑ | 7 | | | | | |
| ↑ | 6 | | | | | |
| ↑ | 5 | | | | | |
| ↑ | 4 | | | | | |
| ↑ | 3 | | | | | |
| ↑ | 2 | | | | | |
| ↑ | 1 | | | | | |
| West | 0 | | | | | |
| East | 0 | | | | | |
| ↓ | 1 | | | | | |
| ↓ | 2 | | | | | |
| ↓ | 3 | | | | | |
| ↓ | 4 | | | | | |
| ↓ | 5 | | | | | |
| ↓ | 6 | | | | | |
| ↓ | 7 | | | | | |
| ↓ | 8 | | | | | |
| ↓ | 9 | | | | | |
| ↓ | 10 | | | | | |
| ↓ | 11 | 1 pm | | | | |
| ↓ | 12 | 2 pm | 1 pm | | | |
| ↓ | 13 | 3 pm | 2 pm | 1 pm | | |
| ↓ | 14 | 4 pm | 3 pm | 2 pm | 1 pm | |
| ↓ | 15 | 5 pm | 4 pm | 3 pm | 2 pm | 1 pm |

TABLE 11

When to Take Melatonin, Going West.
Assume About 0.5 mg has About a 5 h Duration. Take No Earlier Than:

| Time Zones | | Day 1 | Day 2 | Day 3 | Day 4 | Day 5 | Day 6 | Day 7 | Day 8 |
|---|---|---|---|---|---|---|---|---|---|
| West | 0 | 1 am | | | | | | | |
| ↓ | 1 | Midnight | 1 am | | | | | | |
| ↓ | 2 | 11 pm | Midnight | 1 am | | | | | |
| ↓ | 3 | 10 pm | 11 pm | Midnight | 1 am | | | | |
| ↓ | 4 | 9 pm | 10 pm | 11 pm | Midnight | 1 am | | | |
| ↓ | 5 | 8 pm | 9 pm | 10 pm | 11 pm | Midnight | 1 am | | |
| ↓ | 6 | 7 pm | 8 pm | 9 pm | 10 pm | 11 pm | Midnight | 1 am | |
| ↓ | 7 | 6 pm | 7 pm | 8 pm | 9 pm | 10 pm | 11 pm | Midnight | 1 am |
| ↓ | 8 | 5 pm | 6 pm | 7 pm | 8 pm | 9 pm | 10 pm | 11 pm | Midnight |
| ↓ | 9 | 4 pm | 5 pm | 6 pm | 7 pm | 8 pm | 9 pm | 10 pm | 11 pm |
| ↓ | 10 | 3 pm | 4 pm | 5 pm | 6 pm | 7 pm | 8 pm | 9 pm | 10 pm |
| ↓ | 11 | 2 pm | 3 pm | 4 pm | 5 pm | 6 pm | 7 pm | 8 pm | 9 pm |
| ↓ | 12 | 1 pm | 2 pm | 3 pm | 4 pm | 5 pm | 6 pm | 7 pm | 8 pm |
| ↓ | 13 | Noon | 1 pm | 2 pm | 3 pm | 4 pm | 5 pm | 6 pm | 7 pm |

| Time Zones | | Day 9 | Day 10 | Day 11 | Day 12 | Day 13 | Day 14 |
|---|---|---|---|---|---|---|---|
| West | 0 | | | | | | |
| ↓ | 1 | | | | | | |
| ↓ | 2 | | | | | | |
| ↓ | 3 | | | | | | |
| ↓ | 4 | | | | | | |
| ↓ | 5 | | | | | | |
| ↓ | 6 | | | | | | |
| ↓ | 7 | | | | | | |
| ↓ | 8 | 1 am | | | | | |
| ↓ | 9 | Midnight | 1 am | | | | |
| ↓ | 10 | 11 pm | Midnight | 1 am | | | |
| ↓ | 11 | 10 pm | 11 pm | Midnight | 1 am | | |
| ↓ | 12 | 9 pm | 10 pm | 11 pm | Midnight | 1 am | |
| ↓ | 13 | 8 pm | 9 pm | 10 pm | 11 pm | Midnight | 1 am |

TABLE 12

Shiftworkers Delaying to On-Work Schedule with Melatonin, About a 12 h duration, Sustained-Release (SR), With or Without a Delayed-Release (DR).

| Day | Time |
|---|---|
| 0 | 1 am |
| 1 | 1 am |
| 2 | 2 am |
| 3 | 3 am |
| 4 | 4 am |
| 5 | 5 am |
| 6 | 6 am |
| 7 | 7 am |
| 8 | 8 am |
| 9 | 9 am |
| 10 | 9 am, 1 h DR |
| 11 | 9 am, 2 h DR |
| 12 | 9 am, 3 h DR |
| 13 | 9 am, 4 h DR |

TABLE 13

Shiftworkers Delaying to On-Work Schedule with β-Blocker, (Assume Immediate Onset of Action), About a 4 h Duration, Immediate-Release (IR).

| Day | Time |
|---|---|
| 0 | 9 pm |
| 1 | 9 pm |
| 2 | 10 pm |
| 3 | 11 pm |
| 4 | Midnight |
| 5 | 1 am |
| 6 | 2 am |
| 7 | 3 am |
| 8 | 4 am |
| 9 | 5 am |
| 10 | 6 am |
| 11 | 7 am |
| 12 | 8 am |
| 13 | 9 am |

TABLE 14

Shiftworkers Advancing to On-Work Schedule with Melatonin. About a 12 h duration, Sustained-Release (SR), With or Without a Delayed-Release (DR).

| Day | Time |
|---|---|
| 0 | 9 am, 4 h DR |
| 1 | 9 am, 4 h DR |
| 2 | 9 am, 3 h DR |
| 3 | 9 am, 2 h DR |
| 4 | 9 am, 1 h DR |
| 5 | 9 am |
| 6 | 8 am |
| 7 | 7 am |
| 8 | 6 am |
| 9 | 5 am |
| 10 | 4 am |
| 11 | 3 am |
| 12 | 2 am |
| 13 | 1 am |

TABLE 15

Shiftworkers Advancing to On-Work Schedule with β-Blocker (Assume Immediate Onset of Action), About a 7 h Duration, Immediate-Release (IR), With or Without a Delayed-Release (DR).

| Day | Time |
|---|---|
| 0 | 1 am |
| 1 | 1 am |
| 2 | Midnight |
| 3 | 11 pm |
| 4 | 10 pm |
| 5 | 9 pm |
| 6 | 8 pm |
| 7 | 7 pm |
| 8 | 6 pm |
| 9 | 5 pm |
| 10 | 9 am, 7 h DR |
| 11 | 9 am, 6 h DR |
| 12 | 9 am, 5 h DR |
| 13 | 9 am, 4 h DR |

TABLE 16

Shiftworkers Advancing to Off-Work Schedule with Metatonin, About a 12 h duration, Sustained-Release (SR), With or Without a Delayed-Release (DR).

| Day | Time |
|---|---|
| 0 | 9 pm, 4 h DR |
| 1 | 9 pm, 4 h DR |
| 2 | 9 pm, 3 h DR |
| 3 | 9 pm, 2 h DR |
| 4 | 9 pm, 1 h DR |
| 5 | 9 pm |
| 6 | 8 pm |
| 7 | 7 pm |
| 8 | 6 pm |
| 9 | 5 pm |
| 10 | 4 pm |
| 11 | 3 pm |
| 12 | 2 pm |
| 13 | 1 pm |

TABLE 17

Shiftworkers Advancing to Off-Work Schedule with β-Blocker (Assume Immediate Onset of Action), About a 7 h Duration, Immediate-Release (IR), With or Without a Delayed-Release (DR).

| Day | Time |
|---|---|
| 0 | 1 pm |
| 1 | 1 pm |
| 2 | Noon |
| 3 | 11 am |
| 4 | 10 am |
| 5 | 9 am |
| 6 | 8 am |
| 7 | 7 am |
| 8 | 9 pm, 9 h DR |
| 9 | 9 pm, 8 h DR |
| 10 | 9 pm, 7 h DR |
| 11 | 9 pm, 6 h DR |
| 12 | 9 pm, 5 h DR |
| 13 | 9 pm, 4 h DR |

TABLE 18

Shiftworkers Delaying to Off-Work Schedule with Melatonin, Sustained-Release (SR, About a 12 h duration), With or Without a Delayed-Release (DR).

| Day | Time |
|---|---|
| 0 | 1 pm |
| 1 | 1 pm |
| 2 | 2 pm |
| 3 | 3 pm |
| 4 | 4 pm |
| 5 | 5 pm |
| 6 | 6 pm |
| 7 | 7 pm |
| 8 | 8 pm |
| 9 | 9 pm |
| 10 | 9 pm, 1 h DR |
| 11 | 9 pm, 2 h DR |
| 12 | 9 pm, 3 h DR |
| 13 | 9 pm, 4 h DR |

TABLE 19

Shiftworkers Delaying to On-Work Schedule with β-Blocker, About a 4 h Duration, Immediate-Release (IR).

| Day | Time |
|---|---|
| 0 | 9 am |
| 1 | 9 am |
| 2 | 10 am |
| 3 | 11 am |
| 4 | Noon |
| 5 | 1 pm |
| 6 | 2 pm |
| 7 | 3 pm |
| 8 | 4 pm |
| 9 | 5 pm |
| 10 | 6 pm |
| 11 | 7 pm |
| 12 | 8 pm |
| 13 | 9 pm |

We claim:

1. A method for achieving a circadian rhythm phase-shifting effect in a human, the method comprising the step of
administering to the human an amount of melatonin, melatonin agonist or compound that increases endogenous production of melatonin in the human, wherein said administration produces in the human a plasma melatonin or agonist concentration of greater than quiescent melatonin or equivalent agonist levels at a time that overlaps with either onset of endogenous melatonin production in the human or offset of endogenous melatonin production in the human,
wherein when the circadian rhythm phase-shifting effect is a phase advance, melatonin, melatonin agonist or compound that increases endogenous production of melatonin in the human is administered at a time after about CT 6 and prior to CT 14 to produce plasma melatonin or agonist concentrations of greater than quiescent melatonin or equivalent agonist levels that overlap endogenous melatonin production onset, said greater than quiescent melatonin or equivalent agonist levels rise before the melatonin onset and fall after the melatonin onset; or
wherein when the circadian rhythm phase-shifting effect is a phase delay, melatonin, melatonin agonist or compound that increases endogenous production of melatonin in the human is administered at a time after about CT 18 and prior to CT 1 to produce plasma melatonin or agonist concentration of greater than quiescent melatonin or equivalent agonist levels that overlaps offset of endogenous melatonin production, said greater than quiescent melatonin or equivalent agonist levels rise before the melatonin offset and fall after the melatonin offset.

2. A method according to claim 1 wherein the circadian rhythm phase-shifting effect is a phase advance and wherein administration of melatonin, melatonin agonist or a compound that increases endogenous melatonin production in the human produces in the human a plasma melatonin or agonist concentration of greater than quiescent melatonin or equivalent agonist levels after CT 6, that persists until at least after CT 14 and is reduced to quiescent melatonin or equivalent agonist levels between about CT 18 and the offset of endogenous melatonin production.

3. A method according to claim 1 or 2 wherein exogenous melatonin, melatonin agonist or compound that increases endogenous production of melatonin in the human is administered to a human in an immediate-release formulation.

4. A method according to claim 1 or 2 wherein exogenous melatonin, melatonin agonist or compound that increases endogenous production of melatonin in the human is administered to a human in a delayed-release formulation.

5. A method according to claim 1 or 2 wherein exogenous melatonin, melatonin agonist or compound that increases endogenous production of melatonin in the human is administered to a human in a sustained-release formulation.

6. A method according to claim 2 wherein exogenous melatonin, melatonin agonist or compound that increases endogenous production of melatonin in the human is administered to a human formulation in any combination of an immediate-release formulation, a delayed-release formulation or a sustained-release formulation.

7. A method for achieving a circadian rhythm phase-shifting effect in a human, the method comprising administering to the human an amount of melatonin, melatonin agonist or compound that increases endogenous production of melatonin in the human, wherein said administration produces in the human a plasma melatonin or agonist concentration of greater than quiescent melatonin or equivalent agonist levels for a time or in a concentration that is different during a time interval from about ct 6 to about ct 18 than that produced during the time interval from about CT 18 to about CT 6, wherein when the circadian rhythm phase-shifting effect is a phase advance, melatonin, melatonin agonist or compound that increases endogenous production of melatonin in the human is administered after about CT 6 and prior to CT 14, or when the circadian rhythm phase-shifting effect is a phase delay, melatonin, melatonin agonist or compound that increases endogenous production of melatonin in the human is administered after about CT 18 and prior to CT 1.

8. A method according to claim 7 wherein the circadian rhythm phase-shifting effect is a phase advance, the method comprising administering to the human an amount of melatonin, melatonin agonist or compound that increases endogenous production of melatonin in the human, wherein said administration produces in the human a plasma melatonin or agonist concentration of greater than quiescent melatonin or equivalent agonist levels for a time or in a concentration during a time interval from about CT 6 to about CT 18 that is greater than that produced during the time interval from about CT 18 to about CT 6, wherein melatonin, melatonin agonist or compound that increases endogenous production of melatonin in the human is administered after about CT 6 and prior to CT 14.

9. A method for alleviating a circadian rhythm disorder in a human, the method comprising the step of achieving a circadian phase-shifting effect in the human according to the method of claim 1.

10. The method of claim 9 wherein the circadian rhythm disorder is jet lag.

* * * * *